(12) United States Patent
Bradner et al.

(10) Patent No.: US 9,714,946 B2
(45) Date of Patent: Jul. 25, 2017

(54) BROMODOMAIN BINDING REAGENTS AND USES THEREOF

(71) Applicant: Dana-Farber Cancer Institute, Inc., Boston, MA (US)

(72) Inventors: James E. Bradner, Weston, MA (US); Jun Qi, Sharon, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/774,958

(22) PCT Filed: Mar. 11, 2014

(86) PCT No.: PCT/US2014/023386
§ 371 (c)(1),
(2) Date: Sep. 11, 2015

(87) PCT Pub. No.: WO2014/159392
PCT Pub. Date: Oct. 2, 2014

(65) Prior Publication Data
US 2016/0033519 A1    Feb. 4, 2016

Related U.S. Application Data

(60) Provisional application No. 61/781,472, filed on Mar. 14, 2013.

(51) Int. Cl.
*G01N 33/58* (2006.01)
*C07D 519/00* (2006.01)
*C07D 495/14* (2006.01)
*G01N 33/50* (2006.01)

(52) U.S. Cl.
CPC ........... *G01N 33/58* (2013.01); *C07D 495/14* (2013.01); *C07D 519/00* (2013.01); *G01N 33/5008* (2013.01)

(58) Field of Classification Search
CPC ..... G01N 33/58; C07D 495/14; C07D 519/00
See application file for complete search history.

(56) References Cited

U.S. PATENT DOCUMENTS

| | | |
|---|---|---|
| 5,712,274 A | 1/1998 | Sueoka et al. |
| 5,846,972 A | 12/1998 | Buckman et al. |
| 7,528,143 B2 | 5/2009 | Noronha et al. |
| 7,750,152 B2 | 7/2010 | Hoffman et al. |
| 7,786,299 B2 | 8/2010 | Hoffmann et al. |
| 7,816,530 B2 | 10/2010 | Grauert |
| 7,825,246 B2 | 11/2010 | Noronha et al. |

(Continued)

FOREIGN PATENT DOCUMENTS

| | | |
|---|---|---|
| EP | 0 989 131 B1 | 11/2002 |
| JP | 2008-156311 | 7/2008 |
| WO | WO 2007/095188 A2 | 8/2007 |
| WO | WO 2009/084693 A1 | 7/2009 |
| WO | WO 2011/054553 A1 | 5/2011 |
| WO | WO 2011/054841 A1 | 5/2011 |
| WO | WO 2011/054843 A1 | 5/2011 |
| WO | WO 2011/054844 A1 | 5/2011 |
| WO | WO 2011/054845 A1 | 5/2011 |
| WO | WO 2011/054846 A1 | 5/2011 |

(Continued)

OTHER PUBLICATIONS

International Search Report and Written Opinion for PCT/US2014/023386, mailed Jul. 9, 2014.

(Continued)

*Primary Examiner* — Shafiqul Haq
(74) *Attorney, Agent, or Firm* — Wolf, Greenfield & Sacks, P.C.

(57) ABSTRACT

The present invention provides compounds of the Formula (I) and (II), and salts thereof, wherein $L^1$, $L^2$, A, B, Z, and $R^O$ are as defined herein. The present invention also provides synthetic intermediates, methods of preparation and use, and kits comprising such compounds. Such compounds, when bound to a label or probe (B), may be useful in various assays for identifying bromodomain binding agents, for example, specific for the BET-family of bromodomains.

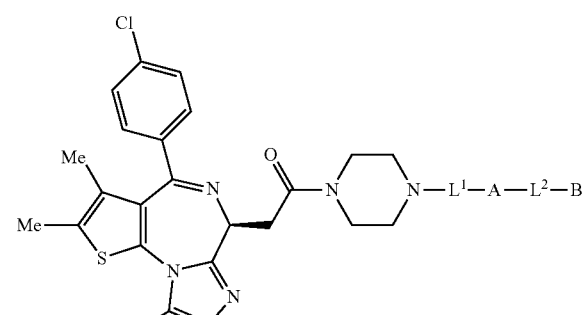

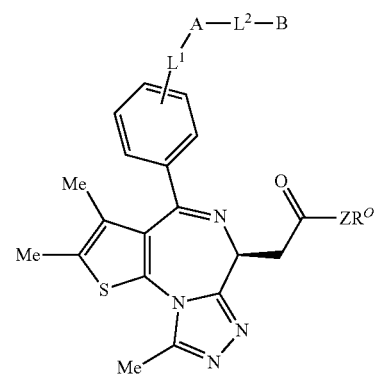

13 Claims, 1 Drawing Sheet

(56) References Cited

U.S. PATENT DOCUMENTS

| | | | |
|---|---|---|---|
| 8,003,786 | B2 | 8/2011 | Hoffmann et al. |
| 8,133,900 | B2 | 3/2012 | Hood et al. |
| 8,138,199 | B2 | 3/2012 | Noronha et al. |
| 8,604,042 | B2 | 12/2013 | Noronha et al. |
| 8,981,083 | B2* | 3/2015 | Bradner ............... C07D 487/04 540/560 |
| 9,301,962 | B2* | 4/2016 | Bradner ............... C07D 495/14 |
| 9,320,741 | B2* | 4/2016 | Bradner ............... C07D 495/14 |
| 2002/0032200 | A1 | 3/2002 | Cai et al. |
| 2003/0216758 | A1 | 11/2003 | Signore |
| 2004/0176380 | A1 | 9/2004 | Hoffmann et al. |
| 2006/0074088 | A1 | 4/2006 | Munzert et al. |
| 2007/0105839 | A1 | 5/2007 | Imbach et al. |
| 2007/0179178 | A1 | 8/2007 | Buettelmann et al. |
| 2009/0238828 | A1 | 9/2009 | Munzert et al. |
| 2009/0280115 | A1 | 11/2009 | Maier et al. |
| 2009/0281191 | A1 | 11/2009 | Rangwala et al. |
| 2010/0041643 | A1 | 2/2010 | Adachi et al. |
| 2010/0249412 | A1 | 9/2010 | Linz et al. |
| 2010/0286127 | A1 | 11/2010 | Miyoshi et al. |
| 2011/0028405 | A1 | 2/2011 | Harrison et al. |
| 2011/0098288 | A1 | 4/2011 | Major et al. |
| 2011/0172231 | A1 | 7/2011 | Baenteli et al. |
| 2011/0201606 | A1 | 8/2011 | Garcia-Echeverria et al. |
| 2011/0212077 | A1 | 9/2011 | Noronha et al. |
| 2011/0245245 | A1 | 10/2011 | Mortensen et al. |
| 2012/0040961 | A1 | 2/2012 | Gray et al. |
| 2012/0329803 | A1 | 12/2012 | Linz et al. |
| 2013/0245013 | A1 | 9/2013 | Mohr et al. |
| 2013/0274239 | A1 | 10/2013 | Gangloff et al. |
| 2016/0033519 | A1 | 2/2016 | Bradner et al. |
| 2016/0332993 | A1 | 11/2016 | Bradner et al. |

FOREIGN PATENT DOCUMENTS

| | | | |
|---|---|---|---|
| WO | WO 2011/054848 | A1 | 5/2011 |
| WO | WO 2011/143669 | A2 | 11/2011 |
| WO | WO 2011/161031 | A1 | 12/2011 |
| WO | WO 2012/075383 | A2 | 6/2012 |
| WO | WO 2012/116170 | A1 | 8/2012 |
| WO | WO 2013/097601 | A1 | 7/2013 |
| WO | WO 2014/071247 | A1 | 5/2014 |

OTHER PUBLICATIONS

International Preliminary Report on Patentability for PCT/US2014/023386, mailed Sep. 24, 2015.
Invitation to Pay Additional Fees for PCT/US2014/48230, mailed Nov. 17, 2014.
International Search Report and Written Opinion for PCT/US2014/48230, mailed Jan. 30, 2015.
International Preliminary Report on Patentability for PCT/US2014/48230, mailed Feb. 4, 2016.
Invitation to Pay Additional Fees for PCT/US2015/14109, mailed Apr. 20, 2015.
International Search Report and Written Opinion for PCT/US2015/14109, mailed Jul. 6, 2015.
International Preliminary Report on Patentability for PCT/US2015/14109, mailed Aug. 11, 2016.
International Search Report and Written Opinion for PCT/US2015/14044, mailed Apr. 23, 2015.
International Preliminary Report on Patentability for PCT/US2015/14044, mailed Aug. 11, 2016.
International Search Report and Written Opinion for PCT/US2015/14039, mailed Apr. 23, 2015.
International Preliminary Report on Patentability for PCT/US2015/14039, mailed Aug. 11, 2016.
International Search Report and Written Opinion for PCT/US2015/14120, mailed Apr. 23, 2015.
International Preliminary Report on Patentability for PCT/US2015/14120, mailed Aug. 11, 2016.
International Search Report and Written Opinion for PCT/US2015/044180, mailed Nov. 5, 2015.
Invitation to Pay Additional Fees for PCT/US2015/44303, mailed Oct. 21, 2015.
International Search Report and Written Opinion for PCT/US2015/44303, mailed Dec. 31, 2015.
Invitation to Pay Additional Fees for PCT/US2016/051017, mailed Oct. 31, 2016.
[No Author Listed], PubChem SID 225027960. Available date/deposit date: Feb. 2, 2015. pubchem.ncbi.nlm.nih.gov/substance/225027960. Last accessed Nov. 28, 2016.
[No Author Listed], PubChem CID 5325760. Published Jan. 25, 2006. pubchem.ncbi.nlm.nih.gov//compound/5325760?from=summary#section=Top. Last accessed Oct. 20, 2014.
Anders et al., Genome-wide localization of small molecules. Nat Biotechnol. Jan. 2014;32(1):92-6. doi: 10.1038/nbt.2776. Epub Dec. 15, 2013.
Bartholomeeusen et al., Bromodomain and extra-terminal (BET) bromodomain inhibition activate transcription via transient release of positive transcription elongation factor b (P-TEFb) from 7SK small nuclear ribonucleoprotein. J Biol Chem. Oct. 19, 2012;287(43):36609-16. doi: 10.1074/jbc.M112.410746. Epub Sep. 5, 2012.
Baud et al., Chemical biology. A bump-and-hole approach to engineer controlled selectivity of BET bromodomain chemical probes. Science. Oct. 31, 2014;346(6209):638-41. doi: 10.1126/science.1249830. Epub Oct. 16, 2014.
Berge et al., Pharmaceutical salts. J Pharm Sci. Jan. 1977;66(1):1-19.
Caplus Database Result for Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013. Accession No. 2013:1979798. Abstract Only.
Chaidos et al., Potent antimyeloma activity of the novel bromodomain inhibitors I-BET151 and I-BET762. Blood. Jan. 30, 2014;123(5):697-705. doi: 10.1182/blood-2013-01-478420. Epub Dec. 13, 2013.
Dawson et al., Inhibition of BET recruitment to chromatin as an effective treatment for MLL-fusion leukaemia. Nature. Oct. 2, 2011;478(7370):529-33. doi: 10.1038/nature10509.
Delmore et al., BET bromodomain inhibition as a therapeutic strategy to target c-Myc. Cell. Sep. 16, 2011;146(6):904-17. doi: 10.1016/j.cell.2011.08.017. Epub Sep. 1, 2011.
Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013.
Filippakopoulos et al., Targeting bromodomains: epigenetic readers of lysine acetylation. Nat Rev Drug Discov. May 2014;13(5):337-56. doi: 10.1038/nrd4286. Epub Apr. 22, 2014.
French et al., BRD4-NUT fusion oncogene: a novel mechanism in aggressive carcinoma. Cancer Res. Jan. 15, 2003;63(2):304-7.
French et al., BRD-NUT oncoproteins: a family of closely related nuclear proteins that block epithelial differentiation and maintain the growth of carcinoma cells. Oncogene. Apr. 3, 2008;27(15):2237-42. Epub Oct. 15, 2007.
Krueger et al., The mechanism of release of P-TEFb and HEXIM1 from the 7SK snRNP by viral and cellular activators includes a conformational change in 7SK. PLoS One. Aug. 23, 2010;5(8):e12335. doi: 10.1371/journal.pone.0012335.
McKeown et al., Biased multicomponent reactions to develop novel bromodomain inhibitors. J Med Chem. Nov. 13, 2014;57(21):9019-27. doi: 10.1021/jm501120z. Epub Oct. 31, 2014.
Roberts et al., A Bead-Based Proximity Assay for BRD4 Ligand Discovery. Curr Protoc Chem Biol. Dec. 2, 2015;7(4):263-78. doi: 10.1002/9780470559277.ch150024.
Schroder et al., Two-pronged binding with bromodomain-containing protein 4 liberates positive transcription elongation factor b from inactive ribonucleoprotein complexes. J Biol Chem. Jan. 6, 2012;287(2):1090-9. doi: 10.1074/jbc.M111.282855. Epub Nov. 14, 2011.

(56) References Cited

OTHER PUBLICATIONS

Smith et al., The Bromodomain: A New Target in Emerging Epigenetic Medicine. ACS Chem Biol. Mar. 18, 2016;11(3):598-608. doi: 10.1021/acschembio.5b00831. Epub Dec. 3, 2015.

Tanaka et al., Inhibitors of emerging epigenetic targets for cancer therapy: a patent review (2010-2014). Pharm Pat Anal. 2015;4(4):261-84. doi: 10.4155/ppa.15.16.

Yang et al., Recruitment of P-TEFb for stimulation of transcriptional elongation by the bromodomain protein Brd4. Mol Cell. Aug. 19, 2005;19(4):535-45.

Zeng et al., Bromodomain: an acetyl-lysine binding domain. FEBS Lett. Feb. 20, 2002;513(1):124-8.

Zuber et al., RNAi screen identifies Brd4 as a therapeutic target in acute myeloid leukaemia. Nature. Aug. 3, 2011;478(7370):524-8. doi: 10.1038/nature10334.

Zuercher et al., Identification and structure-activity relationship of phenolic acyl hydrazones as selective agonists for the estrogen-related orphan nuclear receptors ERRbeta and ERRgamma.. J Med Chem. May 5, 2005;48(9):3107-9.

\* cited by examiner

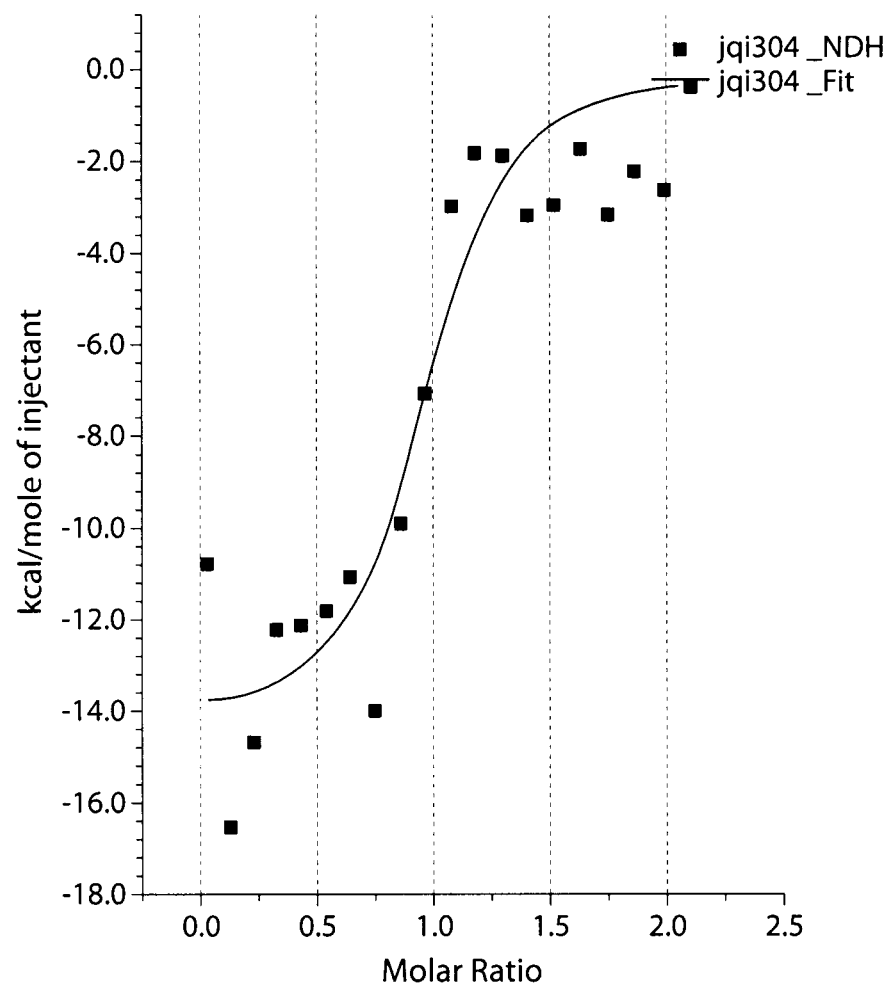

BROMODOMAIN BINDING REAGENTS AND USES THEREOF

RELATED APPLICATIONS

This application is a national stage filing under 35 U.S.C. §371 of international PCT application, PCT/US2014/023386, filed Mar. 11, 2014, which claims priority under 35 U.S.C. §119(e) to U.S. provisional patent application, U.S. Ser. No. 61/781,472, filed Mar. 14, 2013, the entire contents of each of which is incorporated herein by reference.

GOVERNMENT SUPPORT

This invention was made with U.S. Government support under grant number K08 CA128972 awarded by the National Institutes of Health (NIH). The U.S. Government has certain rights in the invention.

BACKGROUND OF THE INVENTION

Histone N-terminal tails maintain chromatin stability and are subject to modifications associated with transcriptional regulation. The best characterized of these modifications are acetylation, methylation, and phosphorylation For each modification, enzymes exist that either lay down the appropriate mark or remove it. These modifications are then interpreted by the transcriptional machinery.

Acetyl-lysine recognition is principally mediated by bromodomains, which are common components of transcription factor complexes. Bromodomain-containing proteins are of substantial biological interest, as components of transcription factor complexes (TAF1, PCAF, Gcn5 and CBP) and determinants of epigenetic memory. There are 41 human proteins containing a total of 57 diverse bromodomains. Despite large sequence variations, all bromodomains share a conserved fold comprising a left-handed bundle of four alpha-helices linked by diverse loop regions (ZA and BC loops) that determine substrate specificity. Co-crystal structures with peptidic substrates showed that the acetyl-lysine is recognized by a central hydrophobic cavity and is anchored by a hydrogen bond with an asparagine residue present in most bromodomains. The bromodomain and extra-terminal (BET)-family (BRD2, BRD3, BRD4, and BRDT) shares a common domain architecture comprising two N-terminal bromodomains that exhibit a high level of sequence conservation and a more divergent C-terminal recruitment domain, which is implicated in protein-protein interactions. Aberrant regulation of histone modification can affect gene activity and play a role in oncogenesis.

Lysine sidechain acetylation is also an important regulatory event in the function of non-histone proteins, including, but not limited to, Hsp90, p53, STAT transcription factors, cortactin, beta-catenin, and alpha-tubulin, and has emerged as a signaling modification of broad relevance to cellular and disease biology. Targeting the enzymes which reversibly mediate side-chain acetylation has been an active area of drug discovery research for many years.

Recent research has established a compelling rationale for targeting BRD4 in cancer. BRD4 functions to facilitate cell cycle progression and knock-down in cultured cancer cell lines prompts G1 arrest. BRD4 is an important mediator of transcriptional elongation, functioning to recruit the positive transcription elongation factor complex (P-TEFb). Cyclin dependent kinase-9, a core component of P-TEFb, is a validated target in chronic lymphocytic leukemia and has recently been linked to c-Myc-dependent transcription. Bromodomains present in BRD4 recruit P-TEFb to mitotic chromosomes resulting in increased expression of growth promoting genes. BRD4 remains bound to transcriptional start sites of genes expressed during M/G1 but has not been found present at start sites that are expressed later in the cell cycle. Knockdown of BRD4 in proliferating cells has been shown to lead to G1 arrest and apoptosis by decreasing expression levels of genes important for mitotic progression and survival.

Most importantly, BRD4 has recently been identified as a component of a recurrent t(15;19) chromosomal translocation in an aggressive form of human squamous carcinoma. Such translocations express the tandem N-terminal bromodomains of BRD4 as an in-frame chimera with the NUT (nuclear protein in testis) protein, genetically defining the so-called NUT midline carcinoma (NMC). Functional studies in patient-derived NMC cell lines have validated the essential role of the BRD4-NUT oncoprotein in maintaining the characteristic proliferation advantage and differentiation block of this uniformly fatal malignancy. Notably, RNA silencing of BRD4-NUT gene expression arrests proliferation and prompts squamous differentiation with a marked increase in cytokeratin expression. Therefore, there is a need to develop reagents bind bromodomains for use in developing agents that bind bromodomains.

SUMMARY OF THE INVENTION

JQ1, depicted below, has been identified as a cell-permeable, potent small-molecule inhibitor with biochemical selectivity for the BET-family of bromodomains. See, for example, PCT Application Publication No. WO 2011/143669.

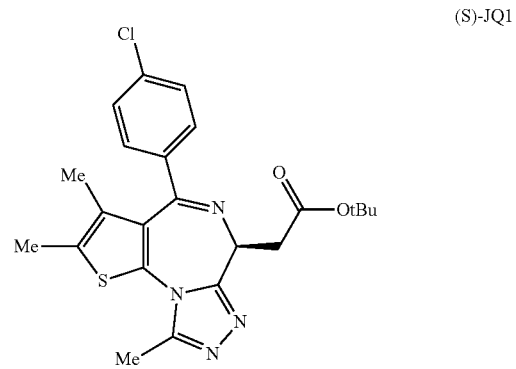 [SMILES: Cc1sc2c(c1C)C(c1ccc(Cl)cc1)=N[C@@H](CC(=O)OC(C)(C)C)c1nnc(C)n1-2]

(S)-JQ1

The present invention provides bromodomain binding reagents based, in part, on the structure of JQ1, which comprise JQ1 conjugated through a linking group to a probe or label. These reagents may be useful in various assays for identifying bromodomain binding agents. The thieondiazapine moiety efficiently binds to bromodomains, especially the bromodomain and extra-terminal (BET) subfamily (including BRD2, BRD3, BRD4, and BRDT). A variety of assays are envisioned using these reagents, such as alpha-assays, surface plasmon resonance (SPR), and microarray. These assays may be used in a high-throughput format for screening and/or evaluating small candidate molecules for drug discovery. The binding affinity of these reagents for the bromodomain in the BET subfamily can be determined by isothermal titration calorimetry (ITC).

In one aspect, provided are compounds of the Formula (I) or (II), which comprise JQ1 conjugated through a linking group to a probe or label:

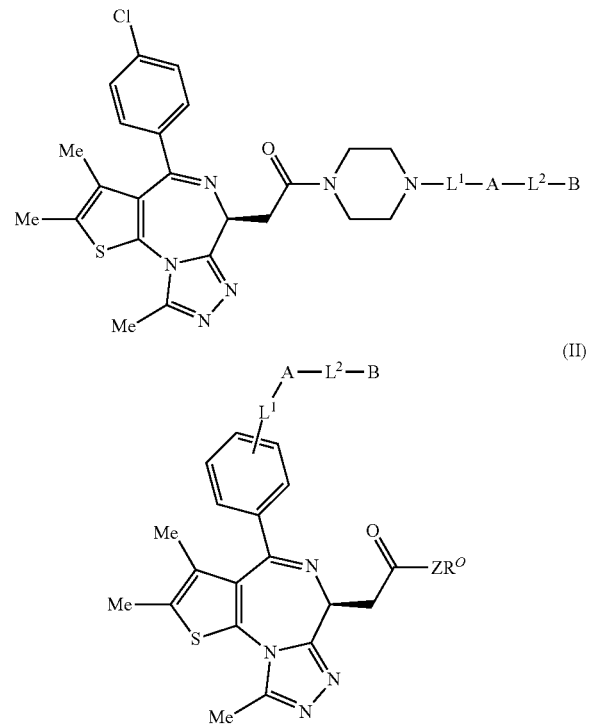

or a salt thereof;
wherein:
Z is O, S, or NR$^O$;
each instance of R$^O$ is independently hydrogen, substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted heterocyclyl; substituted or unsubstituted carbocyclyl; substituted or unsubstituted aryl; substituted or unsubstituted heteroaryl, or a protecting group, or two R$^O$ groups are joined to form a substituted or unsubstituted heterocyclic or heteroaryl group;
L$^1$ is a bond or a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof;
L$^2$ is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof;

A is a bond, —NR$^{W1}$—, —NR$^{W1}$—NR$^{W1}$—, —S—, —O—, —S—S—

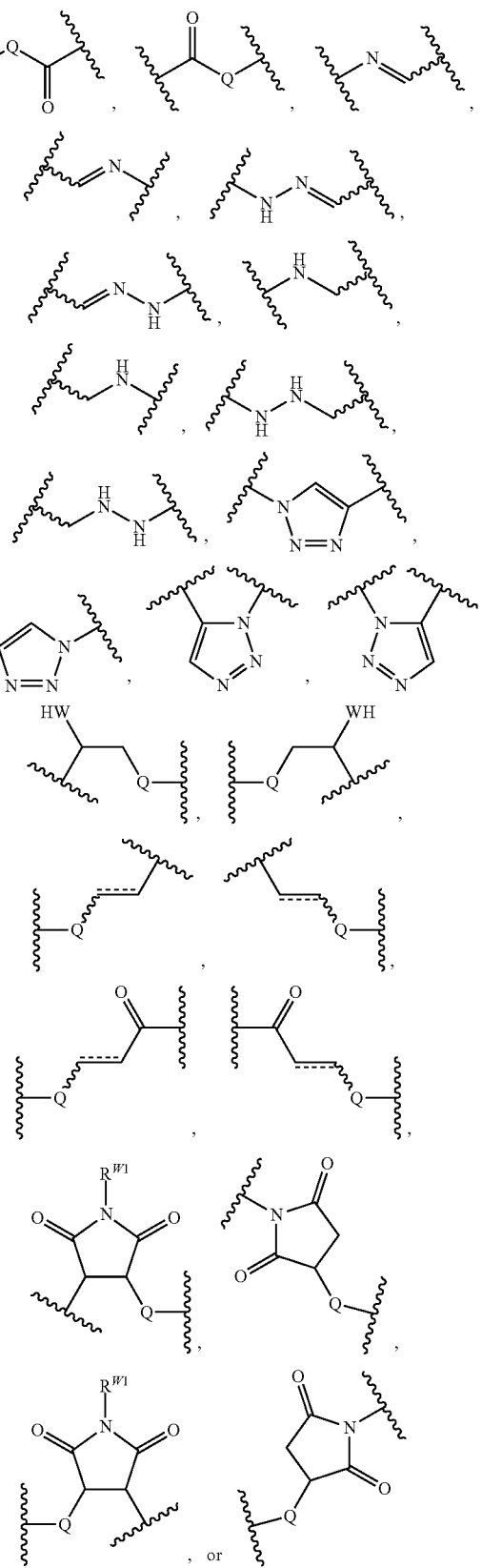

wherein ------ is a single or double bond, W is —O—, —S—, or —NR$^{W1}$—, R$^{W1}$ is hydrogen, substituted or unsubstituted alkyl, or an amino protecting group; and Q is —NR$^{W1}$—, —NR$^{W1}$—NR$^{W1}$—, —S—, —O—; and B is a label or probe.

In certain embodiments, B is biotin, and the compound of Formula (I) and (II) is of the formula:

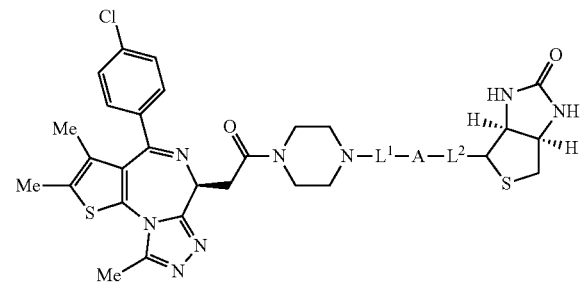

(I-biotin)

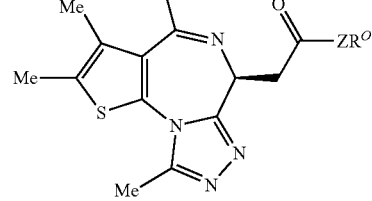

(II-biotin)

or a salt thereof.

In certain embodiments, B is fluorescein isothiocyanate (FITC) and the compound of Formula (I) and (II) is of the formula:

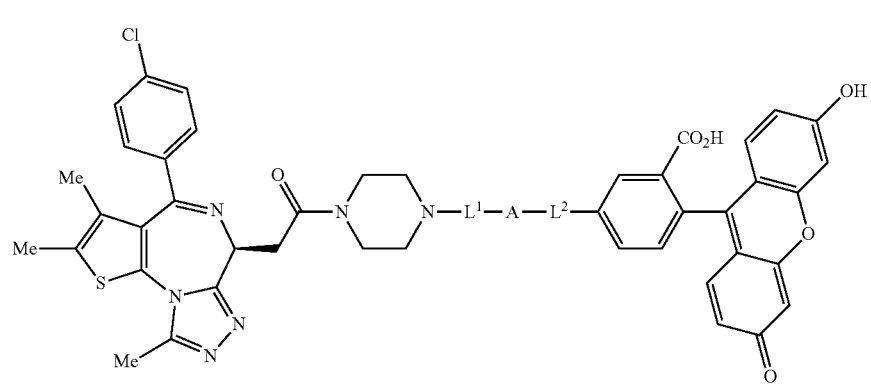

(I-FITC)

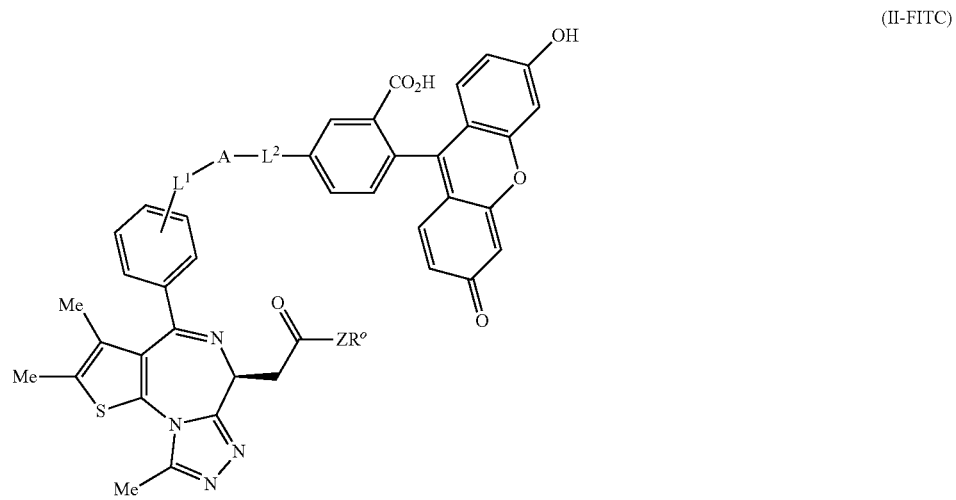

(II-FITC)

or a salt thereof.

In certain embodiments, the compound of Formula (I) is of the formula:

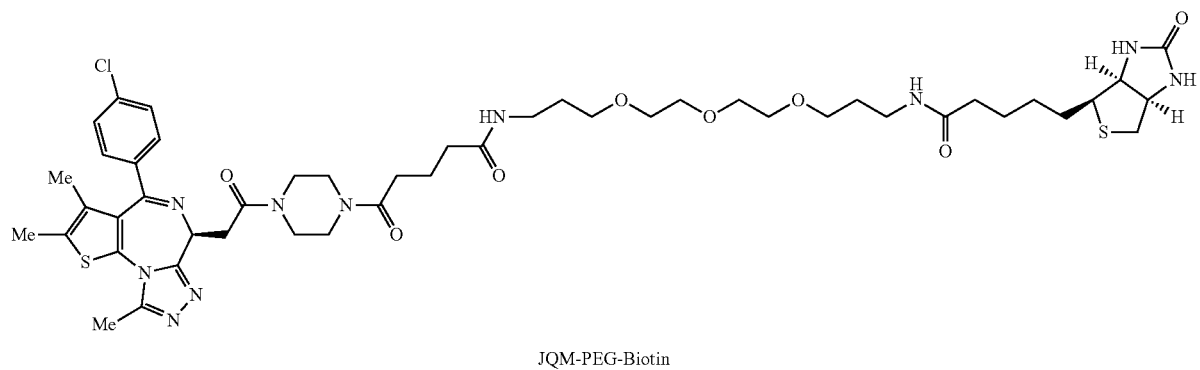 [SMILES: Cc1sc2c(c1C)C(c1ccc(Cl)cc1)=N[C@@H](CC(=O)N1CCN(C(=O)CCCC(=O)NCCCOCCOCCOCCCNC(=O)CCCC[C@@H]3SC[C@@H]4NC(=O)N[C@@H]43)CC1)c1nnc(C)n1-2]

JQM-PEG-Biotin or salt thereof.

Synthetic intermediates and methods for the preparation of such probes are further contemplated herein. For example, in another aspect, provided are synthetic intermediates of compounds of Formula (I) and (II), referred to herein as precursor compounds of Formula (P-I) and (P-II), respectively:

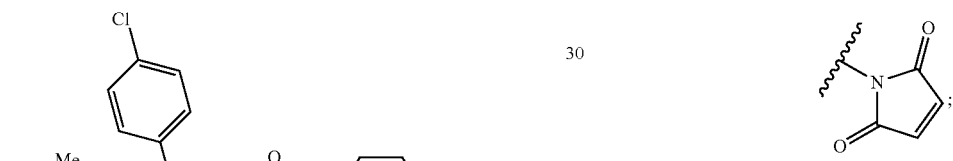

or a salt thereof; wherein $L^1$ is as defined herein; and

X is selected from the group consisting of —SH, —OH, —NH$_2$, —NH—NH$_2$, —N$_3$, halogen, —C(=O)R$^{Z1}$,

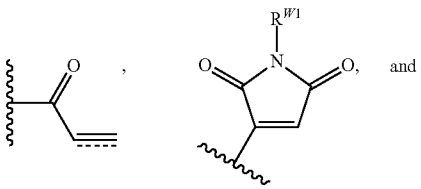

wherein:

≡ represents a double or triple bond;

$R^{Z1}$ is hydrogen, halogen, or —OR$^{Z2}$, wherein $R^{Z2}$ is hydrogen, substituted or unsubstituted alkyl, or an oxygen protecting group;

W is —O—, —S—, or —NR$^{W1}$—, wherein $R^{W1}$ is hydrogen, substituted or unsubstituted alkyl, or a nitrogen protecting group;

provided the group -L$^1$-X of Formula (P-I) is not —CH$_2$CH$_2$OH.

In certain embodiments, the compound of Formula (P-I) is selected from the group consisting of:

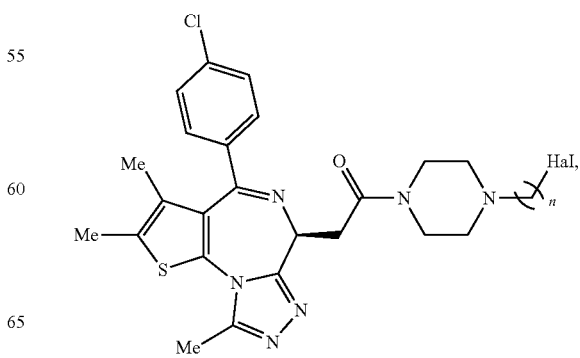

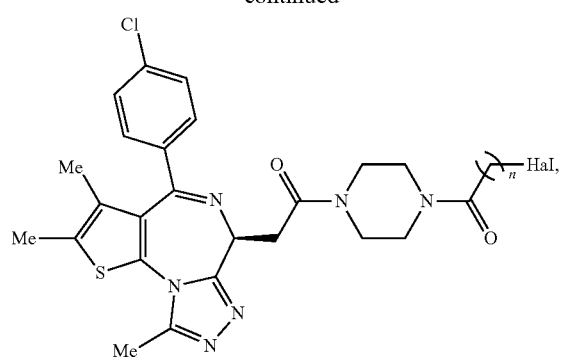
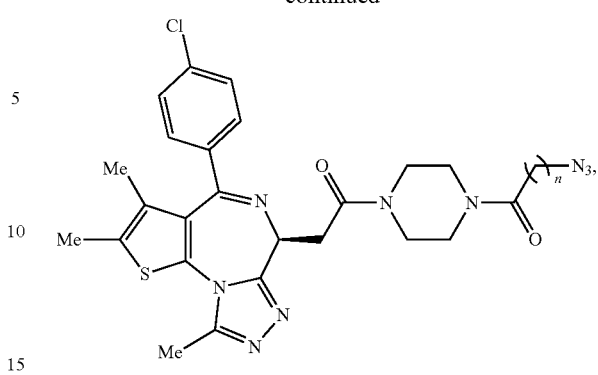
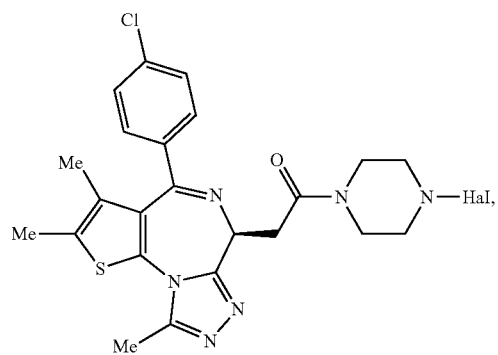
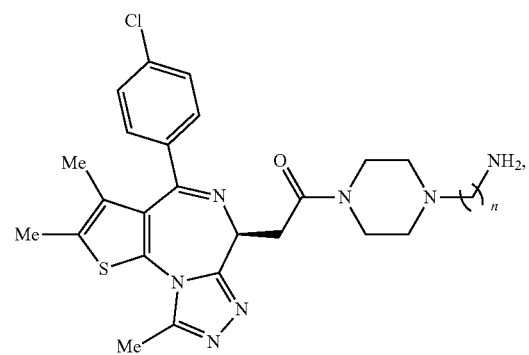
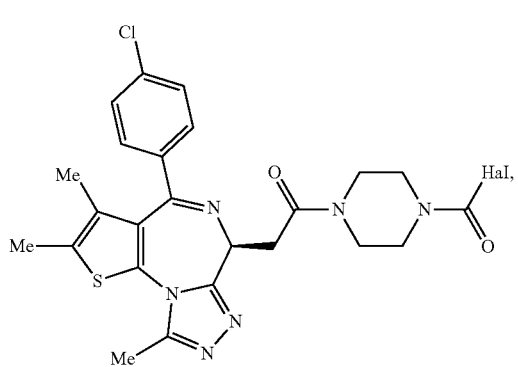
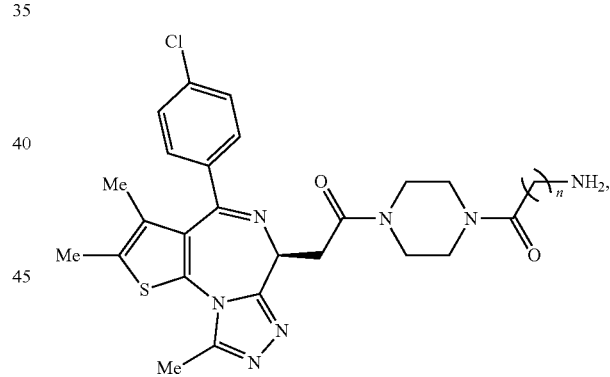
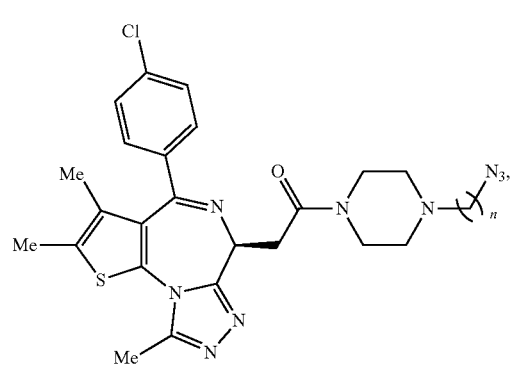
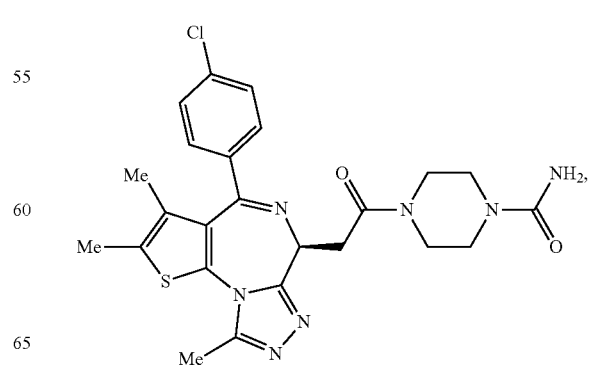

11
-continued
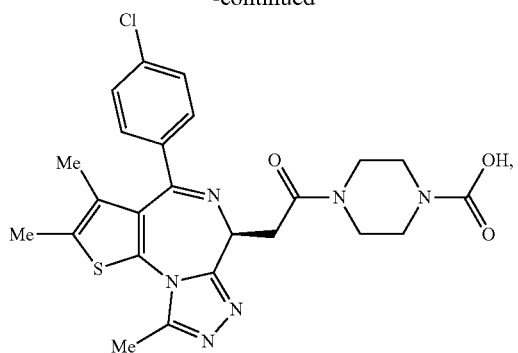
12
-continued
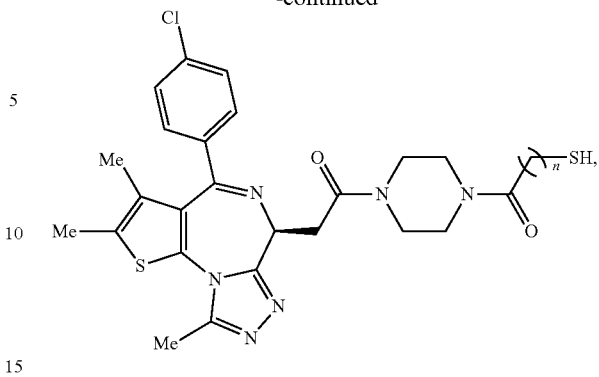
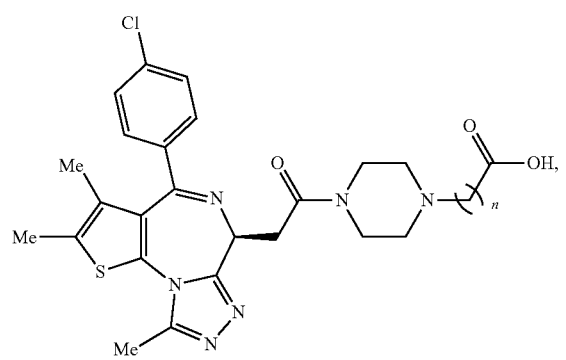
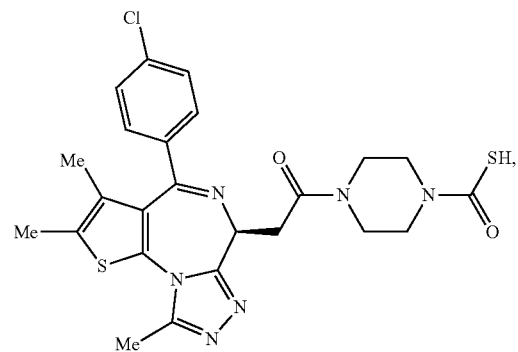
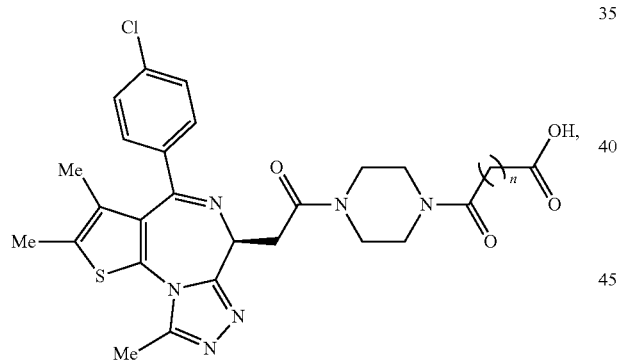
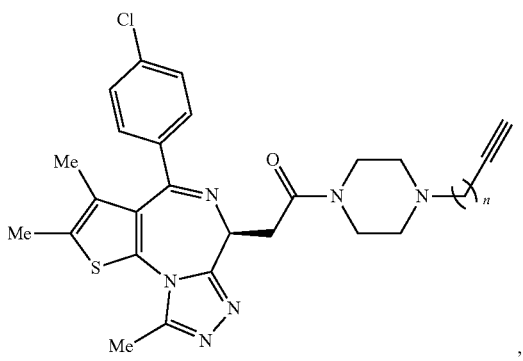
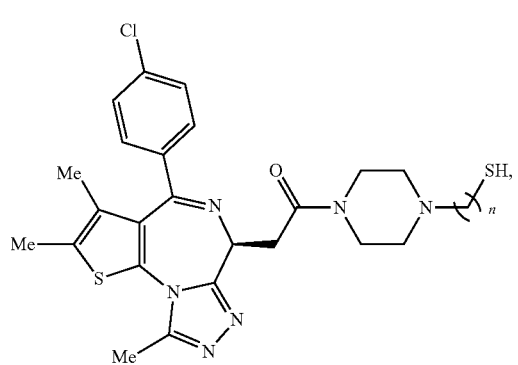
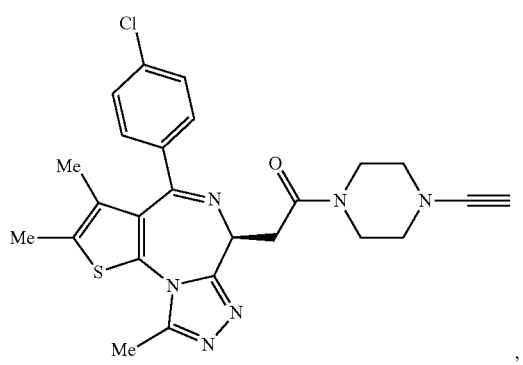

-continued
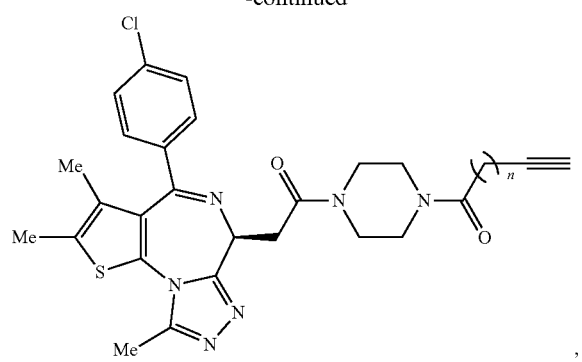
,
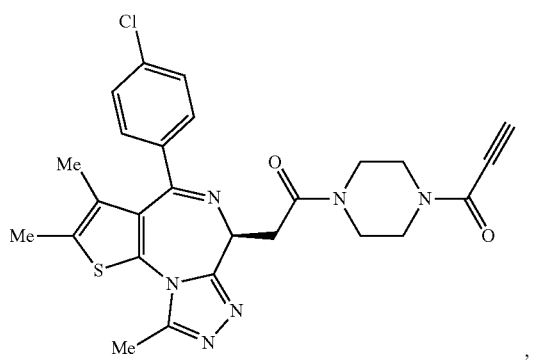
,
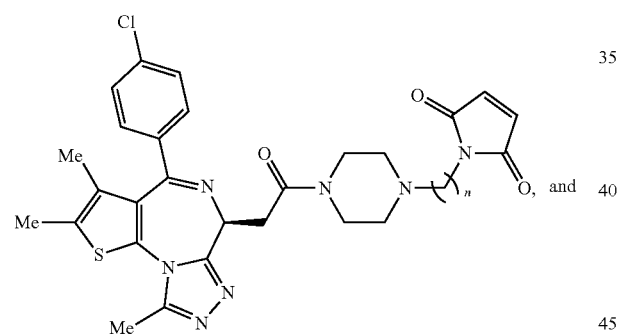
, and
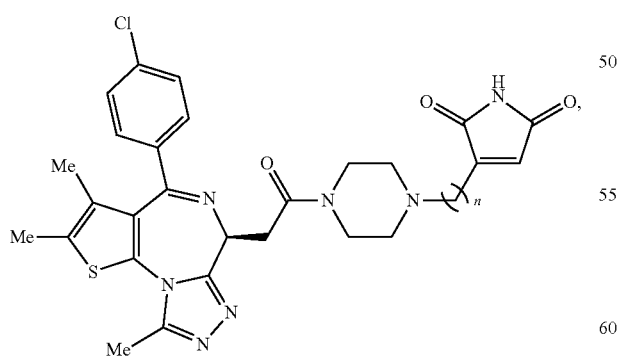
and salts thereof, wherein n is 0 or an integer between 1 and 10, inclusive; and Hal is —Cl, —Br, or —I.
In certain embodiments, the compound of Formula (P-II) is selected from the group consisting of:
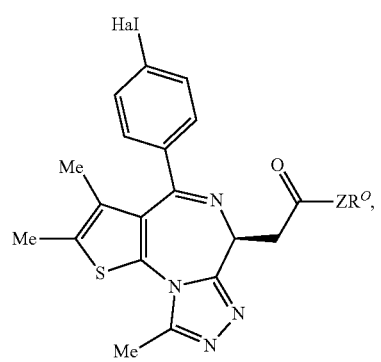
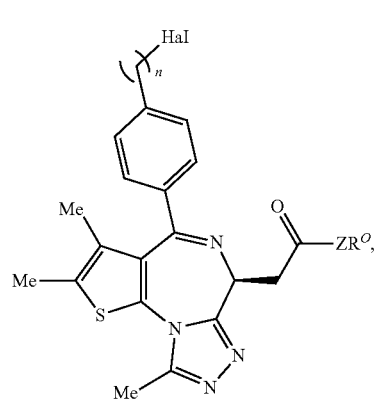
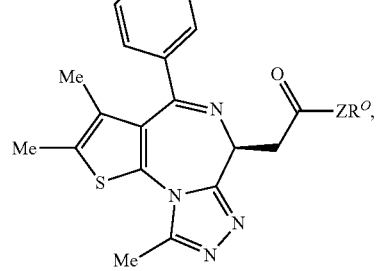
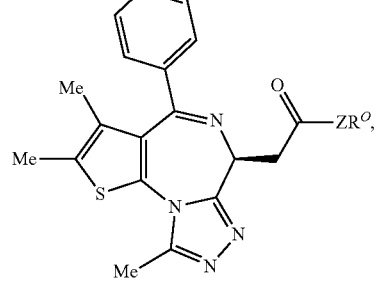

-continued
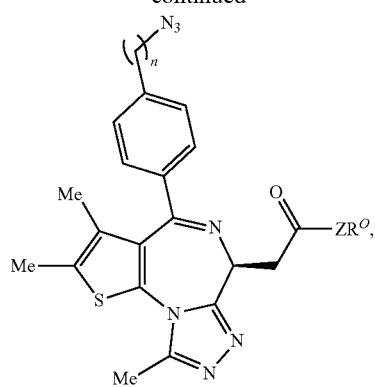
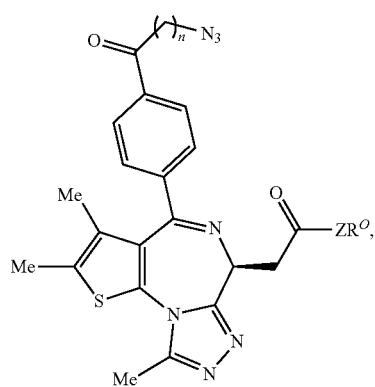
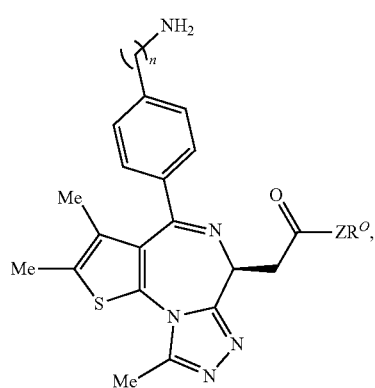
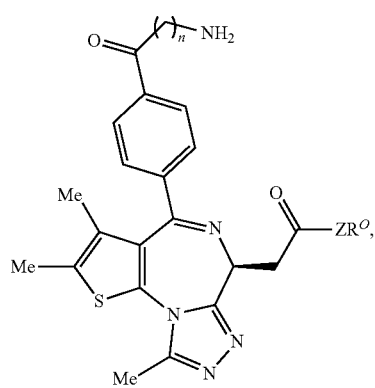
-continued
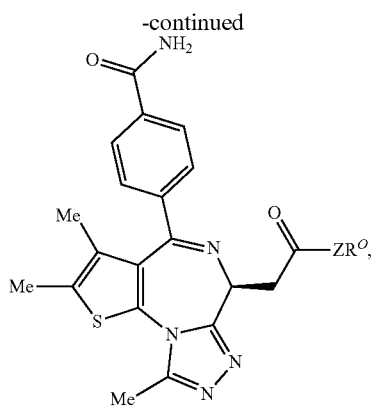
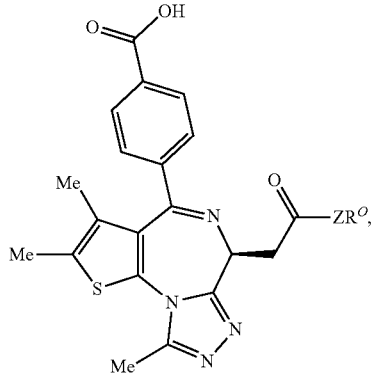
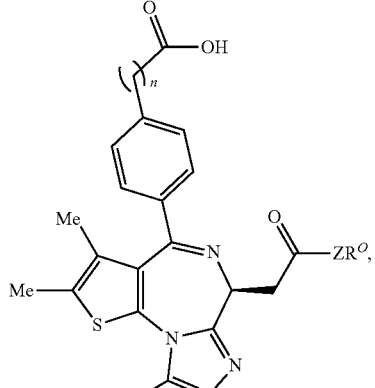
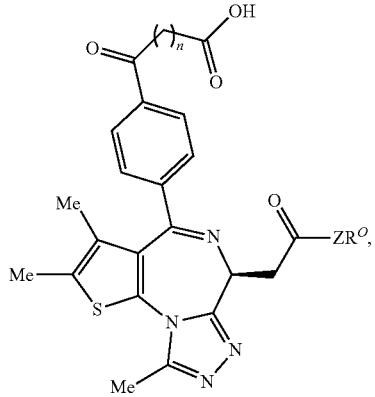

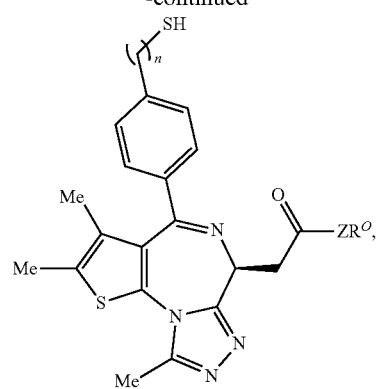
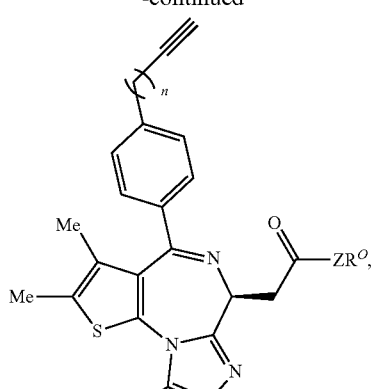
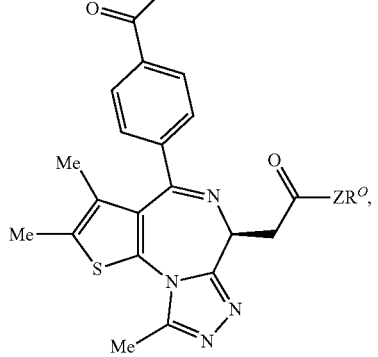
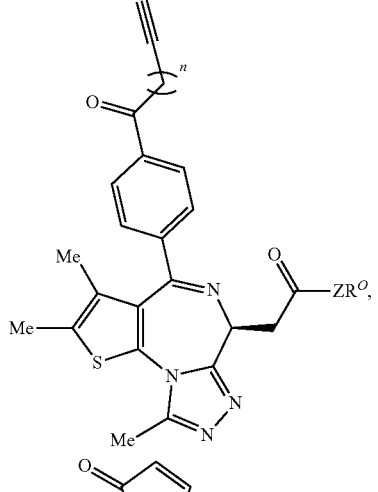
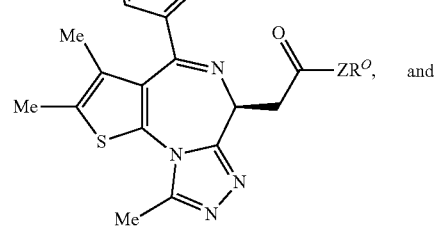

-continued

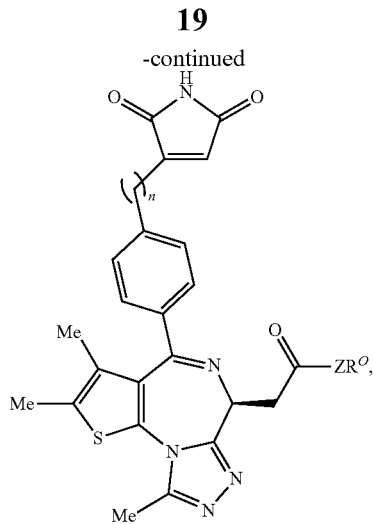

and salts thereof, wherein n is 0 or an integer between 1 and 10, inclusive; and Hal is —Cl, —Br, or —I.

Methods of preparing the compounds of Formula (I), (II), (P-I), or (P-II) are also provided. For example, in certain aspects, the compound of Formula (I) or (II) is prepared by coupling of a precursor compound of Formula (P-I) or (P-II) with a compound of Formula (P-III), Y-L$^2$-B, wherein X and Y react to form a group A. Exemplary coupling reactions include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; and maleimide addition, between a precursor compound of Formula (P-I) or (P-II) with a compound of Formula (P-III), Y-L$^2$-B. In certain embodiments, the coupling reaction utilizes "click" chemistry.

Further provided are kits comprising one or more compounds of Formula (I), (II), (P-I), or (P-II) are also provided, e.g., for use in an assay.

The details of one or more embodiments of the invention are set forth in the Detailed Description of Certain Embodiments, as described below. Other features, objects, and advantages of the invention will be apparent from the Definitions, Examples, and Claims.

BRIEF DESCRIPTION OF THE DRAWING

The FIGURE depicts the ITC of JQM-PEG-Biotin binding to BRD4.

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_4$-5, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —CH$_3$). In certain embodiments, the alkyl group is a substituted $C_{1-10}$ alkyl.

As used herein, "perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) the parent chain. In other words, a heteroalkyl group refers to a saturated group having from 1 to 10 carbon atoms and 1, 2, 3, or 4 heteroatoms within the parent chain ("hetero$C_{1-10}$ alkyl"). In some embodiments, a heteroalkyl group is a saturated group having 1 to 9 carbon atoms and 1, 2, 3, or 4 heteroatoms within the parent chain ("hetero$C_{1-9}$ alkyl"). In some embodiments, a heteroalkyl group is a saturated group having 1 to 8 carbon atoms and 1, 2, 3, or 4 heteroatoms within the parent chain ("hetero$C_{1-8}$ alkyl"). In some embodiments, a heteroalkyl group is a saturated group having 1 to 7 carbon atoms and 1, 2, 3, or 4 heteroatoms within the parent chain ("hetero$C_{1-7}$ alkyl"). In some embodiments, a heteroalkyl group is a saturated group having 1 to 6 carbon atoms and 1, 2, or 3 heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) the parent chain. In other words, a heteroalkenyl group refers to a group having from 2 to 10 carbon atoms, at least one double bond, and 1, 2, 3, or 4 heteroatoms within the parent chain ("hetero$C_{2-10}$ alkenyl"). In some embodiments, a heteroalkenyl group has 2 to 9 carbon atoms at least one double bond, and 1, 2, 3, or 4 heteroatoms within the parent chain ("hetero$C_{2-9}$ alkenyl"). In some embodiments, a heteroalkenyl group has 2 to 8 carbon atoms, at least one double bond, and 1, 2, 3, or 4 heteroatoms within the parent chain ("hetero$C_{2-8}$ alkenyl"). In some embodiments, a heteroalkenyl group has 2 to 7 carbon atoms, at least one double bond, and 1, 2, 3, or 4 heteroatoms within the parent chain ("hetero$C_{2-7}$ alkenyl"). In some embodiments, a heteroalkenyl group has 2 to 6 carbon atoms, at least one double bond, and 1, 2, or 3 heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) the parent chain. In other words, a heteroalkynyl group refers to a group having from 2 to 10 carbon atoms, at least one triple bond, and 1, 2, 3, or 4 heteroatoms within the parent chain ("hetero$C_{2-10}$ alkynyl"). In some embodiments, a heteroalkynyl group has 2 to 9 carbon atoms, at least one triple bond, and 1, 2, 3, or 4 heteroatoms within the parent chain ("hetero$C_{2-9}$ alkynyl"). In some embodiments, a heteroalkynyl group has 2 to 8 carbon atoms, at least one triple bond, and 1, 2, 3, or 4 heteroatoms within the parent chain ("hetero$C_{2-8}$ alkynyl"). In some embodiments, a heteroalkynyl group has 2 to 7 carbon atoms, at least one triple bond, and 1, 2, 3, or 4 heteroatoms within the parent chain ("hetero$C_{2-7}$ alkynyl"). In some embodiments, a heteroalkynyl group has 2 to 6 carbon atoms, at least one triple bond, and 1, 2, or 3 heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_5$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

Alkyl, alkenyl, alkynyl, heteroalkyl, heteroalkenyl, heteroalkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O) OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O) (NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$heteroalkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$heteroalkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, $C_{6}$-10 aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$, —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{1-6}$heteroalkyl, $C_{2-6}$ heteroalkenyl, $C_{2-6}$ heteroalkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=NR$^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)

$(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, $-OH$, $-OR^{aa}$, $-N(R^{cc})_2$, $-C(=O)R^{aa}$, $-C(=O)N(R^{cc})_2$, $-CO_2R^{aa}$, $-SO_2R^{aa}$, $-C(=NR^{cc})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., $-C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., $-C(=O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9- phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, alkyl 2,2,2-trichloroethyl carbonate (Troc), t-butyl carbonate (Boc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, p-nitrophenyl carbonate, benzyl carbonate, p-methoxybenzyl carbonate, alkyl 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

As used herein, the term "salt" refers to any and all salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

DETAILED DESCRIPTION OF CERTAIN EMBODIMENTS OF THE INVENTION

As generally described herein, the present invention provides compounds of Formula (I) and (II) and precursor compounds of Formula (P-I) and (P-2). Such compounds are based on the structure of the BET bromodomain inhibitor JQ1. The present invention also provides use of these new probes in various assays, e.g., such as a displacement assay useful in evaluating binding of a test compound to a bromodomain containing protein, also, assay and kits for the assay. Methods for the preparation of such probes are further contemplated herein.

Compounds of Formula (I) and (II)

In one aspect, provided are compounds of the Formula (I) or (II), which comprise JQ1 conjugated through a linking group to a probe or label:

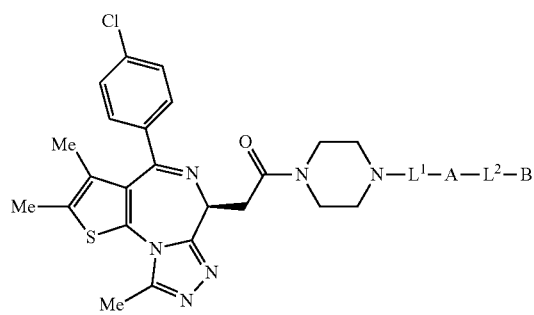

(I)

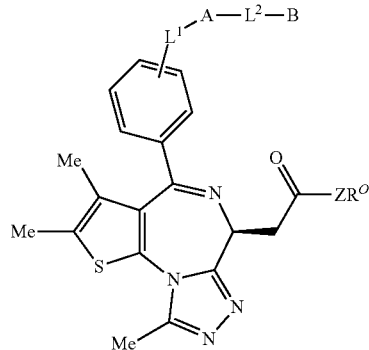

(II)

or a salt thereof;
wherein:
Z is O, S, or $NR^O$;
each instance of $R^O$ is independently hydrogen, substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted heterocyclyl; substituted or unsubstituted carbocyclyl; substituted or unsubstituted aryl; substituted or unsubstituted heteroaryl, or a protecting group, or two $R^O$ groups are joined to form a substituted or unsubstituted heterocyclic or heteroaryl group;

$L^1$ is a bond or a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof;

$L^2$ is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof;

A is a bond, $-NR^{W1}-$, $-NR^{W1}-NR^{W1}-$, $-S-$, $-O-$, $-S-S-$,

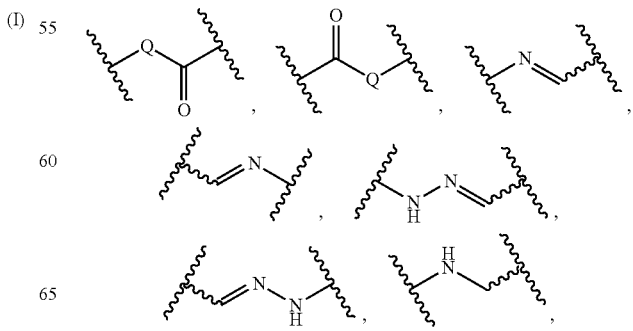

-continued

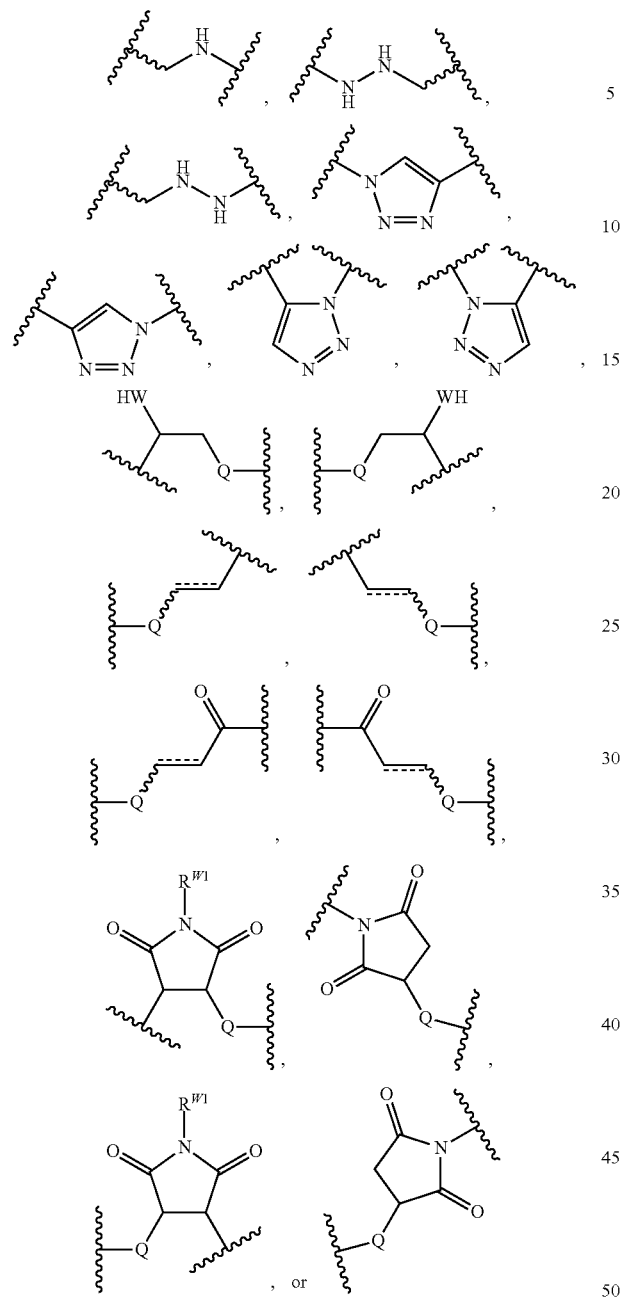

wherein ===== is a single or double bond, W is —O—, —S—, or —NR$^{W1}$—, R$^{W1}$ is hydrogen, substituted or unsubstituted alkyl, or an amino protection group; and Q is —NH—, —NH—NH—, —S—, —O—; and B is a label or probe.

In certain embodiments, the compound is of Formula (I) or a salt thereof.

In certain embodiments, the compound is of Formula (II) or a salt thereof. In certain embodiments, the group -L$^1$-A-L$^2$-B of the compound of Formula (II) is attached to the ortho, meta, or para position of the phenyl ring relative to the diazepine point of attachment, i.e., to provide a compound of Formula (II-a), (II-b), or (II-c) respectively:

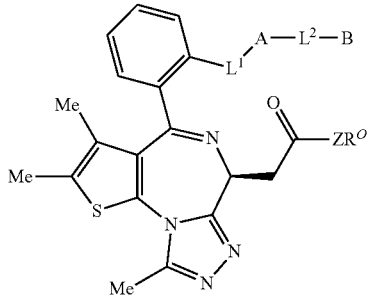

(II-a)

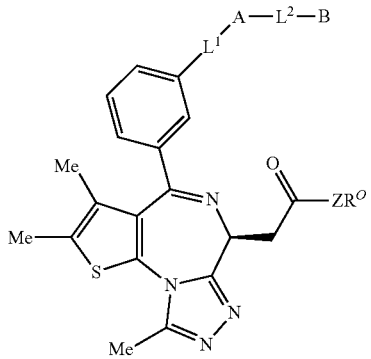

(II-b)

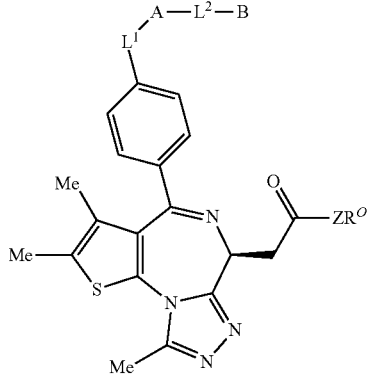

(II-c)

or a salt thereof.

In certain embodiments, the compound of Formula (II) or salt thereof is a compound of Formula (II-c) or salt thereof.

As generally defined herein, each instance of R$^O$ is independently hydrogen, substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted heterocyclyl; substituted or unsubstituted carbocyclyl; substituted or unsubstituted aryl; substituted or unsubstituted heteroaryl, or a protecting group, or two R$^O$ groups are joined to form a substituted or unsubstituted heterocyclic or heteroaryl group.

In certain embodiments, at least one instance of R$^O$ is hydrogen. However, in certain embodiments, R$^O$ is not hydrogen.

In certain embodiments, at least one instance of R$^O$ is substituted or unsubstituted alkyl, e.g., substituted or unsubstituted $C_{1-6}$alkyl, substituted or unsubstituted $C_{2-6}$alkylene, substituted or unsubstituted $C_{3-6}$alkyl, substituted or unsubstituted $C_{4-6}$alkyl, substituted or unsubstituted $C_{5-6}$alkyl, substituted or unsubstituted $C_{2-5}$alkyl, substituted or unsubstituted $C_{2-4}$alkyl, substituted or unsubstituted $C_{2-3}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^O$ is methyl, ethyl, propyl, isopropyl, sec-butyl, iso-butyl, or tert-butyl. In certain embodiments, $R^O$ is isopropyl, sec-butyl, iso-butyl, or tert-butyl. In certain embodiments, $R^O$ is tert-butyl.

In certain embodiments, at least one instance of $R^O$ is substituted or unsubstituted alkenyl, e.g., substituted or unsubstituted $C_{2-6}$alkenyl, substituted or unsubstituted $C_{3-6}$alkenyl, substituted or unsubstituted $C_{4-6}$alkenyl, substituted or unsubstituted $C_{5-6}$alkenyl, substituted or unsubstituted $C_{2-5}$alkenyl, substituted or unsubstituted $C_{2-4}$alkenyl, substituted or unsubstituted $C_{2-3}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl.

In certain embodiments, at least one instance of $R^O$ is substituted or unsubstituted alkynyl, e.g., substituted or unsubstituted $C_{2-6}$alkynyl, substituted or unsubstituted $C_{3-6}$alkynyl, substituted or unsubstituted $C_{4-6}$alkynyl, substituted or unsubstituted $C_{5-6}$alkynyl, substituted or unsubstituted $C_{2-5}$alkynyl, substituted or unsubstituted $C_{2-4}$alkynyl, substituted or unsubstituted $C_{2-3}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments, at least one instance of $R^O$ is substituted or unsubstituted heteroalkyl, e.g., substituted or unsubstituted hetero$C_{1-6}$alkyl, substituted or unsubstituted hetero$C_{2-6}$alkylene, substituted or unsubstituted hetero$C_{3-6}$alkyl, substituted or unsubstituted hetero$C_{4-6}$alkyl, substituted or unsubstituted hetero$C_{5-6}$alkyl, substituted or unsubstituted hetero$C_{2-5}$alkyl, substituted or unsubstituted hetero$C_{2-4}$alkyl, substituted or unsubstituted hetero$C_{2-3}$alkyl, substituted or unsubstituted hetero$C_1$alkyl, substituted or unsubstituted hetero$C_2$alkyl, substituted or unsubstituted hetero$C_3$alkyl, substituted or unsubstituted hetero$C_4$alkyl, substituted or unsubstituted hetero$C_5$alkyl, or substituted or unsubstituted hetero$C_6$alkyl.

In certain embodiments, at least one instance of $R^O$ is substituted or unsubstituted alkenyl, e.g., substituted or unsubstituted hetero$C_{2-6}$alkenyl, substituted or unsubstituted hetero$C_{3-6}$alkenyl, substituted or unsubstituted hetero$C_{4-6}$alkenyl, substituted or unsubstituted hetero$C_{5-6}$alkenyl, substituted or unsubstituted hetero$C_{2-5}$alkenyl, substituted or unsubstituted hetero$C_{2-4}$alkenyl, substituted or unsubstituted hetero$C_{2-3}$alkenyl, substituted or unsubstituted hetero$C_2$alkenyl, substituted or unsubstituted hetero$C_3$alkenyl, substituted or unsubstituted hetero$C_4$alkenyl, substituted or unsubstituted hetero$C_5$alkenyl, or substituted or unsubstituted hetero$C_6$alkenyl.

In certain embodiments, at least one instance of $R^O$ is substituted or unsubstituted alkynyl, e.g., substituted or unsubstituted hetero$C_{2-6}$alkynyl, substituted or unsubstituted hetero$C_{3-6}$alkynyl, substituted or unsubstituted hetero$C_{4-6}$alkynyl, substituted or unsubstituted hetero$C_{5-6}$alkynyl, substituted or unsubstituted hetero$C_{2-5}$alkynyl, substituted or unsubstituted hetero$C_{2-4}$alkynyl, substituted or unsubstituted hetero$C_{2-3}$alkynyl, substituted or unsubstituted hetero$C_2$alkynyl, substituted or unsubstituted hetero$C_3$alkynyl, substituted or unsubstituted hetero$C_4$alkynyl, substituted or unsubstituted hetero$C_5$alkynyl, or substituted or unsubstituted hetero$C_6$alkynyl.

In certain embodiments, at least one instance of $R^O$ is substituted or unsubstituted heterocyclyl, e.g., substituted or unsubstituted 5- to 8-membered heterocyclyl, substituted or unsubstituted 5- to 7-membered heterocyclylheterocyclyl, substituted or unsubstituted 5- to 6-membered heterocyclene, substituted or unsubstituted 5-membered heterocyclyl, substituted or unsubstituted 6-membered heterocyclene, substituted or unsubstituted 7-membered heterocyclyl, or substituted or unsubstituted 8-membered heterocyclyl.

In certain embodiments, at least one instance of $R^O$ is substituted or unsubstituted carbocyclyl, e.g., substituted or unsubstituted $C_{3-6}$ carbocyclyl, substituted or unsubstituted $C_{3-5}$ carbocyclyl, substituted or unsubstituted $C_{3-4}$ carbocyclyl, substituted or unsubstituted $C_3$ carbocyclyl, substituted or unsubstituted $C_4$ carbocyclyl, substituted or unsubstituted $C_5$ carbocyclyl, or substituted or unsubstituted $C_6$ carbocyclyl.

In certain embodiments, at least one instance of $R^O$ is substituted or unsubstituted aryl, e.g., substituted or unsubstituted $C_6$ aryl (phenylene) or substituted or unsubstituted $C_{10}$ aryl (naphthylene).

In certain embodiments, at least one instance of $R^O$ is substituted or unsubstituted heteroaryl, e.g., substituted or unsubstituted 5-membered heteroaryl or substituted or unsubstituted 6-membered heteroaryl.

In certain embodiments, at least one instance of $R^O$ is a protecting group, e.g., an oxygen, nitrogen, or sulfur protecting group, as defined herein.

In certain embodiments, two $R^O$ groups (i.e., attached to the nitrogen atom, —N$R^O R^O$) are joined to form a substituted or unsubstituted heterocyclic or heteroaryl group.

As used herein in reference to linking groups $L^1$ and $L^2$, a "combination thereof" refers to any combination of one or more substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene groups (e.g., 1, 2, 3, 4, or 5 groups) covalently linked to each other, e.g., making up the entire linking group. For example, in certain embodiments, the linking group comprises a substituted or unsubstituted heteroalkylene group covalently attached to a substituted or unsubstituted alkylene group. Any combination of the above groups are contemplated.

As generally defined above, $L^1$ is a bond or a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof.

In certain embodiments, $L^1$ is a bond.

In certain embodiments, $L^1$ is a linking group comprising at least one instance of substituted or unsubstituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^1$ is a substituted or unsubstituted alkylene as defined above and herein.

In certain embodiments, $L^1$ is a linking group comprising at least one instance of substituted or unsubstituted alkenylene, e.g., substituted or unsubstituted $C_{2-6}$alkenylene, substituted or unsubstituted $C_{3-6}$alkenylene, substituted or unsubstituted $C_{4-6}$alkenylene, substituted or unsubstituted $C_{5-6}$alkenylene, substituted or unsubstituted $C_{2-5}$alkenylene, substituted or unsubstituted $C_{2-4}$alkenylene, substituted or unsubstituted $C_{2-3}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene. In certain embodiments, $L^1$ is a substituted or unsubstituted alkenylene as defined above and herein.

In certain embodiments, $L^1$ is a linking group comprising at least one instance of substituted or unsubstituted alkynylene, e.g., substituted or unsubstituted $C_{2-6}$alkynylene, substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene. In certain embodiments, $L^1$ is a substituted or unsubstituted alkynylene as defined above and herein.

In certain embodiments, $L^1$ is a linking group comprising at least one instance of substituted or unsubstituted heteroalkylene, e.g., substituted or unsubstituted hetero$C_{1-6}$alkylene, substituted or unsubstituted hetero$C_{2-6}$alkylene, substituted or unsubstituted hetero$C_{3-6}$alkylene, substituted or unsubstituted hetero$C_{4-6}$alkylene, substituted or unsubstituted hetero$C_{5-6}$alkylene, substituted or unsubstituted hetero$C_{2-5}$alkylene, substituted or unsubstituted hetero$C_{2-4}$alkylene, substituted or unsubstituted hetero$C_{2-3}$alkylene, substituted or unsubstituted hetero$C_1$alkylene, substituted or unsubstituted hetero$C_2$alkylene, substituted or unsubstituted hetero$C_3$alkylene, substituted or unsubstituted hetero$C_4$alkylene, substituted or unsubstituted hetero$C_5$alkylene, or substituted or unsubstituted hetero$C_6$alkylene. In certain embodiments, $L^1$ is a substituted or unsubstituted heteroalkylene as defined above and herein.

In certain embodiments, $L^1$ is a linking group comprising at least one instance of substituted or unsubstituted heteroalkenylene, e.g., substituted or unsubstituted hetero$C_{2-6}$alkenylene, substituted or unsubstituted hetero$C_{3-6}$alkenylene, substituted or unsubstituted hetero$C_{4-6}$alkenylene, substituted or unsubstituted hetero$C_{5-6}$alkenylene, substituted or unsubstituted hetero$C_{2-5}$alkenylene, substituted or unsubstituted hetero$C_{2-4}$alkenylene, substituted or unsubstituted hetero$C_{2-3}$alkenylene, substituted or unsubstituted hetero$C_2$alkenylene, substituted or unsubstituted hetero$C_3$alkenylene, substituted or unsubstituted hetero$C_4$alkenylene, substituted or unsubstituted hetero$C_5$alkenylene, or substituted or unsubstituted hetero$C_6$alkenylene. In certain embodiments, $L^1$ is a substituted or unsubstituted heteroalkenylene as defined above and herein.

In certain embodiments, $L^1$ is a linking group comprising at least one instance of substituted or unsubstituted heteroalkynylene, e.g., substituted or unsubstituted hetero$C_{2-6}$alkynylene, substituted or unsubstituted hetero$C_{3-6}$alkynylene, substituted or unsubstituted hetero$C_{4-6}$alkynylene, substituted or unsubstituted hetero$C_{5-6}$alkynylene, substituted or unsubstituted hetero$C_{2-5}$alkynylene, substituted or unsubstituted hetero$C_{2-4}$alkynylene, substituted or unsubstituted hetero$C_{2-3}$alkynylene, substituted or unsubstituted hetero$C_2$alkynylene, substituted or unsubstituted hetero$C_3$alkynylene, substituted or unsubstituted hetero$C_4$alkynylene, substituted or unsubstituted hetero$C_5$alkynylene, or substituted or unsubstituted hetero$C_6$alkynylene. In certain embodiments, $L^1$ is a substituted or unsubstituted heteroalkynylene as defined above and herein.

In certain embodiments, $L^1$ is a linking group comprising at least one instance of substituted or unsubstituted heterocyclylene, e.g., substituted or unsubstituted 5- to 8-membered heterocyclylene, substituted or unsubstituted 5- to 7-membered heterocyclylene, substituted or unsubstituted 5- to 6-membered heterocyclylene, substituted or unsubstituted 5-membered heterocyclylene, substituted or unsubstituted 6-membered heterocyclylene, substituted or unsubstituted 7-membered heterocyclylene, or substituted or unsubstituted 8-membered heterocyclylene. In certain embodiments, $L^1$ is a substituted or unsubstituted heterocyclylene as defined above and herein.

In certain embodiments, $L^1$ is a linking group comprising at least one instance of substituted or unsubstituted carbocyclylene, e.g., substituted or unsubstituted $C_{3-6}$ carbocyclylene, substituted or unsubstituted $C_{3-5}$ carbocyclylene, substituted or unsubstituted $C_{3-4}$ carbocyclylene, substituted or unsubstituted $C_3$ carbocyclylene, substituted or unsubstituted $C_4$ carbocyclylene, substituted or unsubstituted $C_5$ carbocyclylene, or substituted or unsubstituted $C_6$ carbocyclylene. In certain embodiments, $L^1$ is a substituted or unsubstituted carbocyclylene as defined above and herein.

In certain embodiments, $L^1$ is a linking group comprising at least one instance of substituted or unsubstituted arylene, e.g., substituted or unsubstituted $C_6$ arylene (phenylene) or substituted or unsubstituted $C_{10}$ arylene (naphthylene). In certain embodiments, $L^1$ is a substituted or unsubstituted arylene as defined above and herein.

In certain embodiments, $L^1$ is a linking group comprising at least one instance of substituted or unsubstituted heteroarylene, e.g., substituted or unsubstituted 5-membered heteroarylene or substituted or unsubstituted 6-membered heteroarylene. In certain embodiments, $L^1$ is a substituted or unsubstituted heteroarylene as defined above and herein.

In certain embodiments, the linking group $L^1$ comprises between 2 to 50 atoms linked in a chain, e.g., between 2 to 45, 2 to 40, 2 to 35, 2 to 30, 2 to 25, 2 to 20, 2 to 15, 2 to 10, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 atoms in length.

In certain embodiments, $L^1$ is a linker group comprising a combination of one or more groups of the formula:

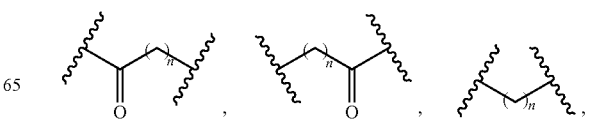

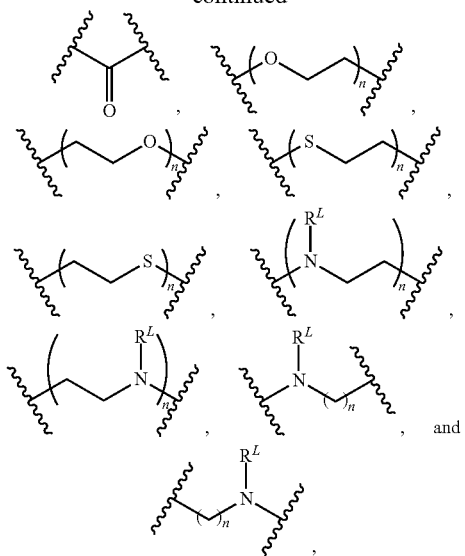

wherein $R^L$ is hydrogen or substituted or unsubstituted alkyl, n is 0 or an integer between 1 to 10, inclusive, e.g., 1, 2, 3, 4, 5, 6, 7, 8, 9, or 10. In certain embodiments, n is 3 or 4.

In certain embodiments, $L^1$ is a linker group of the formula:

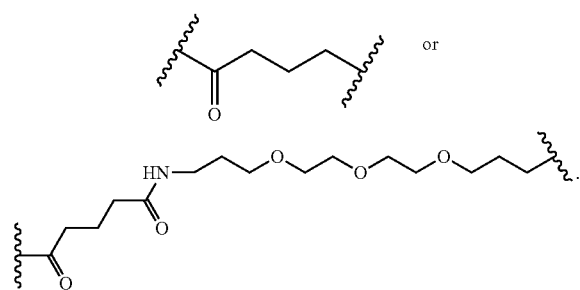

As generally defined above, $L^2$ is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof.

In certain embodiments, $L^2$ is a linking group comprising at least one instance of substituted or unsubstituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^2$ is a substituted or unsubstituted alkylene as defined above and herein.

In certain embodiments, $L^2$ is a linking group comprising at least one instance of substituted or unsubstituted alkenylene, e.g., substituted or unsubstituted $C_{2-6}$alkenylene, substituted or unsubstituted $C_{3-6}$alkenylene, substituted or unsubstituted $C_{4-6}$alkenylene, substituted or unsubstituted $C_{5-6}$alkenylene, substituted or unsubstituted $C_{2-5}$alkenylene, substituted or unsubstituted $C_{2-4}$alkenylene, substituted or unsubstituted $C_{2-3}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene. In certain embodiments, $L^2$ is a substituted or unsubstituted alkenylene as defined above and herein.

In certain embodiments, $L^2$ is a linking group comprising at least one instance of substituted or unsubstituted alkynylene, e.g., substituted or unsubstituted $C_{2-6}$alkynylene, substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene. In certain embodiments, $L^2$ is a substituted or unsubstituted alkynylene as defined above and herein.

In certain embodiments, $L^2$ is a linking group comprising at least one instance of substituted or unsubstituted heteroalkylene, e.g., substituted or unsubstituted hetero$C_{1-6}$alkylene, substituted or unsubstituted hetero$C_{2-6}$alkylene, substituted or unsubstituted hetero$C_{3-6}$alkylene, substituted or unsubstituted hetero$C_{4-6}$alkylene, substituted or unsubstituted hetero$C_{5-6}$alkylene, substituted or unsubstituted hetero$C_{2-5}$alkylene, substituted or unsubstituted hetero$C_{2-4}$alkylene, substituted or unsubstituted hetero$C_{2-3}$alkylene, substituted or unsubstituted hetero$C_1$alkylene, substituted or unsubstituted hetero$C_2$alkylene, substituted or unsubstituted hetero$C_3$alkylene, substituted or unsubstituted hetero$C_4$alkylene, substituted or unsubstituted hetero$C_5$alkylene, or substituted or unsubstituted hetero$C_6$alkylene. In certain embodiments, $L^2$ is a substituted or unsubstituted heteroalkylene as defined above and herein.

In certain embodiments, $L^2$ is a linking group comprising at least one instance of substituted or unsubstituted heteroalkenylene, e.g., substituted or unsubstituted hetero$C_{2-6}$alkenylene, substituted or unsubstituted hetero$C_{3-6}$alkenylene, substituted or unsubstituted hetero$C_{4-6}$alkenylene, substituted or unsubstituted hetero$C_{5-6}$alkenylene, substituted or unsubstituted hetero$C_{2-5}$alkenylene, substituted or unsubstituted hetero$C_{2-4}$alkenylene, substituted or unsubstituted hetero$C_{2-3}$alkenylene, substituted or unsubstituted hetero$C_2$alkenylene, substituted or unsubstituted hetero$C_3$alkenylene, substituted or unsubstituted hetero$C_4$alkenylene, substituted or unsubstituted hetero$C_5$alkenylene, or substituted or unsubstituted hetero$C_6$alkenylene. In certain embodiments, $L^2$ is a substituted or unsubstituted heteroalkenylene as defined above and herein.

In certain embodiments, $L^2$ is a linking group comprising at least one instance of substituted or unsubstituted heteroalkynylene, e.g., substituted or unsubstituted hetero$C_{2-6}$alkynylene, substituted or unsubstituted hetero$C_{3-6}$alkynylene, substituted or unsubstituted hetero$C_{4-6}$alkynylene, substituted or unsubstituted hetero$C_{5-6}$alkynylene, substituted or unsubstituted hetero$C_{2-5}$alkynylene, substituted or unsubstituted hetero$C_{2-4}$alkynylene, substituted or unsubstituted heteroC$_{2-3}$alkynylene, substituted or unsubstituted heteroC$_2$alkynylene, substituted or unsubstituted heteroC$_3$alkynylene, substituted or unsubstituted heteroC$_4$alkynylene, substituted or unsubstituted heteroC$_5$alkynylene, or substituted or unsubstituted heteroC$_6$alkynylene. In certain embodiments, L$^2$ is a substituted or unsubstituted heteroalkynylene as defined above and herein.

In certain embodiments, L$^2$ is a linking group comprising at least one instance of substituted or unsubstituted heterocyclylene, e.g., substituted or unsubstituted 5- to 8-membered heterocyclylene, substituted or unsubstituted 5- to 7-membered heterocyclylene, substituted or unsubstituted 5- to 6-membered heterocyclylene, substituted or unsubstituted 5-membered heterocyclylene, substituted or unsubstituted 6-membered heterocyclylene, substituted or unsubstituted 7-membered heterocyclylene, or substituted or unsubstituted 8-membered heterocyclylene. In certain embodiments, L$^2$ is a substituted or unsubstituted heterocyclylene as defined above and herein.

In certain embodiments, L$^2$ is a linking group comprising at least one instance of substituted or unsubstituted carbocyclylene, e.g., substituted or unsubstituted C$_{3-6}$ carbocyclylene, substituted or unsubstituted C$_{3-5}$ carbocyclylene, substituted or unsubstituted C$_{3-4}$ carbocyclylene, substituted or unsubstituted C$_3$ carbocyclylene, substituted or unsubstituted C$_4$ carbocyclylene, substituted or unsubstituted C$_5$ carbocyclylene, or substituted or unsubstituted C$_6$ carbocyclylene. In certain embodiments, L$^2$ is a substituted or unsubstituted carbocyclylene as defined above and herein.

In certain embodiments, L$^2$ is a linking group comprising at least one instance of substituted or unsubstituted arylene, e.g., substituted or unsubstituted C$_6$ arylene (phenylene) or substituted or unsubstituted C$_{10}$ arylene (naphthylene). In certain embodiments, L$^2$ is a substituted or unsubstituted arylene as defined above and herein.

In certain embodiments, L$^2$ is a linking group comprising at least one instance of substituted or unsubstituted heteroarylene, e.g., substituted or unsubstituted 5-membered heteroarylene or substituted or unsubstituted 6-membered heteroarylene. In certain embodiments, L$^2$ is a substituted or unsubstituted heteroarylene as defined above and herein.

In certain embodiments, the linking group L$^1$ comprises between 2 to 50 atoms linked in a chain, e.g., between 2 to 45, 2 to 40, 2 to 35, 2 to 30, 2 to 25, 2 to 20, 2 to 15, 2 to 10, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 atoms in length.

In certain embodiments, L$^2$ is a linker group comprising a combination of one or more groups of the formula:

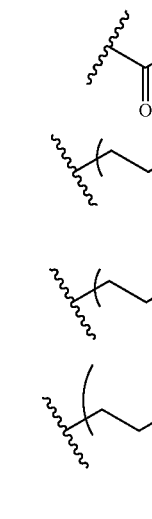

wherein R$^L$ is hydrogen or substituted or unsubstituted alkyl, m is 0 or an integer between 1 to 10, inclusive, e.g., 1, 2, 3, 4, 5, 6, 7, 8, 9, or 10. In certain embodiments, m is 3 or 4.

In certain embodiments, L$^2$ is a linker group of the formula:

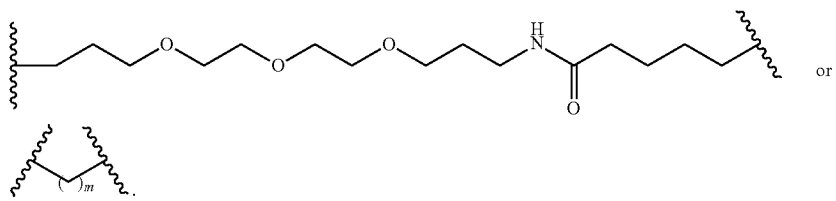 or

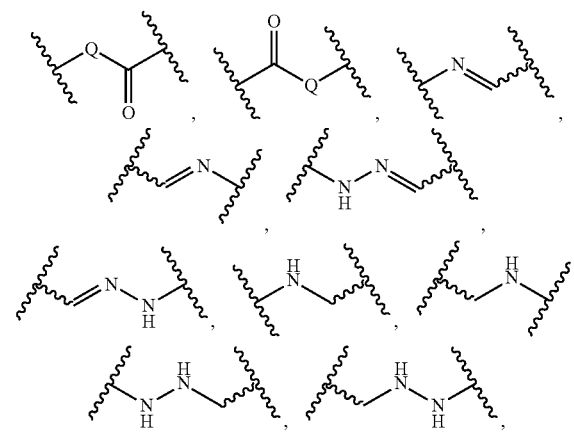

As generally defined above, A is a bond, —NR$^{W1}$—, —NR$^{W1}$—NR$^{W1}$—, —S—, —O—, —S—S—,

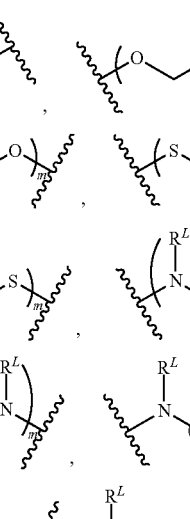

-continued

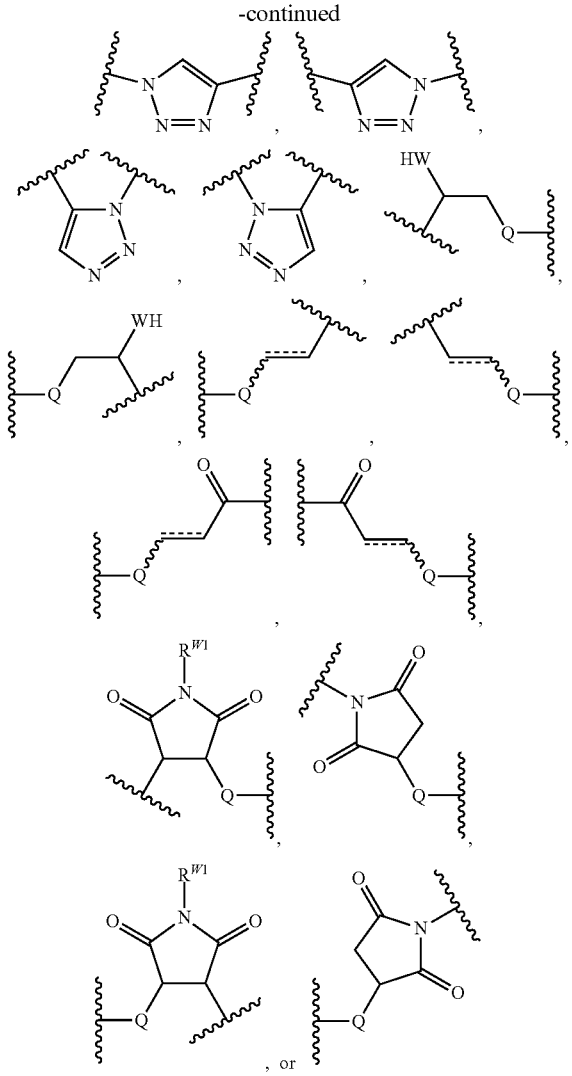

wherein ===== is a single or double bond, W is —O—, —S—, or —NR$^{W1}$—, R$^{W1}$ is hydrogen, substituted or unsubstituted alkyl, or an amino protecting group; and Q is —NR$^{W1}$—, —NR$^{W1}$—NR$^{W1}$—, —S—, —O—; and B is a label or probe.

In certain embodiments, A is —NR$^{W1}$—, e.g., —NH—.
In certain embodiments, A is —NR$^{W1}$—NR$^{W1}$—, e.g., —NH—NH—.
In certain embodiments, A is —S—.
In certain embodiments, A is —O—.
In certain embodiments, A is

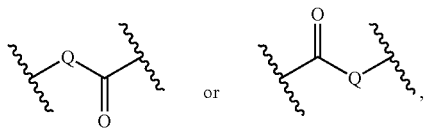

wherein Q is —NR$^{W1}$—, —NR$^{W1}$—NR$^{W1}$—, —S—, —O—. For example, in certain embodiments, wherein Q is —NH—, A is an amide group of the formula

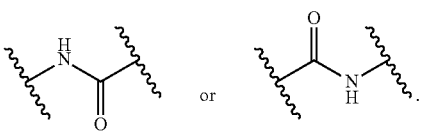 [SMILES: *NC(*)=O ; *NC(*)=O]

In certain embodiments, wherein Q is —NH—NH—, A is an amide hydrazide group of the formula

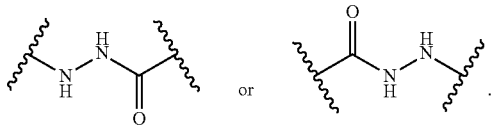 [SMILES: *NNC(*)=O ; *NNC(*)=O]

In certain embodiments, wherein Q is —S—, A is an thioester group of the formula

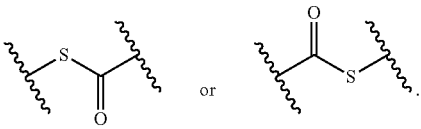 [SMILES: *SC(*)=O ; *SC(*)=O]

In certain embodiments, wherein Q is —O—, A is an ester group of the formula

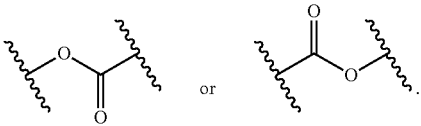

In certain embodiments, A is

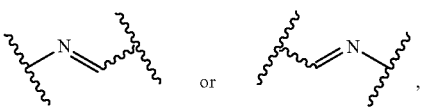

In certain embodiments, A is

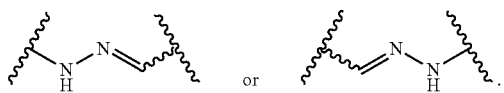

In certain embodiments, A is

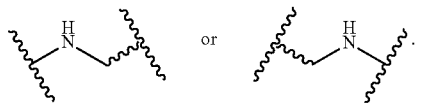

In certain embodiments, A is

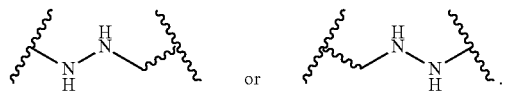

In certain embodiments, A is

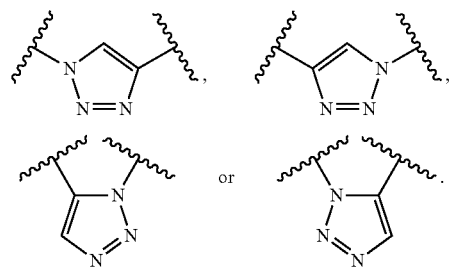

In certain embodiments, A is

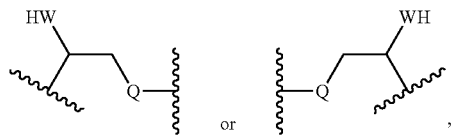

wherein W is —O—, —S—, or —NR$^{W1}$—, R$^{W1}$ is hydrogen, substituted or unsubstituted alkyl, or an amino protecting group; and Q is —NR$^{W1}$—, —NR$^{W1}$—NR$^{W1}$—, —S—, —O—. In certain embodiments, W is —O—. In certain embodiments, W is —S—. In certain embodiments, W is —NR$^{W1}$—. In certain embodiments, Q is —NH—. In certain embodiments, Q is —NH—NH—. In certain embodiments, Q is —S—. In certain embodiments, Q is —O—.

In certain embodiments, A is

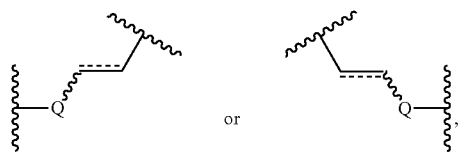

wherein ------ is a single or double bond, and Q is —NR$^{W1}$—, —NR$^{W1}$—NR$^{W1}$—, —S—, —O—. In certain embodiments, Q is —NH—. In certain embodiments, Q is —NH—NH—. In certain embodiments, Q is —S—. In certain embodiments, Q is —O—.

In certain embodiments, A is

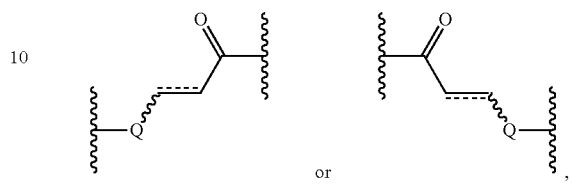

wherein ------ is a single or double bond, and Q is —NR$^{W1}$—, —NR$^{W1}$—NR$^{W1}$—, —S—, —O—. In certain embodiments, Q is —NH—. In certain embodiments, Q is —NH—NH—. In certain embodiments, Q is —S—. In certain embodiments, Q is —O—.

In certain embodiments, A is

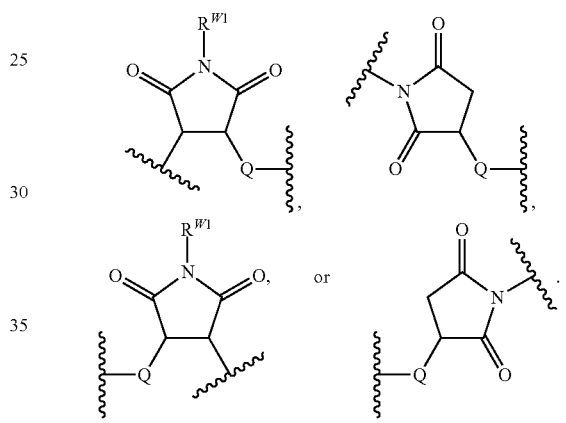

wherein W is —O—, —S—, or —NR$^{W1}$—, R$^{W1}$ is hydrogen, substituted or unsubstituted alkyl, or an amino protecting group; and Q is —NR$^{W1}$—, —NR$^{W1}$—NR$^{W1}$—, —S—, —O—. In certain embodiments, W is —O—. In certain embodiments, W is —S—. In certain embodiments, W is —NR$^{W1}$—. In certain embodiments, Q is —NH—. In certain embodiments, Q is —NH—NH—. In certain embodiments, Q is —S—. In certain embodiments, Q is —O—.

Various combinations of -L$^1$-A-L$^2$- are further contemplated herein. See, for example Table 1.

TABLE 1

| L$^1$ | A | L$^2$ |
|---|---|---|
| (ketone linker) | (amide linker) | (PEG-amide linker) |
| (amide-PEG linker) | (amide linker) | (methylene linker, wherein m is 4) |

As generally defined above, B is a label. A "label," as used herein, refers to a detectable moiety, i.e., a moiety which provides a detectable (e.g., visually detectable) analytical signal. Various detectable moieties are contemplated herein, and include, but are not limited to, (a) a molecule which contains isotopic moieties, e.g., for use in radioimmunoassays, which may be radioactive and/or isotopic and include, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-$^{99}m$), $^{111}In$, $^{123}I$, $^{125}I$, $^{169}Yb$, and $^{186}Re$), (b) an enzyme or coenzyme; (c) a molecule which is colored (chromophore), fluorescent, phosphorescent, or chemiluminescent dyes; (d) a molecule which has one or more photo affinity moieties; (e) a molecule which has a ligand moiety with one or more known binding partners (haptens such as biotin, dinitrophenol (DNP), and digoxigenin); (f) latex and magnetic particles; (g) gold, silver, and selenium colloidal particles; (h) metal chelates; and (i) oligonucleotides. A wide variety of detectable moieties can be used, with the choice of label depending on the sensitivity required, stability requirements, and available instrumentation and disposal provisions. All of above can be used as label, and by attaching to the compound, they can be located with different detection method, e.g., for example, using Halo tag.

In certain embodiments, the label is biotin. The biotin moiety allows the compound of Formula (I) or (II) to bind to certain surface such as, for example, beads, glass, or metal surface.

In certain embodiments, the label is a fluorescent moiety. A "fluorescent moiety" or label as used herein refer to a moiety that absorbs light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide), HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, Pa.-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP, green fluorescent protein (GFP), phycoerythrin, hydroxycoumarin, aminocoumarin, methoxycoumarin, cascade blue, pacific blue, pacific orange, Lucifer yellow, NBD, R-Phycoerythrin (PE), PE-Cy5, PE-Cy7, Red 613, PerCP, TruRed, FluorX, fluorescein, fluorescein isothiocyanate (FITC), X-Rhodamine, Lissamine Rhodamine B, Texas red, tetrarhodamine isothiocynate (TRITC), BODIPY-FL, Cy2, Cy3, Cy3B, Cy3.5, Cy5, Cy5.5, Cy7, Allophycocyanin (APC), APC-Cy7, ATTO655, Alexa Fluor 405, Alexa Fluor 568, and Alexa Fluor 647. See also Lavis et al., *ACS Chem. Biol.* (2008) 142-155 disclosing various florescent labels. In certain embodiments, the label is fluorescein isothiocyanate (FITC).

In certain embodiments, B is biotin and the compound of Formula (I) and (II) is:

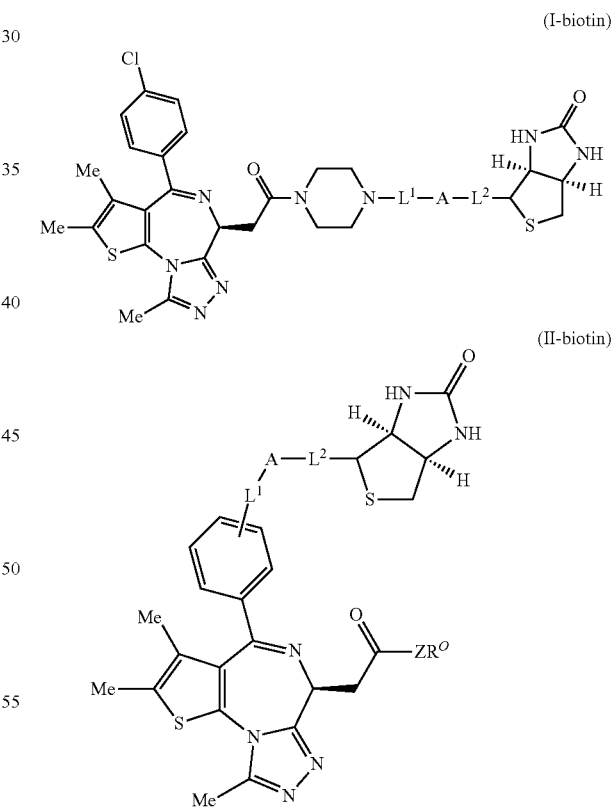

or a salt thereof.

In certain embodiments, the group -L$^{1}$-A-L$^{2}$-biotin of Formula (II-biotin) is attached to the para position of the phenyl ring relative to the diazepine point of attachment.

In certain embodiments, B is FITC, and the compound of Formula (I) and (II) is:

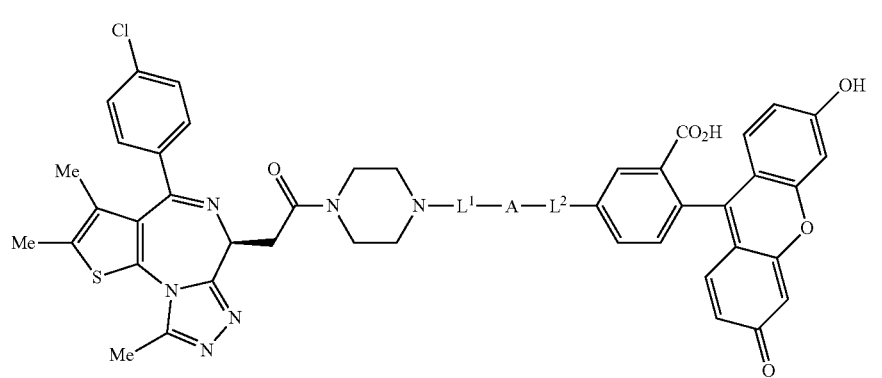
(I-FITC)
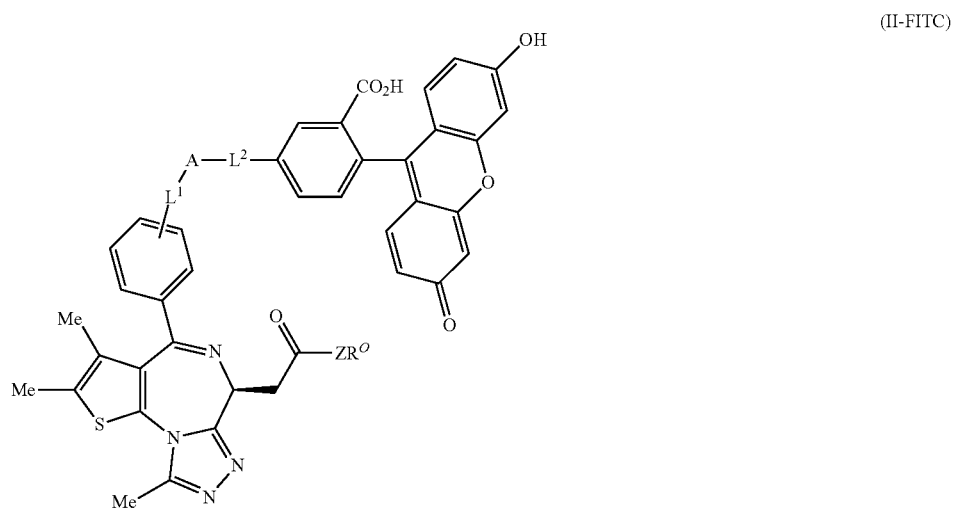
(II-FITC)
or a salt thereof.
In certain embodiments, the group -L$^1$-A-L$^2$-FITC of Formula (II-FITC) is attached to the para position of the phenyl ring relative to the diazepine point of attachment.
In certain embodiments, the compound of Formula (I) is:
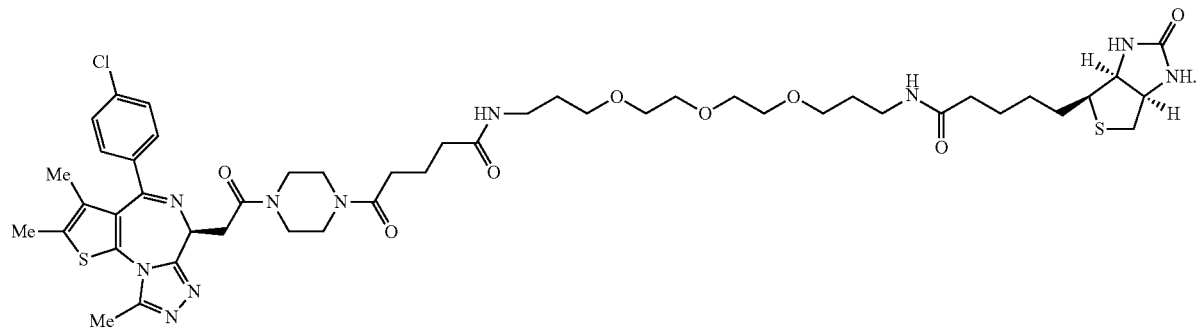 [SMILES: Cc1sc2c(c1C)C(c1ccc(Cl)cc1)=N[C@@H](CC(=O)N1CCN(C(=O)CCCC(=O)NCCCOCCOCCOCCCNC(=O)CCCC[C@@H]3SC[C@@H]4NC(=O)N[C@@H]43)CC1)c1nnc(C)n1-2]
or a salt thereof.

Compounds of Formula (P-I) and (P-II)

In other aspects, provided are compounds of Formula (P-I) and (P-II):

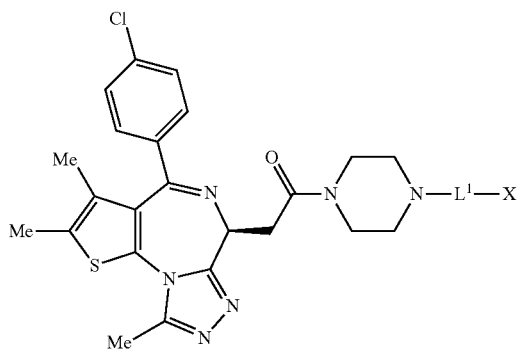
(P-I)

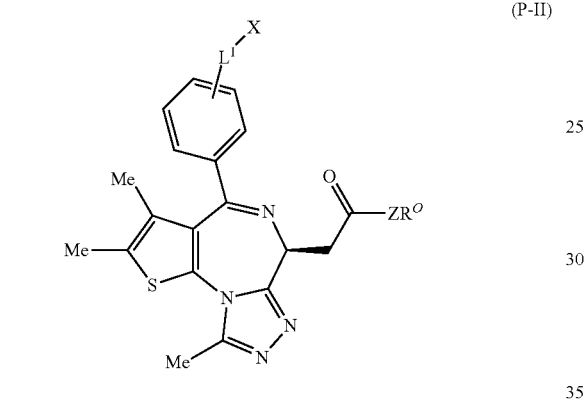
(P-II)

or a salt thereof; wherein Z, $R^O$ and $L^1$ is as defined herein; and

X is selected from the group consisting of —SH, —OH, —NH$_2$, —NH—NH$_2$, —N$_3$, halogen, —C(=O)R$^{Z1}$,

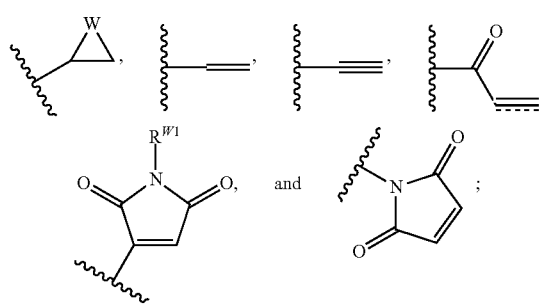
and ;

wherein:
≡ represents a double or triple bond;
$R^{Z1}$ is hydrogen, halogen, or —OR$^{Z2}$, wherein $R^{Z2}$ is hydrogen, substituted or unsubstituted alkyl, or an oxygen protecting group;
W is —O—, —S—, or —NR$^{W1}$—, wherein $R^{W1}$ is hydrogen, substituted or unsubstituted alkyl, or a nitrogen protecting group;
provided the group -L$^1$-X of Formula (P-I) is not —CH$_2$CH$_2$OH.

In certain embodiments, the group -L$^1$-X of the compound of Formula (P-II) is attached to the ortho, meta, or para position of the phenyl ring relative to the diazepine point of attachment, i.e., to provide a compound of Formula (P-II-a), (P-II-b), or (P-II-c):

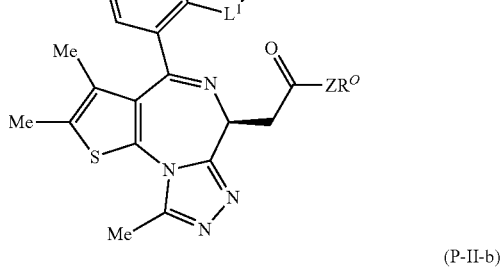
(P-II-a)

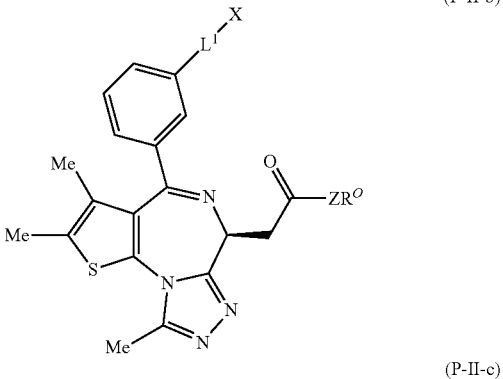
(P-II-b)

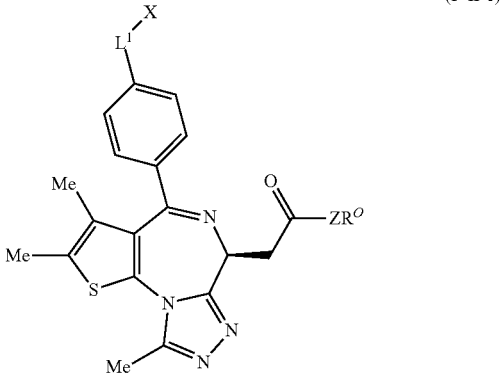
(P-II-c)

or a salt thereof.

In certain embodiments, the compound of Formula (P-II) or a salt thereof is a compound of Formula (P-II-c) or a salt thereof.

In certain embodiments, X is —SH.
In certain embodiments, X is —OH.
In certain embodiments, X is —NH$_2$.
In certain embodiments, X is —NH—NH$_2$.
In certain embodiments, X is —N$_3$.
In certain embodiments, X is halogen, e.g., —Cl, —Br, or —I.
In certain embodiments, X is —C(=O)R$^{Z1}$, wherein $R^{Z1}$ is hydrogen, i.e., to provide X as an aldehyde —CHO.
In certain embodiments, X is —C(=O)R$^{Z1}$, wherein $R^{Z1}$ is halogen (e.g., "Hal" representing —Cl, —Br, and —I), i.e., to provide X as an acyl halide —C(=O)—Hal.
In certain embodiments, X is —C(=O)R$^{Z1}$, wherein $R^{Z1}$ is —OR$^{Z2}$, and wherein $R^{Z2}$ is hydrogen, i.e., to provide X as a carboxylic acid —C(=O)OH.

In certain embodiments, X is —C(=O)R$^{Z1}$, wherein R$^{Z1}$ is —OR$^{Z2}$, and wherein R$^{Z2}$ is substituted or unsubstituted alkyl, or an oxygen protecting group, i.e., to provide X as an ester —C(=O)OR$^{Z2}$, wherein R$^{Z2}$ is substituted or unsubstituted alkyl, or an oxygen protecting group.

In certain embodiments, X is an oxiranyl, thiorenyl, or azirdinyl group of formula:

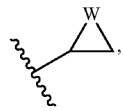

wherein W is —O—, —S—, or —NR$^{W1}$—. In certain embodiments, W is —O—. In certain embodiments, W is —S—. In certain embodiments, W is —NR$^{W1}$—.

In certain embodiments, X is of the formula:

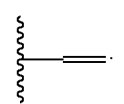 [SMILES: *C=C]

In certain embodiments, X is of the formula:

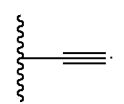

In certain embodiments, X is of the formula:

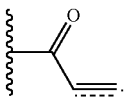

In certain embodiments, X is a maleimide of the formula:

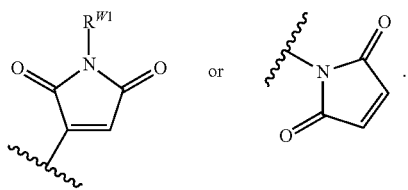

In certain embodiments, the compound of Formula (P-I) is selected from the group consisting of:

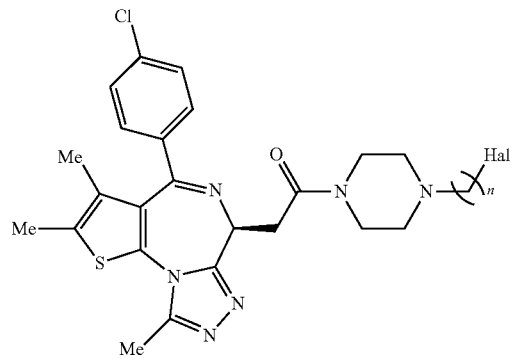

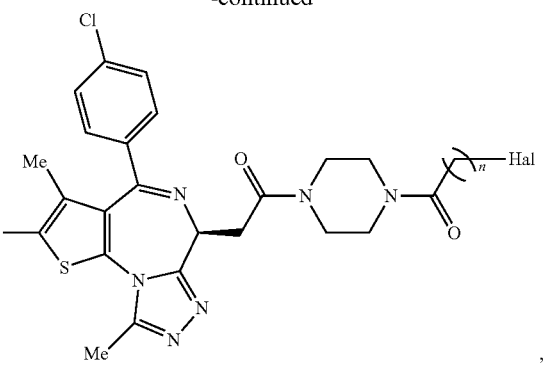

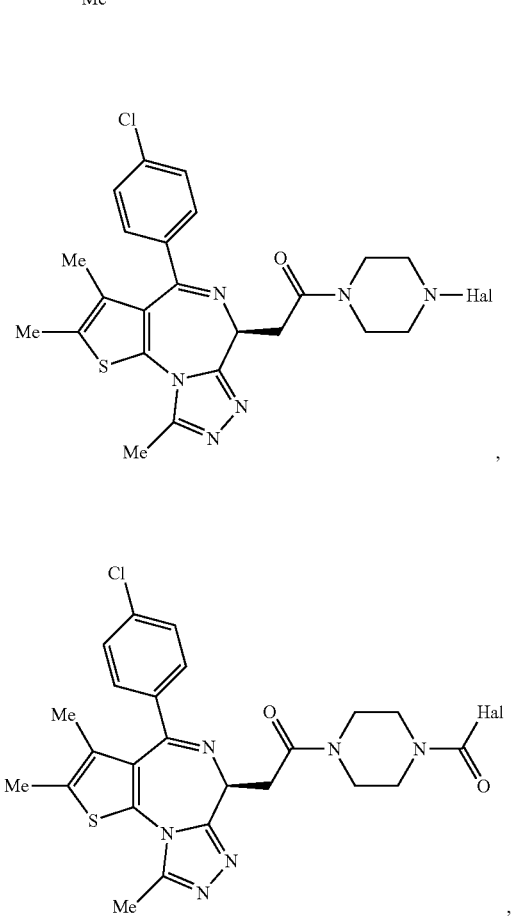

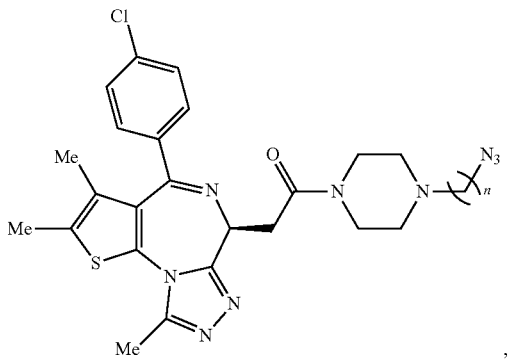

59
-continued
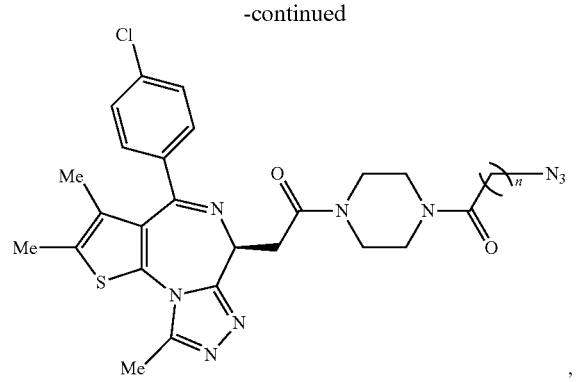
,
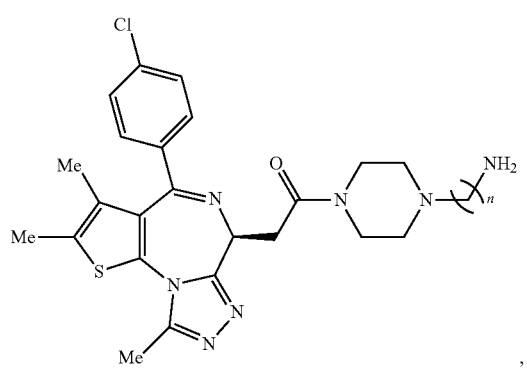
,
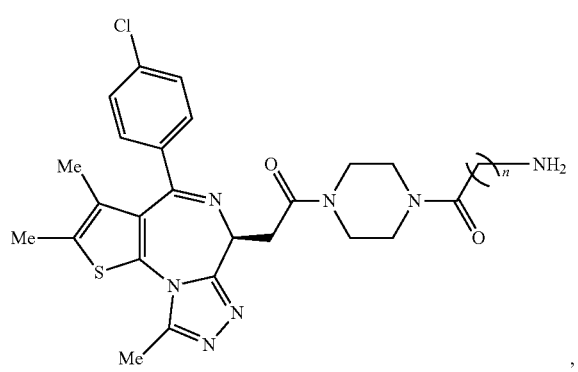
,
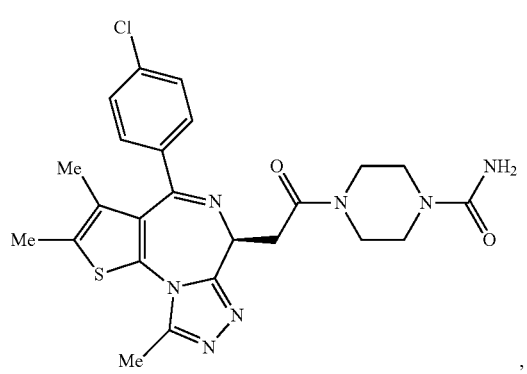
,
60
-continued
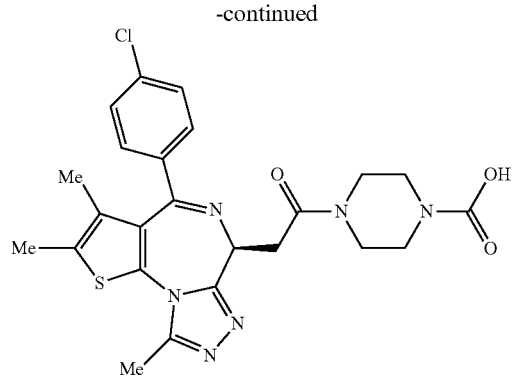
,
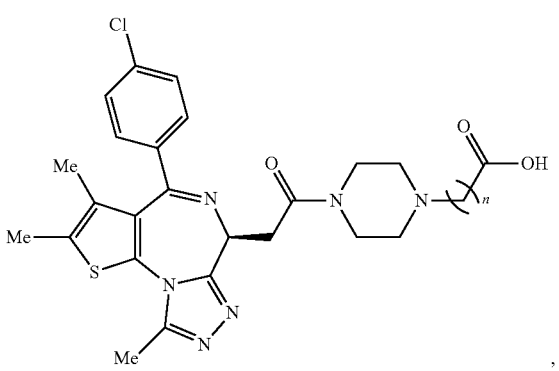
,
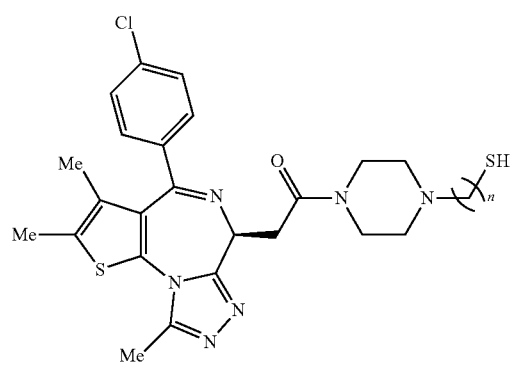
, -continued
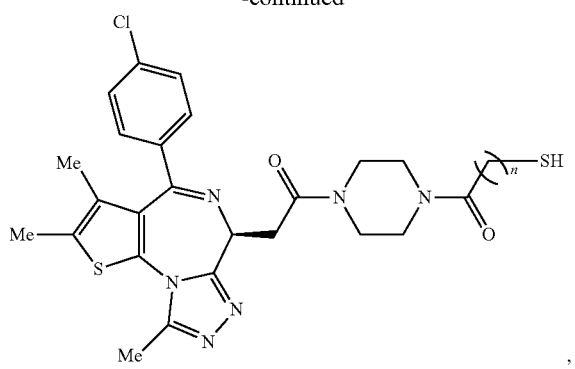
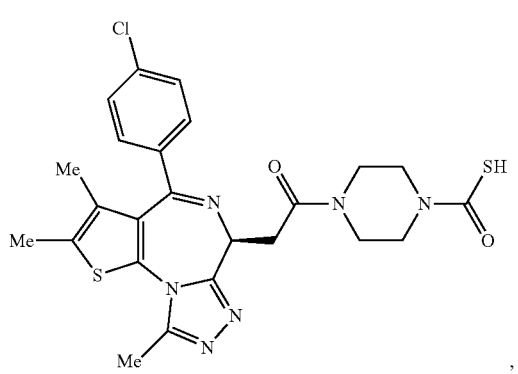
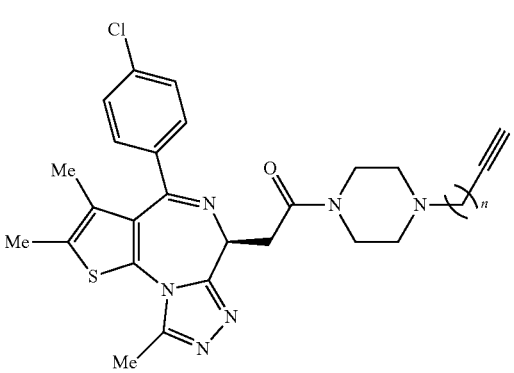
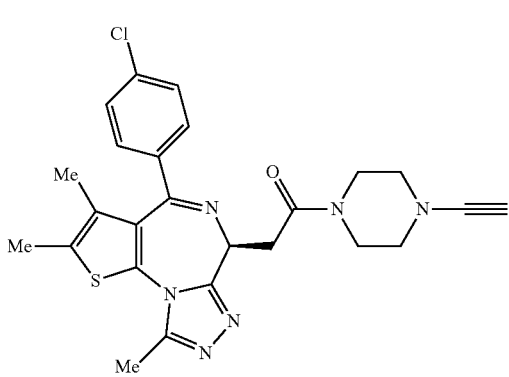
-continued
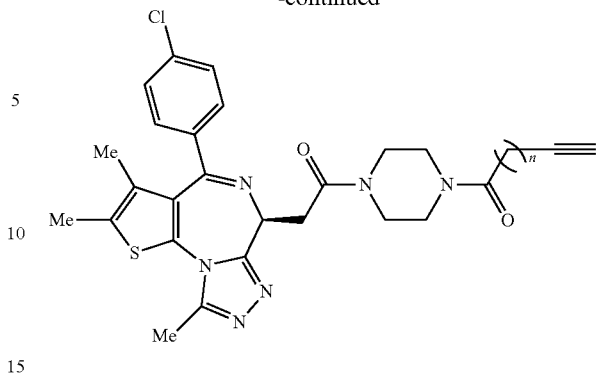
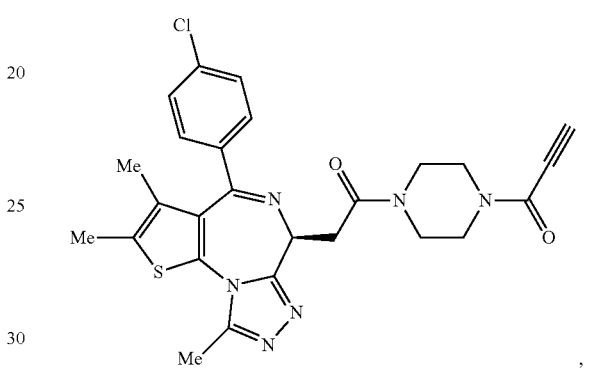
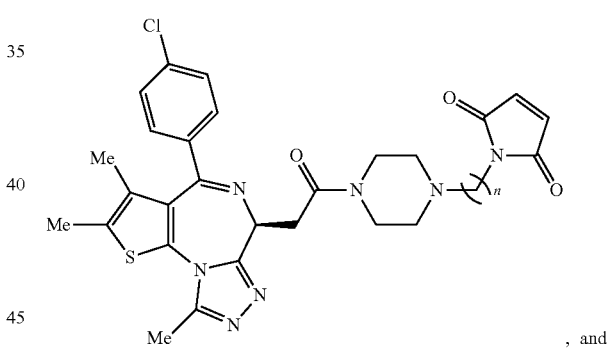
, and
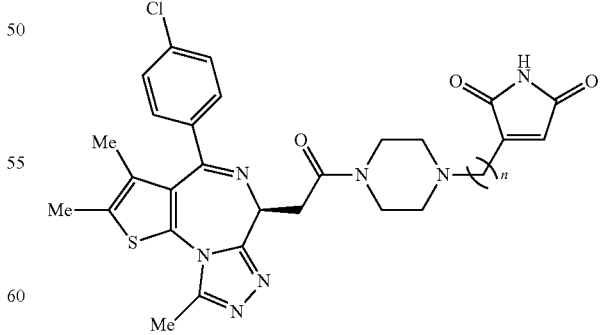
and salts thereof, wherein n is 0 or an integer between 1 and 10, inclusive, and Hal is —Cl, —Br, or —I.
In certain embodiments, the compound of Formula (P-II) is selected from the group consisting of:

63
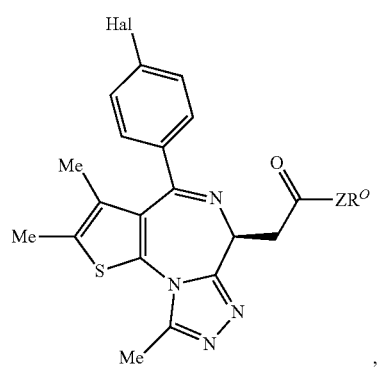
,
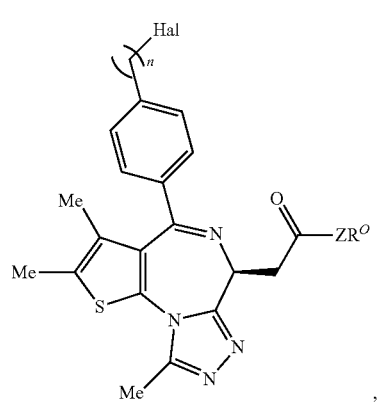
,
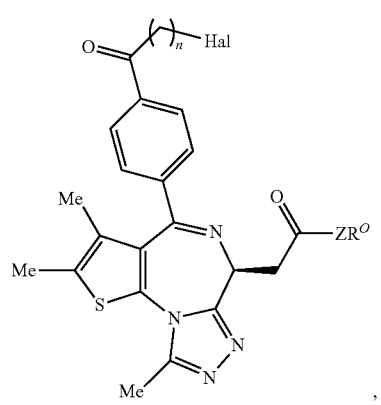
,
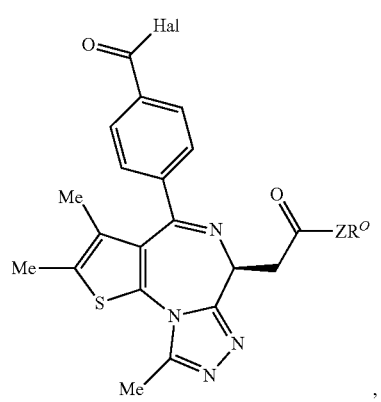
,
64
-continued
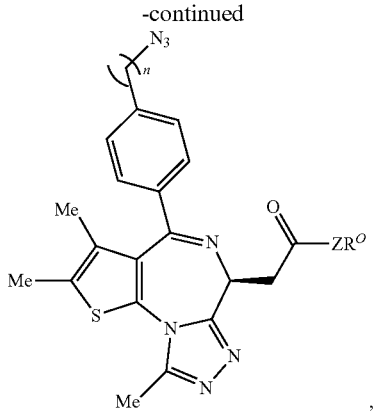
,
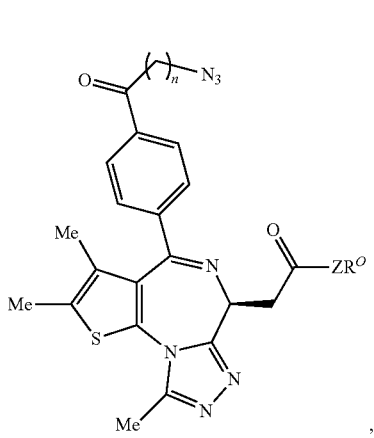
,
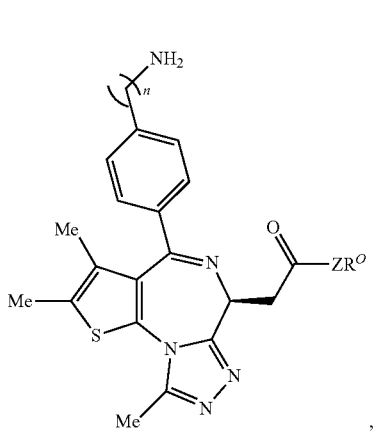
,
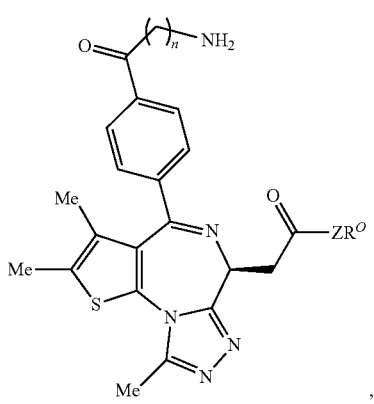
, -continued
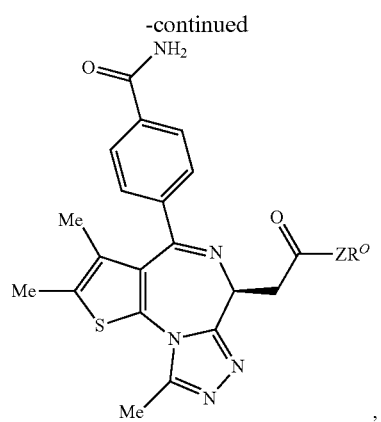
,
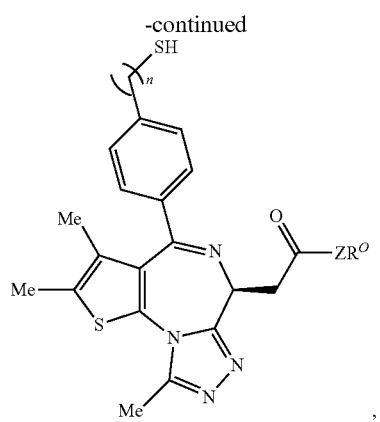
,
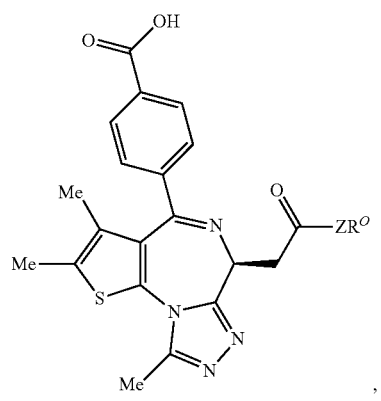
,
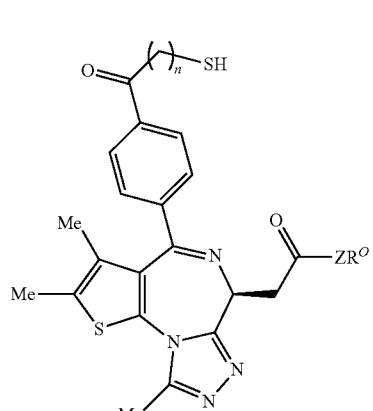
,
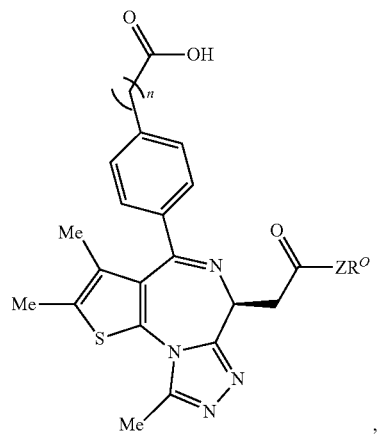
,
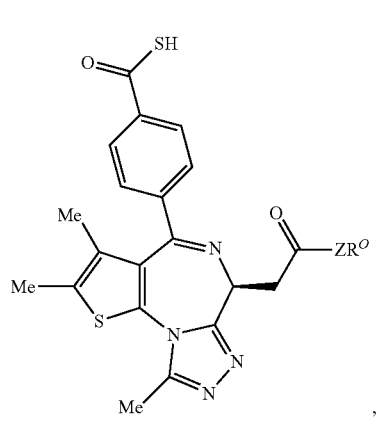
,
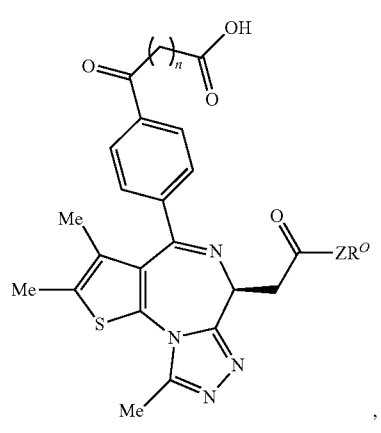
,
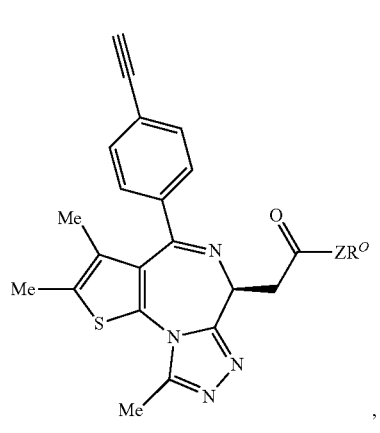
, -continued

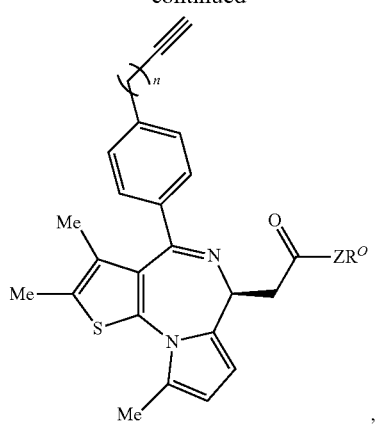

,

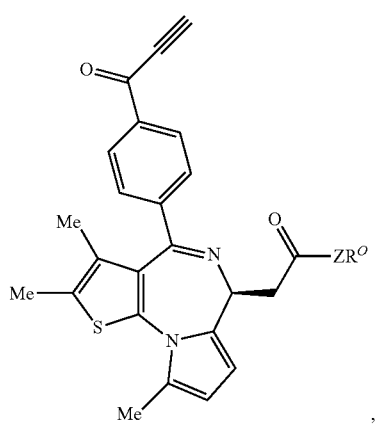

,

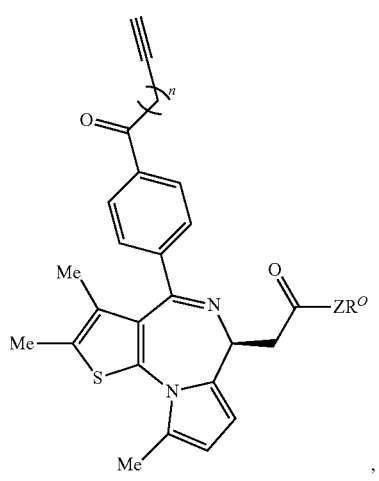

,

-continued

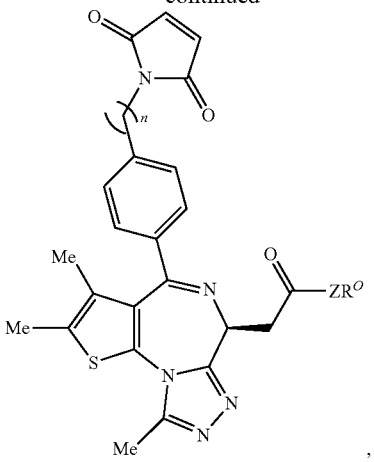

, and

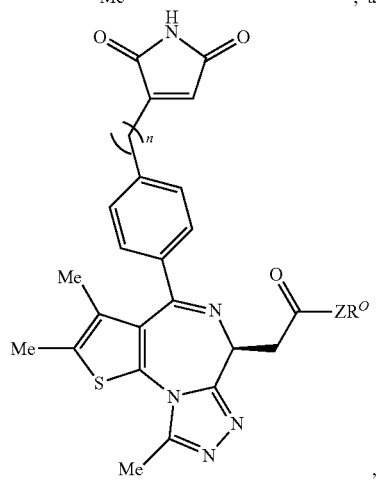

, and salts thereof, wherein n is 0 or an integer between 1 and 10, inclusive; and Hal is —Cl, —Br, or —I.

Methods of Preparation

The compounds of Formula (I) and (II) may be prepared from the coupling of a precursor compound of Formula (P-I) or (P-II) with a compound of Formula (P-III), Y-L²-B. Such methods of preparation may involve click chemistry or any other bond forming chemistry. Click chemistry is a chemical philosophy introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary chemical coupling reactions include, but are not limited to, the formation of esters, thioesters, amides (e.g., such as peptide coupling) from activated acids or acyl halides, nucleophilic displacement reactions (e.g., such as nucleophilic displacement of a halide or ring opening of strained ring systems); azide-alkyne Huisgen cycloaddition; thiol-yne addition; imine formation; and maleimide addition.

In general, the compound of Formula (P-III), Y-L²-B, should be complimentary and reactive with the group X present on the precursor compound of Formula (P-1) or (P-2) in order to form the compound of Formula (I) or (II). For example, if the group Y of Y-L²-B is a nucleophilic group, the group X would typically be an electrophilic group. Likewise, if the group Y of Y-L²-B is an electrophilic group, the group X would typically be a nucleophilic group.

While X and Y are defined the same in the present invention, it is thus understood that such groups are paired compliments so that when they are reacted together under suitable conditions a covalent linkage is formed.

Thus, in another aspect, provided is a compound of Formula (P-III), Y-L$^2$-B, useful in the preparative methods as described herein, wherein L$^2$ and B are as defined herein, and Y is selected from the group consisting of —SH, —OH, —NH$_2$, —NH—NH$_2$, —N$_3$, halogen, —C(=O)R$^{Z1}$,

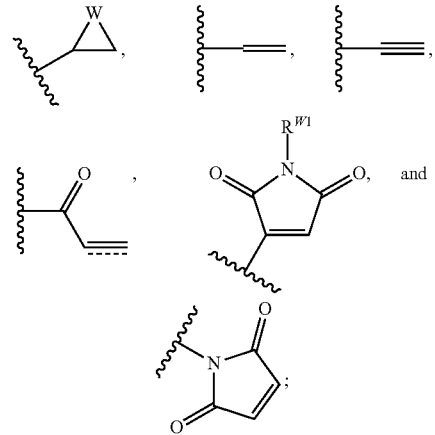

wherein:
≡ represents a double or triple bond;
R$^{Z1}$ is hydrogen, halogen, or —OR$^{Z2}$, wherein R$^{Z2}$ is hydrogen, substituted or unsubstituted alkyl, or an oxygen protecting group; and
W is —O—, —S—, or —NR$^{W1}$—, wherein R$^{W1}$ is hydrogen, substituted or unsubstituted alkyl, or a nitrogen protecting group.

In certain embodiments, Y is —SH.
In certain embodiments, Y is —OH.
In certain embodiments, Y is —NH$_2$.
In certain embodiments, Y is —NH—NH$_2$.
In certain embodiments, Y is —N$_3$.
In certain embodiments, Y is halogen, e.g., —Cl, —Br, or —I.
In certain embodiments, Y is —C(=O)R$^{Z1}$, R$^{Z1}$ is hydrogen, i.e., to provide Y as an aldehyde —CHO.
In certain embodiments, Y is —C(=O)R$^{Z1}$, wherein R$^{Z1}$ is halogen (e.g., "Hal" representing —Cl, —Br, and —I), i.e., to provide Y as an acyl halide —C(=O)—Hal.
In certain embodiments, Y is —C(=O)R$^{Z1}$, wherein R$^{Z1}$ is —OR$^{Z2}$, and wherein R$^{Z2}$ is hydrogen, i.e., to provide Y as a carboxylic acid —C(=O)OH.
In certain embodiments, Y is —C(=O)R$^{Z1}$, wherein R$^{Z1}$ is —OR$^{Z2}$, and wherein R$^{Z2}$ is substituted or unsubstituted alkyl or an oxygen protecting group, i.e., to provide Y as an ester —C(=O)OR$^{Z2}$, wherein R$^{Z2}$ is substituted or unsubstituted alkyl or an oxygen protecting group.
In certain embodiments, Y is an oxiranyl, thiorenyl, or azirdinyl group of formula:

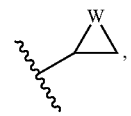

wherein W is —O—, —S—, or —NR$^{W1}$—. In certain embodiments, W is —O—. In certain embodiments, W is —S—. In certain embodiments, W is —NR$^{W1}$—.

In certain embodiments, Y is of formula:

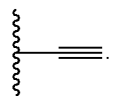

In certain embodiments, Y is of formula:

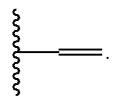

In certain embodiments, Y is of formula:

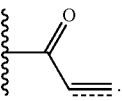

In certain embodiments, Y is a maleimide group of formula:

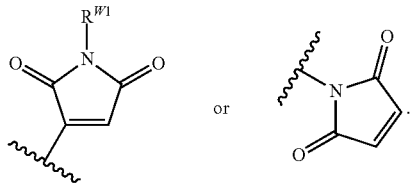

In one aspect, provided is a method of preparing a compound of Formula (I) or (II), or salt thereof, comprising coupling of a precursor compound of Formula (P-I) or (P-II), or salt thereof, with a compound of Formula (P-III), or salt thereof.

In certain embodiments, the method of preparing a compound of Formula (I) or (II) comprises coupling a precursor compound of Formula (P-I) or (P-II) with a compound of Formula (P-III), wherein one of X and Y is —C(=O)R$^{Z1}$, wherein R$^{Z1}$ is halogen or —OR$^{Z2}$, and one of X and Y is —SH, —OH, —NH$_2$, —NH—NH$_2$ to provide a compound of Formula (I) or (II), wherein A is an amide, thioester, or ester group. See, for example, various methods of preparing compounds of Formula (I) and (II) as provided in the below Schemes (1A) to (1D) and Table 2.

Scheme 1.
Preparation of compounds of Formula (I) and (II) via amide, thioester, and ester formation Scheme 1A.

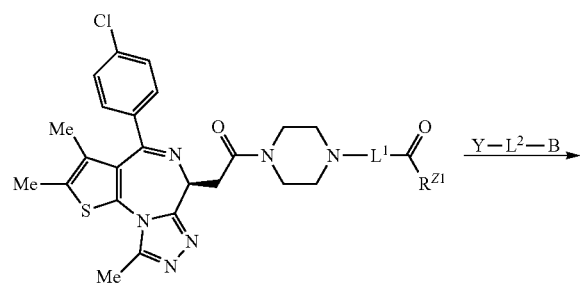

71
-continued
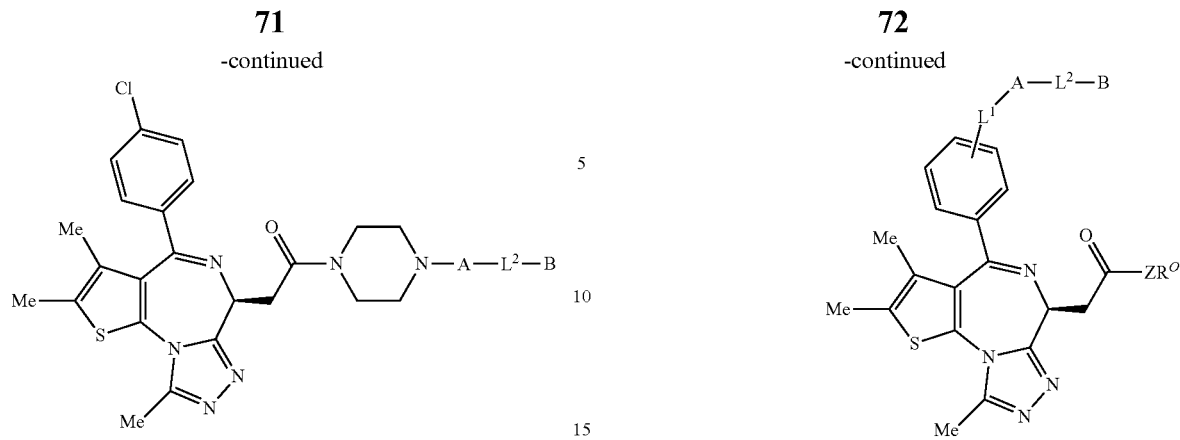
Scheme 1B.
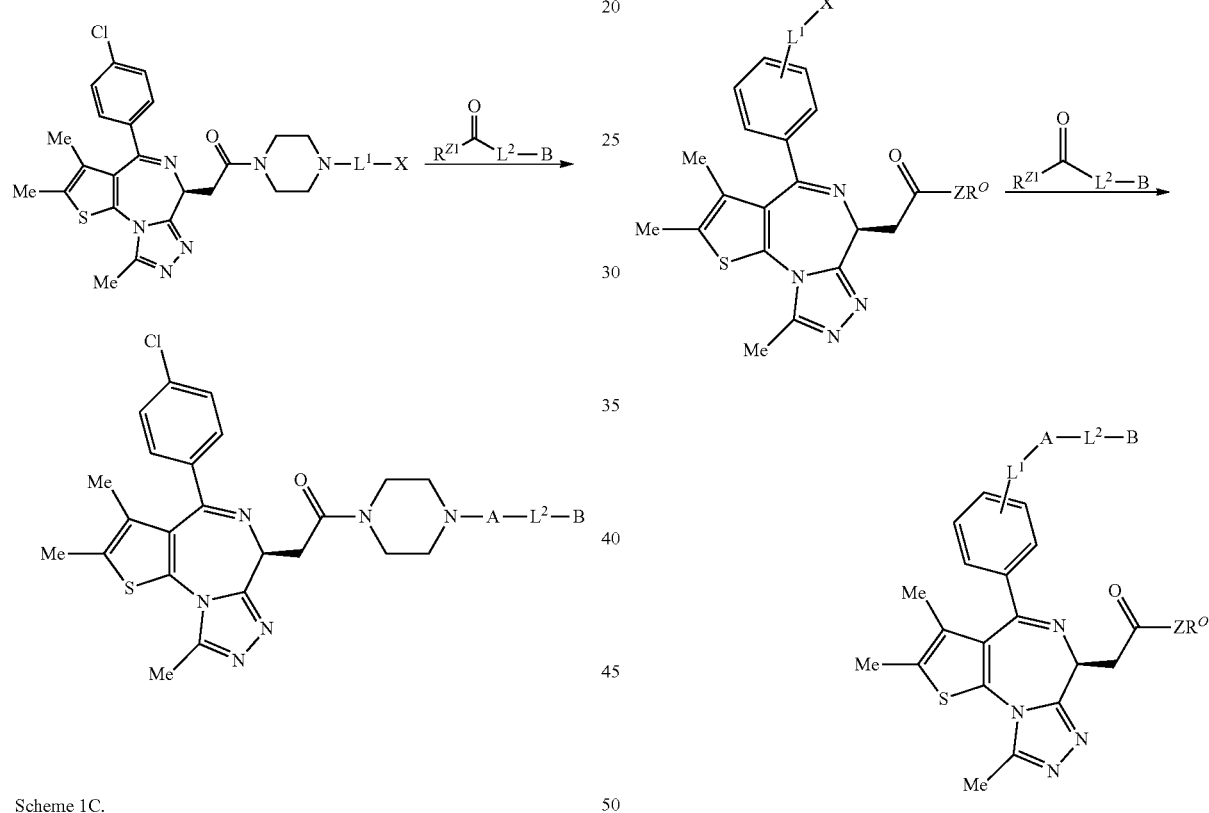
Scheme 1C.
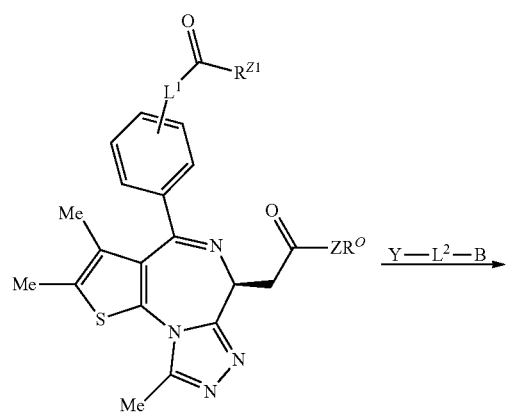
72
-continued
Scheme 1D.
TABLE 2
| $R^{Z1}$ | Y | X | A<br>—C(═O)Q—, —QC(═O)— |
|---|---|---|---|
| halogen<br>or —OR$^{Z2}$ | —SH | — | —C(═O)S— |
|  | — | —SH | —SC(═O)— |
|  | —OH | — | —C(═O)O— |
|  | — | —OH | —OC(═O)— |
|  | —NH$_2$ | — | —C(═O)NH— |
|  | — | —NH$_2$ | —NHC(═O)— |
|  | —NH—NH$_2$ | — | —C(═O)NHNH— |
|  | — | —NH—NH$_2$ | —NHNHC(═O)— |
*—C(═O)OR$^O$ is a less reactive electrophile than —C(═O)R$^{Z1}$
In certain embodiments, the method of preparing a compound of Formula (I) or (II) comprises coupling a precursor compound of Formula (P-I) or (P-II) with a compound of Formula (P-III), wherein one of X and Y is halogen or other leaving group; and one of X and Y is —SH, —OH, —NH₂, —NH—NH₂ to provide a compound of Formula (I) or (II), wherein A is, respectively, —S—, —O—, —NH—, or —NH—NH—. See, for example, various methods of preparing compounds of Formula (I) and (II) as provided in the below Schemes (2A) to (2D) and Table 3.

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and sulfonyl substituted hydroxyl groups (e.g., tosyl, mesyl, besyl).

Scheme 2. Nucleophilic displacement of a halide

Scheme 2A.

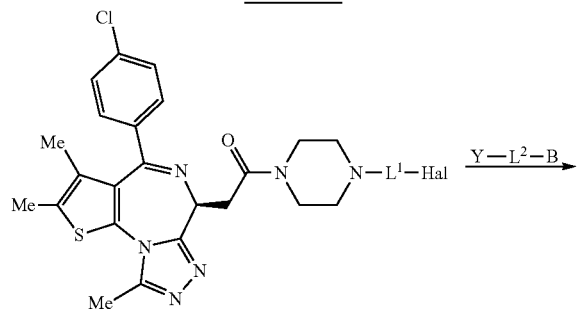

Hal = —Cl, —Br, —I

Scheme 2B.

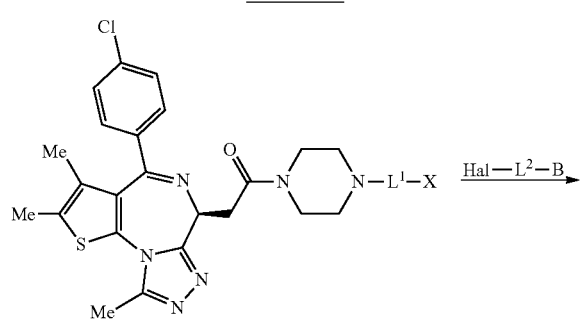

-continued

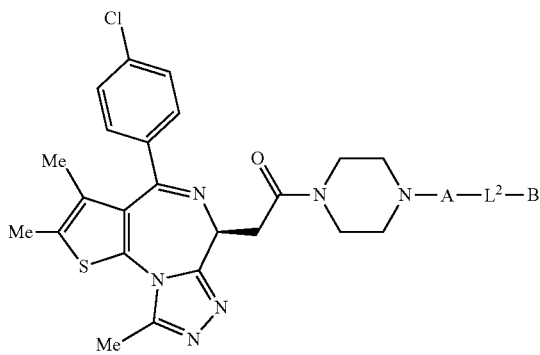

Hal = —Cl, —Br, —I

Scheme 2C.

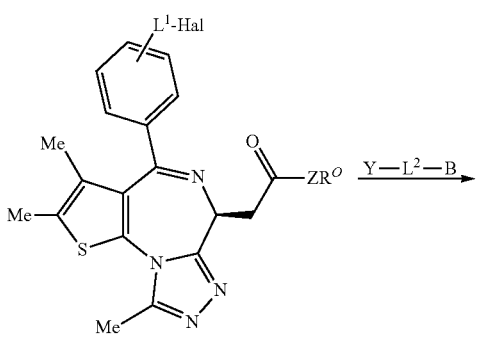

Hal = —Cl, —Br, —I

Scheme 2D.

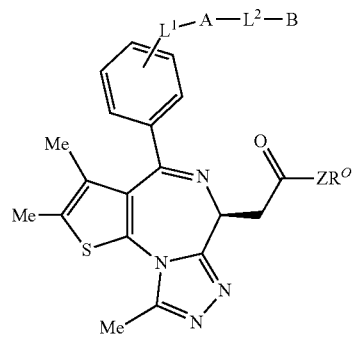

75
-continued

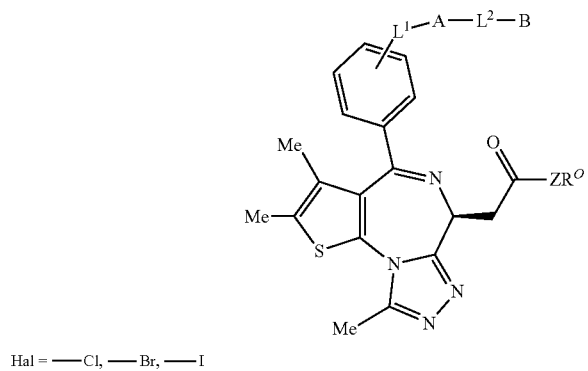

Hal = —Cl, —Br, —I

76
-continued

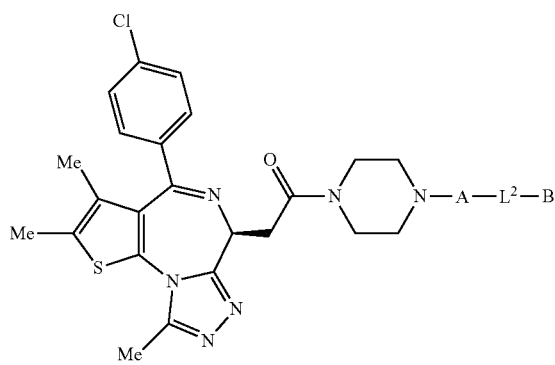

TABLE 3

| Y | X | A |
|---|---|---|
| — | —SH | —S— |
| | —OH | —O— |
| | —NH$_2$ | —NH— |
| | —NH—NH$_2$ | —NH—NH— |
| —SH | — | —S— |
| —OH | | —O— |
| —NH$_2$ | | —NH— |
| —NH—NH$_2$ | | —NH—NH— |

In certain embodiments, the method of preparing a compound of Formula (I) or (II) comprises coupling a precursor compound of Formula (P-I) or (P-II) with a compound of Formula (P-III), wherein one of X and Y is

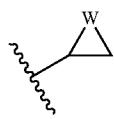

and one of X and Y is —SH, —OH, —NH$_2$, —NH—NH$_2$ to provide the coupled compound of Formula (I) or (II). See, for example, various methods of preparing compounds of Formula (I) and (II) as provided in the below Schemes (3A) to (3D) and Table 4.

Scheme 3. Nucleophilic addition to strained ring systems

Scheme 3A.

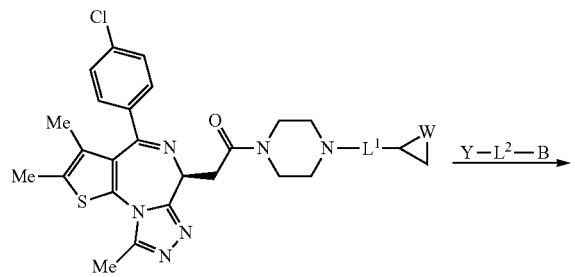

Scheme 3B.

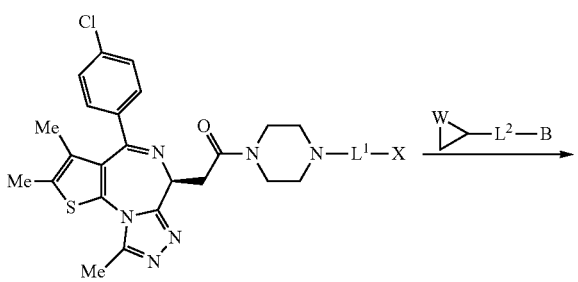

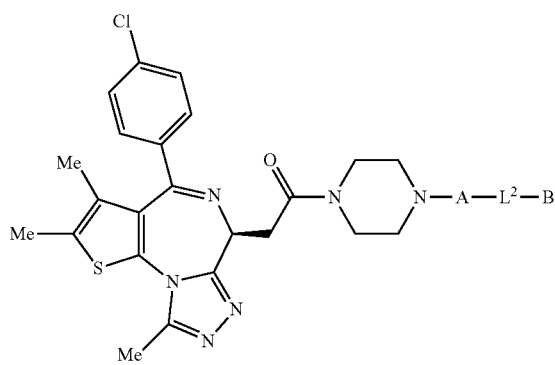

Scheme 3C.

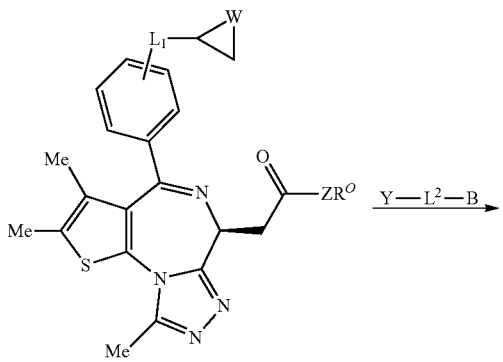

-continued

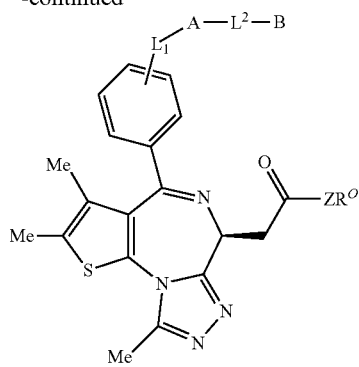

Scheme 3D.

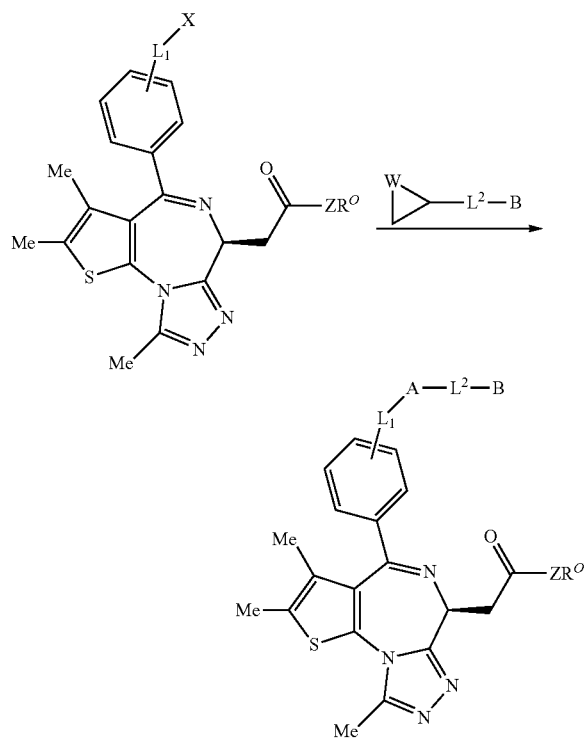

TABLE 4

| W | Y | X | A |
|---|---|---|---|
| —O—, —S—, —NR^{W1}— | —SH | — | HW... |
|  | —OH | — | HW... |
|  | —NH$_2$ | — | HW... |

TABLE 4-continued

| W | Y | X | A |
|---|---|---|---|
|  | —NH—NH$_2$ | — | HW... |
| —O—, —S—, —NR^{W1}— | — | —SH | WH... |
|  | — | —OH | WH... |
|  | — | —NH$_2$ | WH... |
|  | — | —NH—NH$_2$ | WH... |

In certain embodiments, the method of preparing a compound of Formula (I) or (II) comprises coupling (azide-alkyne Huisgen cycloaddition) a precursor compound of Formula (P-I) or (P-II) with a compound of Formula (P-III), wherein one of X and Y is and one of X and Y is —N$_3$ to provide the compound of Formula (I) or (II). See, for example, various methods of preparing compounds of Formula (I) and (II) as provided in the below Schemes (4A) to (4D) and Table 5.

Scheme 4. Azide-alkyne Huisgen cycloaddition

Scheme 4A.

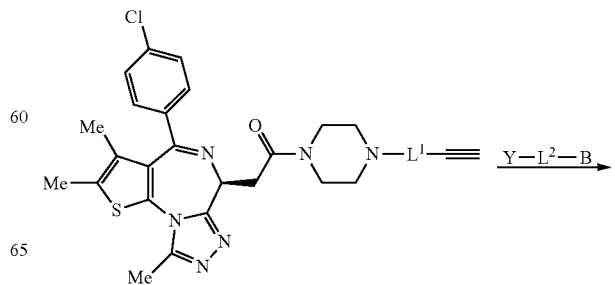

-continued
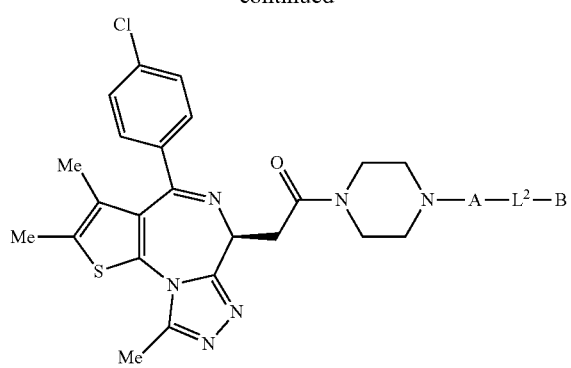
Scheme 4B.
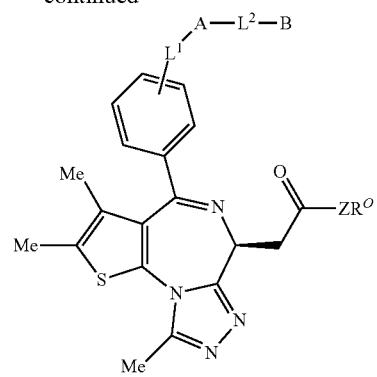
Scheme 4D.
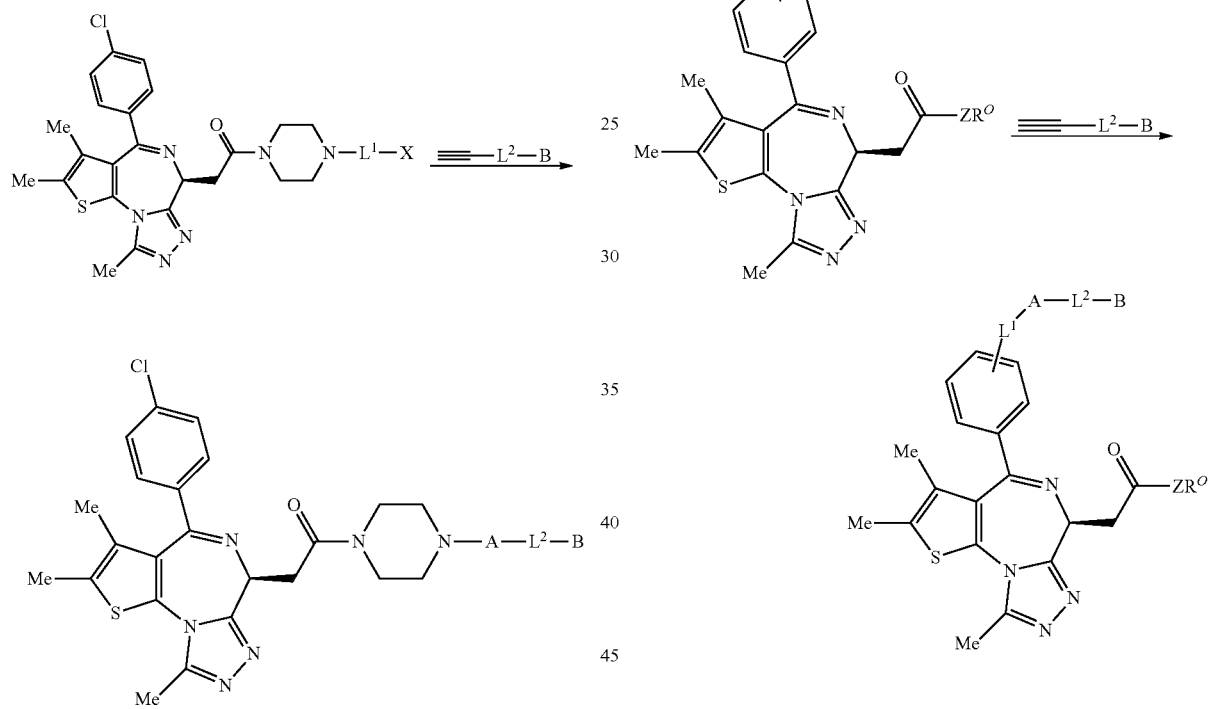
Scheme 4C.
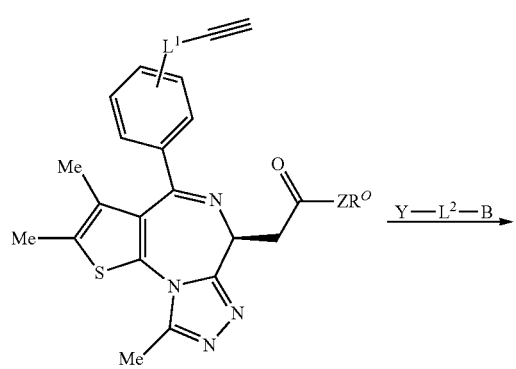
TABLE 5
| | | A | |
|---|---|---|---|
| X | Y | 1,4-adduct | 1,5-adduct |
| — | —N₃ | [triazole structure] | [triazole structure] |
| —N₃ | — | [triazole structure] | [triazole structure] |
In certain embodiments, the method of preparing a compound of Formula (I) or (II) comprises coupling (via thiol-yne addition of) a precursor compound of Formula (P-I) or (P-II) with a compound of Formula (P-III), wherein one of X and Y is

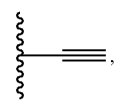

and one of X and Y is —SH to provide the compound of Formula (I) or (II). See, for example, various methods of preparing compounds of Formula (I) and (II) as provided in the below Schemes (5A) to (5D) and Table 6.

Scheme 5. Thiol-yne addition

Scheme 5A.

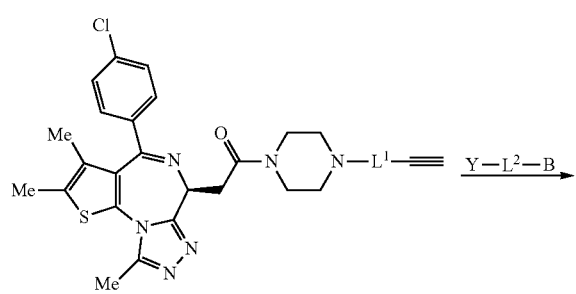

Scheme 5B.

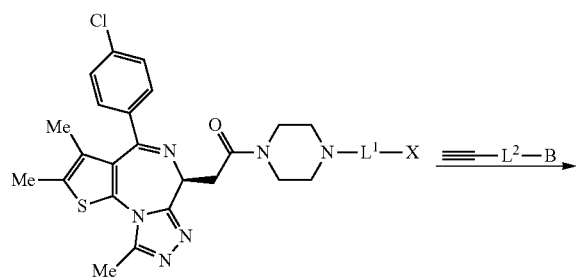

-continued

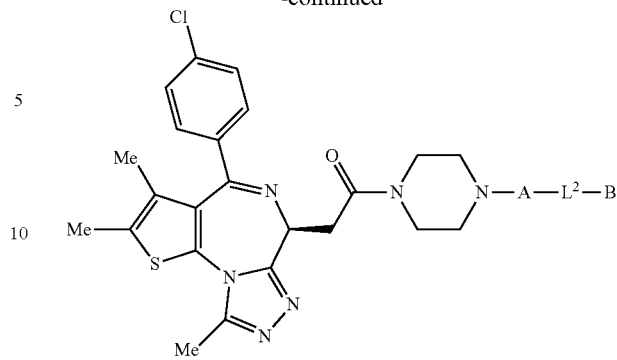

Scheme 5C.

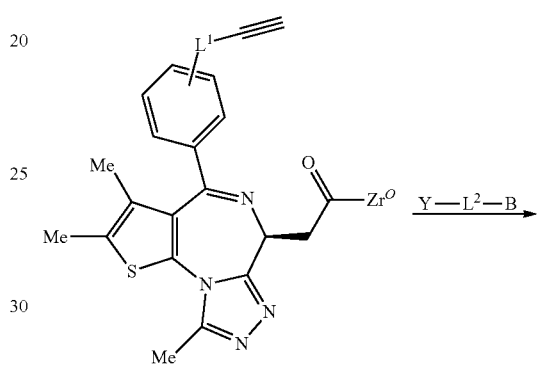

Scheme 5D.

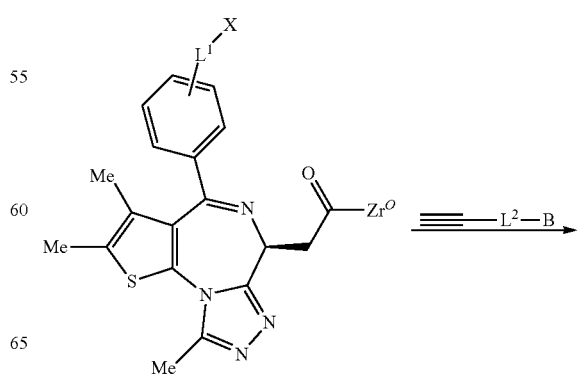

-continued

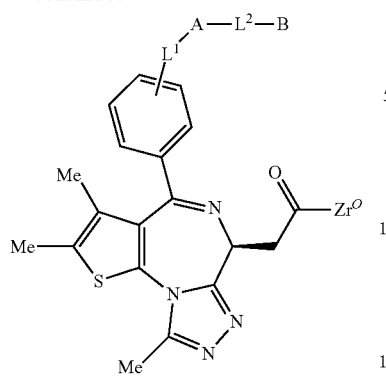

-continued

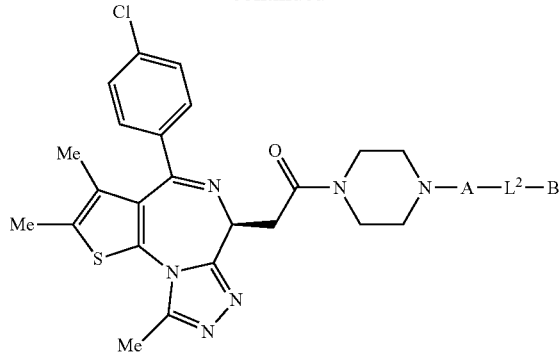

TABLE 6

| X | Y | A |
|---|---|---|
| — | —SH | (alkene-S structure) |
| —SH | — | (S-alkene structure) |

In certain embodiments, the method of preparing a compound of Formula (I) or (II) comprises coupling a precursor compound of Formula (P-I) or (P-II) with a compound of Formula (P-III), wherein one of X and Y is an aldehyde —CHO and one of X and Y is —NH$_2$ or —NH—NH$_2$ to provide the compound of Formula (I) or (II). Conditions can be formation of an imine or amine (under reductive amination conditions). See, for example, various methods of preparing compounds of Formula (I) and (II) as provided in the below Schemes (6A) to (6D) and Table 7.

Scheme 6. Imine or amine formation

Scheme 6A.

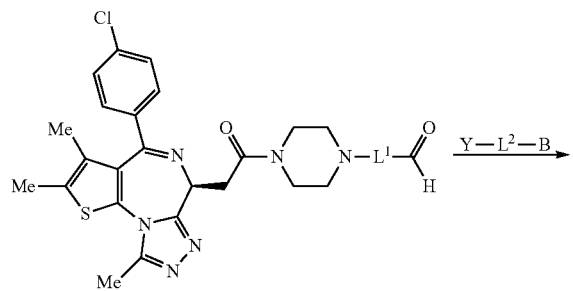

Scheme 6B.

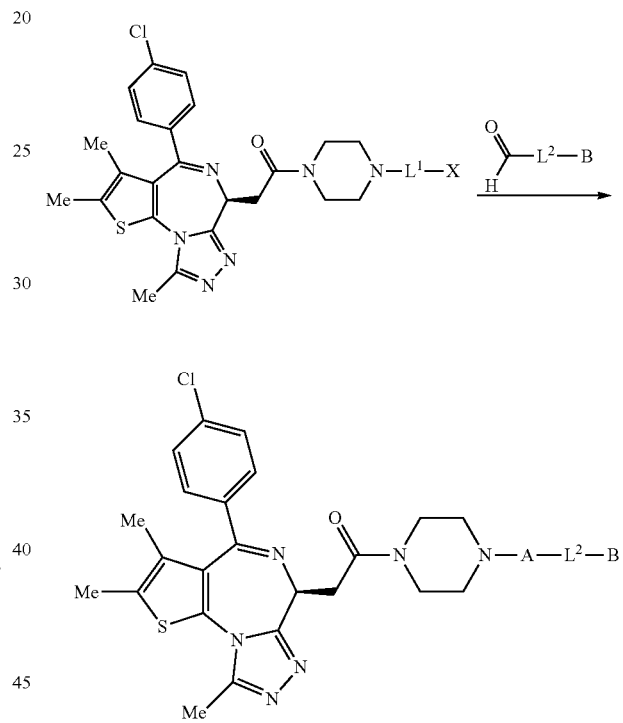

Scheme 6C.

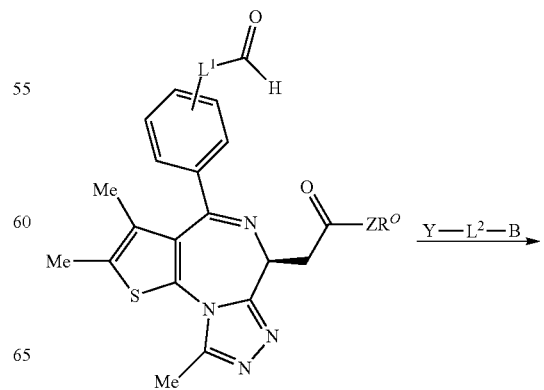

-continued

Scheme 6D.

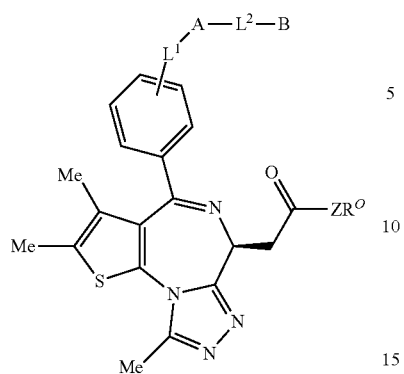

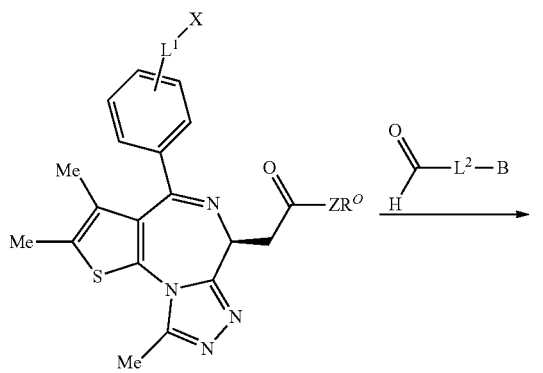

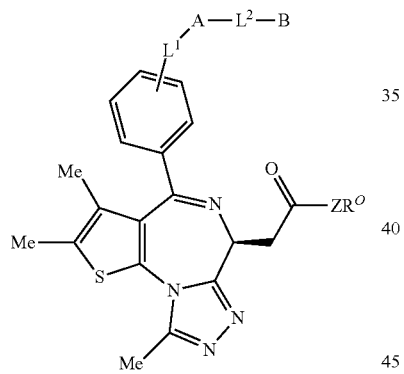

TABLE 7

| X | Y | A |
|---|---|---|
| — | —NH$_2$ | 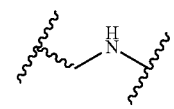 |
| — | —NH$_2$ | 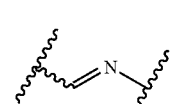 |
| — | —NH—NH$_2$ | 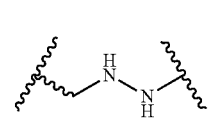 |

TABLE 7-continued

| X | Y | A |
|---|---|---|
| — | —NH—NH$_2$ | 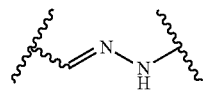 |
| —NH$_2$ | — | 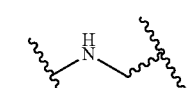 |
| —NH$_2$ | — | 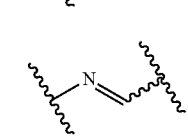 |
| —NH—NH$_2$ | — |  |
| —NH—NH$_2$ | — | 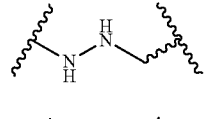 |

In certain embodiments, the method of preparing a compound of Formula (I) or (II) comprises coupling a precursor compound of Formula (P-I) or (P-II) with a compound of Formula (P-III), wherein one of X and Y is a maleimide group; and one of X and Y is —OH, —SH, —NH$_2$, or —NHNH$_2$ to provide the compound of Formula (I) or (II). See, for example, various methods of preparing compounds of Formula (I) and (II) as provided in the below Schemes 7A and 7B and Table 8.

Scheme 7. Maleimide addition and other Michael additions

Scheme 7A.

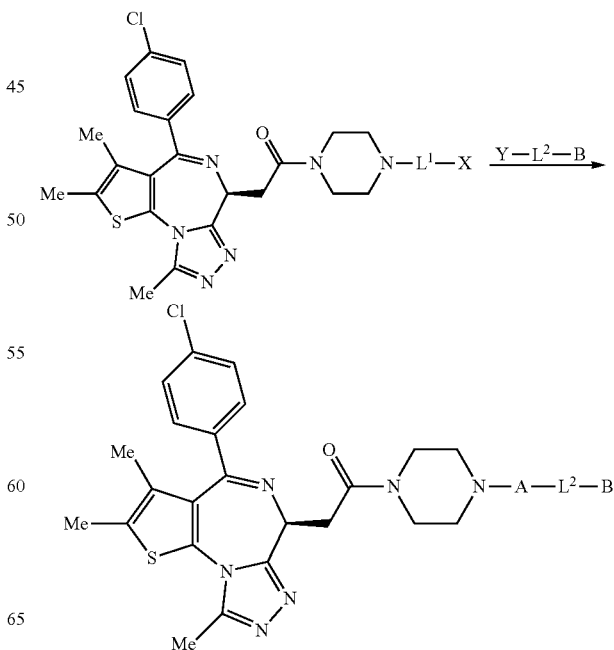

Scheme 7B.

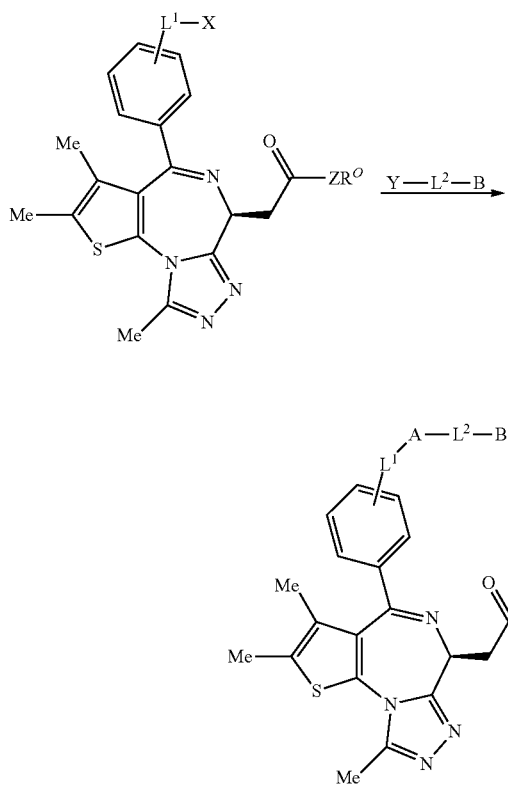

TABLE 8

| X | Y | A |
|---|---|---|
| 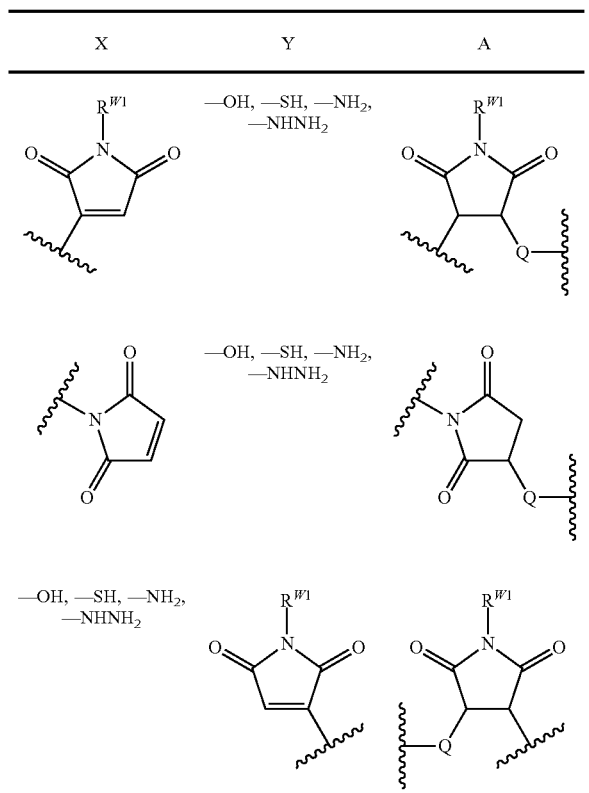 | —OH, —SH, —NH₂, —NHNH₂ | (structures shown) |

TABLE 8-continued

| X | Y | A |
|---|---|---|
| —OH, —SH, —NH₂, —NHNH₂ | (maleimide structure) | (succinimide-Q structure) |
| (acrylamide structure) | —OH, —SH, —NH₂, —NHNH₂ | (amide-Q structure) |
| —OH, —SH, —NH₂, —NHNH₂ | (vinyl ketone structure) | (ketone-Q structure) |

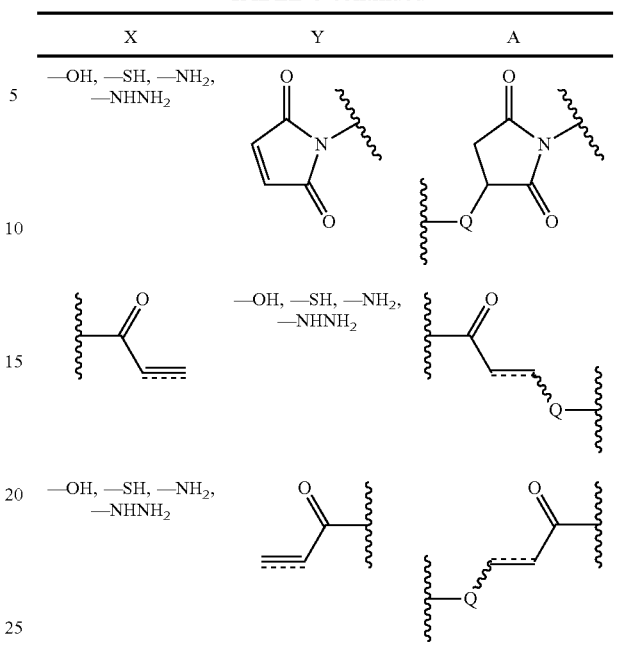

Assay Methods

As generally described herein, the present invention provides the compounds of Formula (I) and (II), and salts thereof, for use as probes in various in vitro assays. The thieondiazapine moiety can efficiently bind to bromodoamains, especially the bromodomain and extra-terminal (BET) subfamily (including BRD2, BRD3, BRD4, and BRDT). By applying the probe to different types of surfaces, variety of assays can be developed, such as alpha-assay, SPR, and microarray. The resulted assays can be used as a high-throughput assay for screening and/or evaluating small molecule inhibitors for drug discovery. The binding affinity of this molecule against bromodomain in BET subfamily can be determined by ITC (Isothermal titration calorimetry).

For example, in one aspect, provided is a method of detecting binding to a bromodomain, the method comprising contacting a compound of Formula (I) or (II), or salt thereof, in vitro to a cell or bromodomain receptor, and detecting binding of said compound to said bromodomain.

In certain embodiments, the assay is differential scanning fluorimetry (DSF), Isothermal Titration Calorimetry, or luminescence proximity homogeneous assay (ALPHA-screen). In certain embodiments, the assay is Halo-tag in order to develop a cellular assay. The probe can be used to develop an assay (biochemical assay and cellular assay) for high throughput screening to find a new scaffold for bromodomain. It can be used for target identification, such as chem-sequencing to identify the target and mechanism.

An immunoassay is a specific type of biochemical test that measures the presence or concentration of a substance (referred to as the "analyte") in solutions that frequently contain a complex mixture of substances. Analytes in biological liquids such as serum or urine are frequently assayed (i.e., measured) using immunoassay methods. In essence, the method depends upon the fact that the analyte in question is known to undergo a unique immune reaction with a second substance, which is used to determine the presence and amount of the analyte. This type of reaction involves the binding of one type of molecule, the antigen, with a second type, the antibody. Immunoassays can be carried out using either the antigen or the antibody in order to test for the other member of the antigen/antibody pair. In other words, the analyte may be either the antigen or the antibody.

For antigen analytes, an antibody that specifically binds to that antigen can frequently be prepared for use as an analytical reagent. When the analyte is a specific antibody its cognate antigen can be used as the analytical reagent. In either case the specificity of the assay depends on the degree to which the analytical reagent is able to bind to its specific binding partner to the exclusion of all other substances that might be present in the sample to be analyzed. In addition to the need for specificity, a binding partner must be selected that has a sufficiently high affinity for the analyte to permit an accurate measurement. The affinity requirements depend on the particular assay format that is used.

In addition to binding specificity, the other key feature of all immunoassays is a means to produce a measurable signal in response to a specific binding. Most immunoassays today depend on the use of an analytical reagent that is associated with a detectable label. A large variety of labels have been demonstrated including radioactive elements used in radioimmunoassays; enzymes; fluorescent, phosphorescent, and chemiluminescent dyes; latex and magnetic particles; dye crystallites, gold, silver, and selenium colloidal particles; metal chelates; coenzymes; electroactive groups; oligonucleotides, and others. Such labels serve for detection and quantitation of binding events either after separating free and bound labeled reagents or by designing the system in such a way that a binding event effects a change in the signal produced by the label. Immunoassays requiring a separation step, often called separation immunoassays or heterogeneous immunoassays, are popular because they are easy to design, but they frequently require multiple steps including careful washing of a surface onto which the labeled reagent has bound. Immunoassays in which the signal is affected by binding can often be run without a separation step. Such assays can frequently be carried out simply by mixing the reagents and sample and making a physical measurement. Such assays are called homogenous immunoassays or less frequently non-separation immunoassays.

Regardless of the method used, interpretation of the signal produced in an immunoassay requires reference to a calibrator that mimics the characteristics of the sample medium. For qualitative assays the calibrators may consist of a negative sample with no analyte and a positive sample having the lowest concentration of the analyte that is considered detectable. Quantitative assays require additional calibrators with known analyte concentrations. Comparison of the assay response of a real sample to the assay responses produced by the calibrators makes it possible to interpret the signal strength in terms of the presence or concentration of analyte in the sample.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques well known in the art, including competitive and non-competitive immunoassays, can be used. The term immunoassay encompasses techniques including, without limitation, enzyme immunoassays (EIA) such as enzyme-linked immunosorbent assay (ELISA), enzyme multiplied immunoassay technique (EMIT), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997).

Assay Kits

Various assay kits comprising one or more compounds (probes) of Formula (I) and (II), and salts thereof, are also provided.

In certain embodiments, the kit further comprises a microtiter plate. e.g., a plate that contains multiple wells, (e.g., 24, 48, 96, 128 etc.) pre-coated with antibodies directed specifically to the antigen of interest (i.e. capture antibody). As some of the wells must be devoted to blank, standard, and control solutions, depending on the manufacturer, the plate may allow up to 37 different samples tested in duplicate, or 21 in triplicate.

In certain embodiments, the kit further comprises a blank solution, e.g., a solution that contains all the substances used in the assay except the antigen to be tested. It ensures that cross-reacting substances are eliminated so that signals and readings obtained accurately reflect the antigen measured.

In certain embodiments, the kit further comprises a standard solution, e.g., a solution that contains a known amount of the antigen of interest. In certain embodiments, a series of standard solutions with different concentrations, or one with a diluent, may be provided. Standards are used to construct a standard curve to which readings from samples may be compared. These different concentrations determine the range of the assay.

Sometimes the standard solution is provided in a lyophilized (powder) form, and reconstitution to a liquid form is required.

In certain embodiments, the kit further comprises a control solution, e.g., a solution with a known amount of the antigen and will either give a positive signal (positive control) or a negative signal (negative control).

In certain embodiments, the kit further comprises a diluent solution, e.g., a solution for diluting specimens (when out of assay range), standards, and controls. An assay diluent may also be used. It is applied to the wells just before adding samples, and serves to eliminate interference or non-specific binding that may occur due to the specimen matrix.

Drug Discovery Using Compounds of Formula (I) and (II)

JQ1 binds in the binding pocket of the apo crystal structure of the first bromodomain of a BET family member (e.g., BRD4). JQ1 probes may be particularly effective in developing assays that are useful in detecting a test compound's ability to inhibit the growth, proliferation, or survival of proliferating neoplastic cells or to induce the differentiation of such cells. In certain embodiments, a test compound can bind to a BET family member and reduce the biological activity of the BET family member (e.g., reduce elongation) and/or disrupt the subcellular localization of the BET family member (e.g., reduce chromatin binding).

In certain embodiments, the test compound is identified from large libraries of natural product or synthetic (or semi-synthetic) extracts or chemical libraries or from polypeptide or nucleic acid libraries, according to methods known in the art. Virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides. Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., Proc. Natl. Acad. Sci. U.S.A. 90:6909, 1993; Erb et al., Proc. Natl. Acad. Sci. USA 91:11422, 1994; Zuckermann et al., J. Med. Chem. 37:2678, 1994; Cho et al., Science 261:1303, 1993; Carrell et al., Angew. Chem. Int. Ed. Engl. 33:2059, 1994; Carell et al., Angew. Chem. Int. Ed. Engl. 33:2061, 1994; and Gallop et al., J. Med. Chem. 37:1233, 1994. Furthermore, if desired, any library or compound is readily modified using standard chemical, physical, or biochemical methods. Libraries of compounds may be presented in solution (e.g., Houghten, Biotechniques 13:412-421, 1992), or on beads (Lam, Nature 354:82-84, 1991), chips (Fodor, Nature 364:555-556, 1993), bacteria (Ladner, U.S. Pat. No. 5,223,409), spores (Ladner U.S. Pat. No. 5,223,409), plasmids (Cull et al., Proc Natl Acad Sci USA 89:1865-1869, 1992) or on phage (Scott and Smith, Science 249:386-390, 1990; Devlin, Science 249: 404-406, 1990; Cwirla et al., Proc. Natl. Acad. Sci. 87:6378-6382, 1990; Felici, J. Mol. Biol. 222:301-310, 1991; Ladner supra.).

A test compound that specifically binds to a bromodomain of a BET family member may then be isolated and tested for activity in a secondary assay. A test compound that reduces the expression of a BET family member expressed in a cell may be used, for example, as a therapeutic to prevent, delay, ameliorate, stabilize, or treat a particular disease, e.g., such as, for example, neoplasia, proliferative disease, inflammatory disease, obesity, fatty liver (NASH or otherwise), diabetes, atherosclerosis, arterial stent occlusion, heart failure, cachexia, graft versus host disease, infection diseases associated with bromodomains, the treatment of parasites, malaria, trypanosomes, and for reducing male fertility. Further uses of the compositions of the invention include, but are not limited to, use in organ transplantation, modulation of cell state for regenerative medicine (i.e., by promoting or inhibiting cellular differentiation), and facilitating pluripotency. Test compounds that are identified as binding to a BET family member with an affinity constant less than or equal to approx 1 nM, approx 5 nM, approx 10 nM, approx 100 nM, approx 1 µM or approx 10 µM are considered particularly useful

EXAMPLES

These and other aspects of the present invention will be further appreciated upon consideration of the following Examples, which are intended to illustrate certain particular embodiments of the invention but are not intended to limit its scope, as defined by the claims.

Synthesis of JQM-PEG-Biotin

Synthesis of JQ1 follows published procedures. See, e.g., PCT Application Publication No. WO 2011/143669.

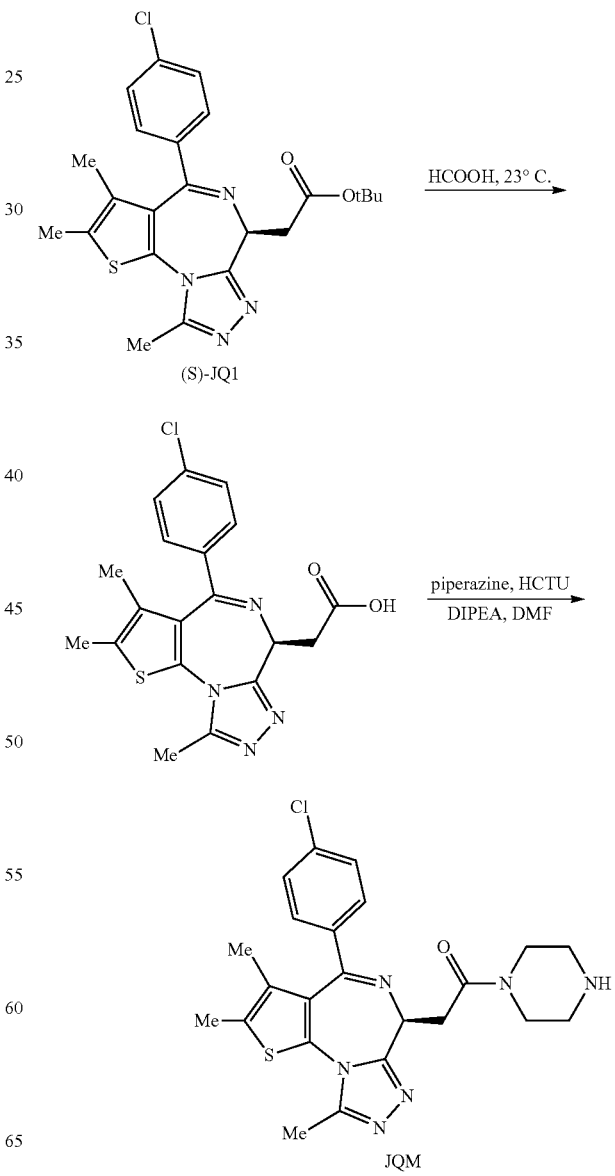

General Method A:
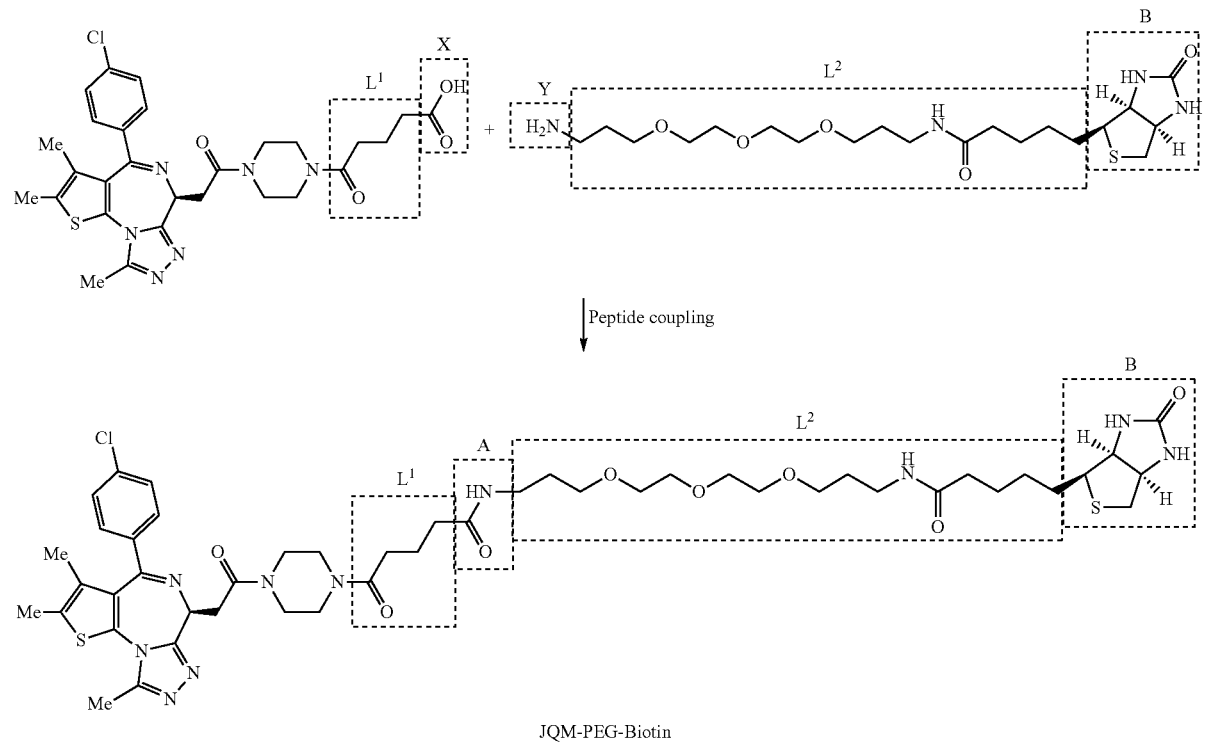
JQM-PEG-Biotin
General Method B:

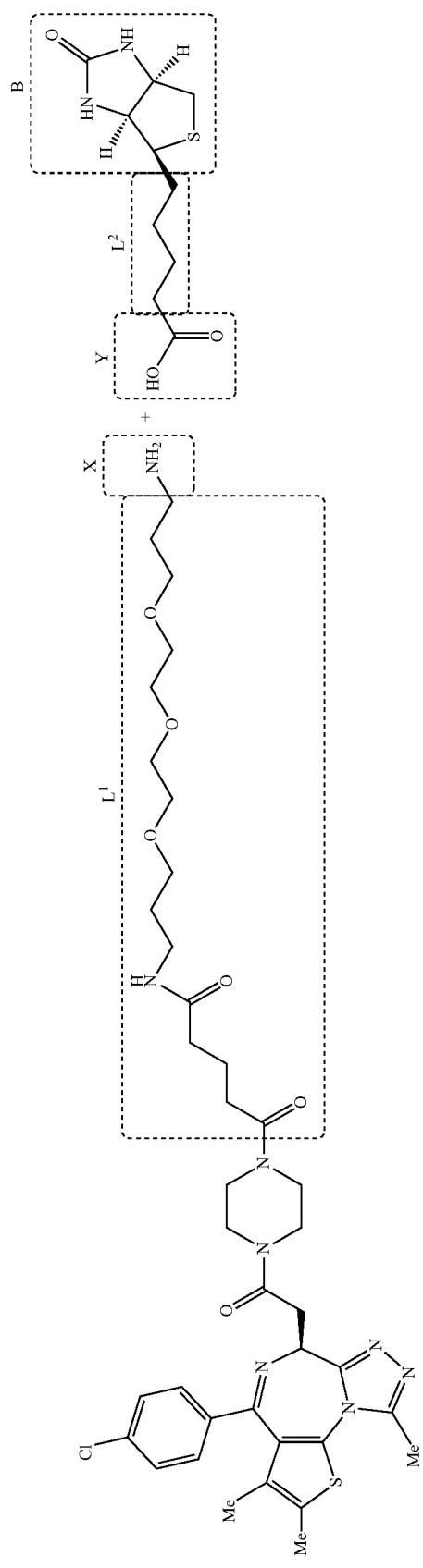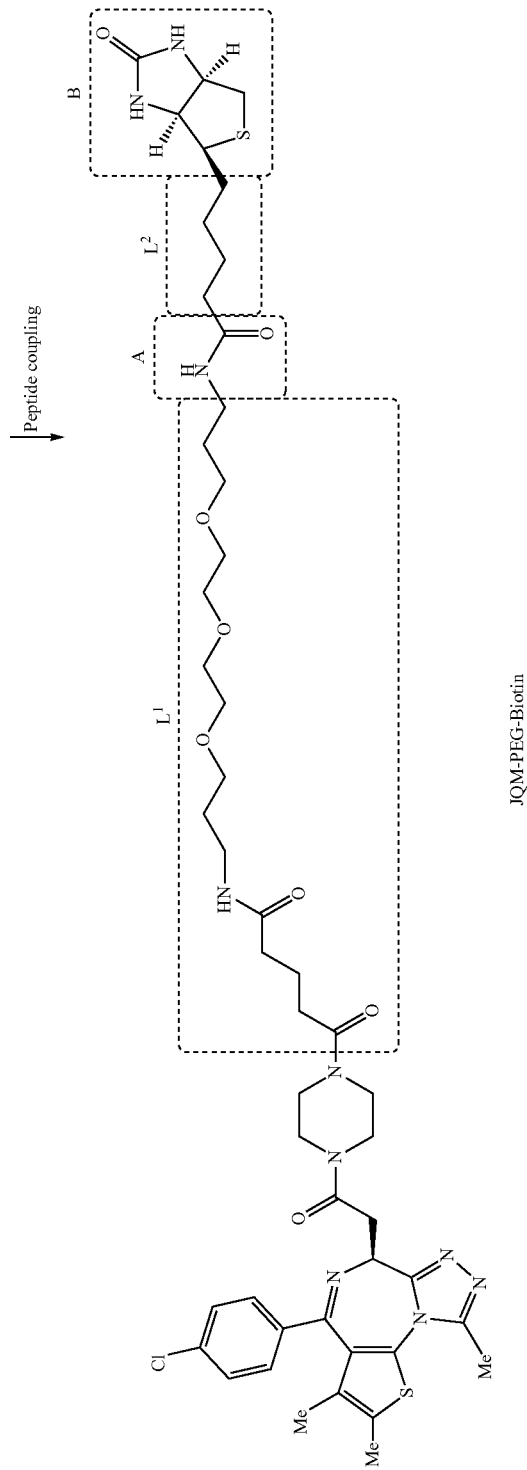
JQM-PEG-Biotin

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

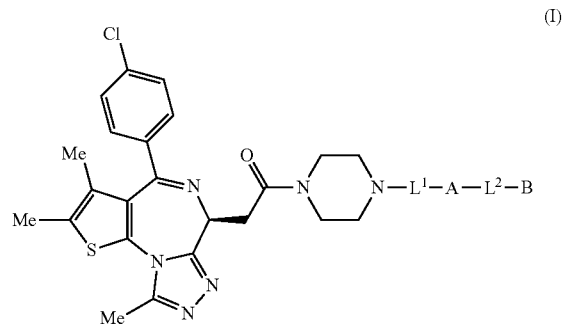

or salt thereof;
wherein:
$L^1$ is a bond or a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof;

$L^2$ is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof;

A is a bond, —NR$^{W1}$—, —NR$^{W1}$—NR$^{W1}$—, —S—, —O—, —S—S—

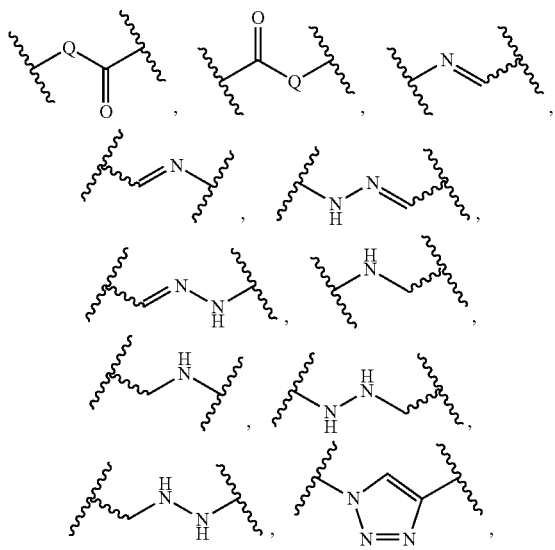

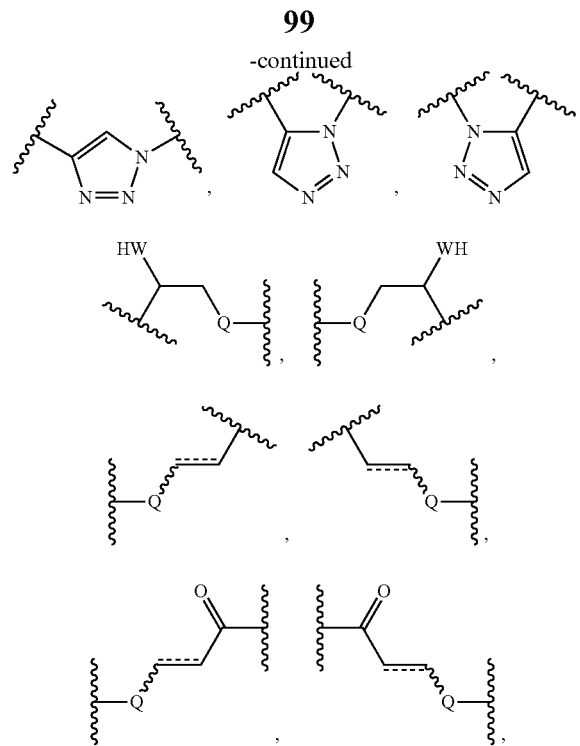

wherein ===== is a single or double bond, W is —O—, —S—, or —NR$^{W1}$—, R$^{W1}$ is hydrogen, substituted or unsubstituted alkyl, or an amino protecting group; and Q is —NR$^{W1}$—, —NR$^{W1}$—NR$^{W1}$—, —S—, —O—; and B is a detectable label.

2. The compound of claim 1, wherein L$^1$ is a linker group comprising a combination of one or more groups of the formula:

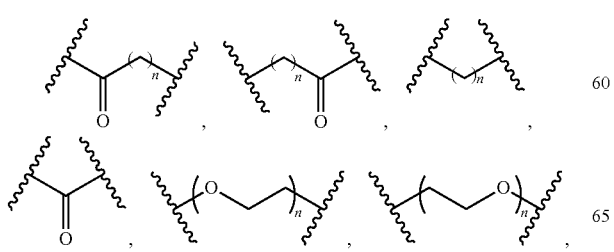

wherein R$^L$ is hydrogen or substituted or unsubstituted alkyl, n is 0 or an integer between 1 to 10, inclusive.

3. The compound of claim 1, wherein L$^2$ is a linker group comprising a combination of one or more groups of the formula:

wherein R$^L$ is hydrogen or substituted or unsubstituted alkyl, m is 0 or an integer between 1 to 10, inclusive.

4. The compound of claim 1, wherein A is

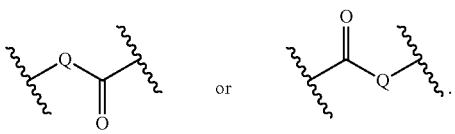

5. The compound of claim 1, wherein A is

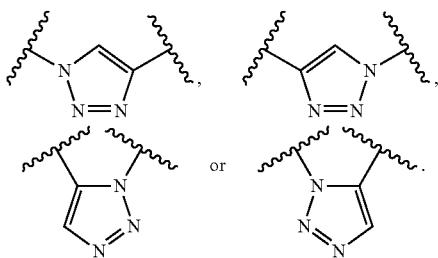

6. The compound of claim 1, wherein A is —NR$^{W1}$—, —NR$^{W1}$—NR$^{W1}$—, —S—, —O—, or —S—S—.

7. The compound of claim 1, wherein A is:

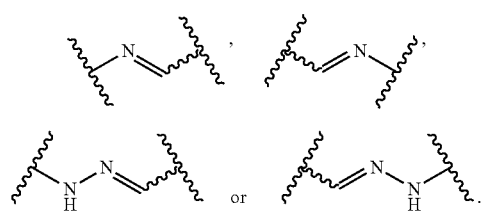

8. The compound of claim 1, wherein A is:

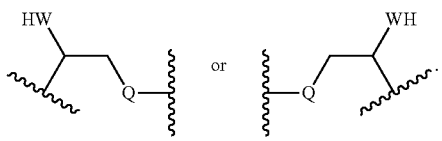

9. The compound of claim 1, wherein A is:

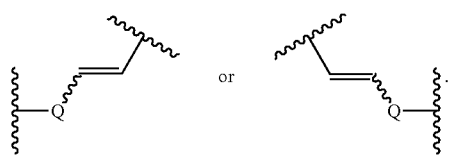

10. The compound of claim 1, wherein A is:

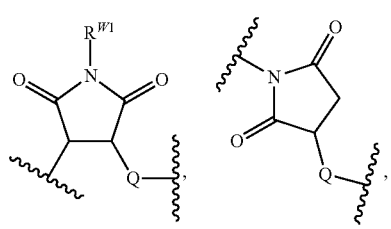

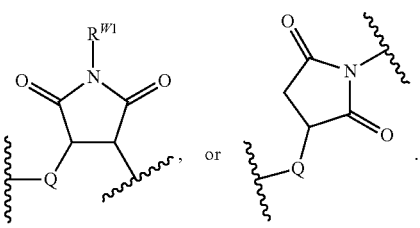

11. The compound of claim 1, wherein the compound is of formula:

(I-biotin)

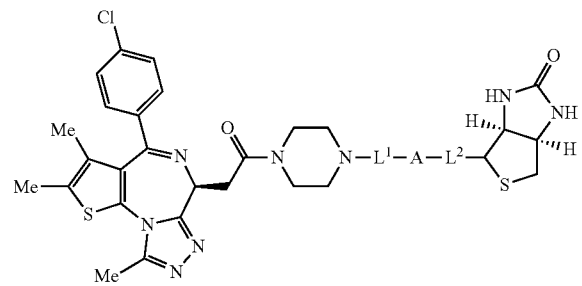

or a salt thereof.

12. The compound of claim 1, wherein the compound is of formula:

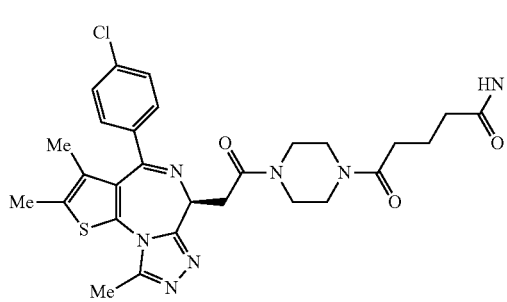

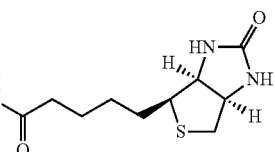

JQM-PEG-Biotin or a salt thereof.

13. The compound of claim 1, wherein the compound is of Formula:
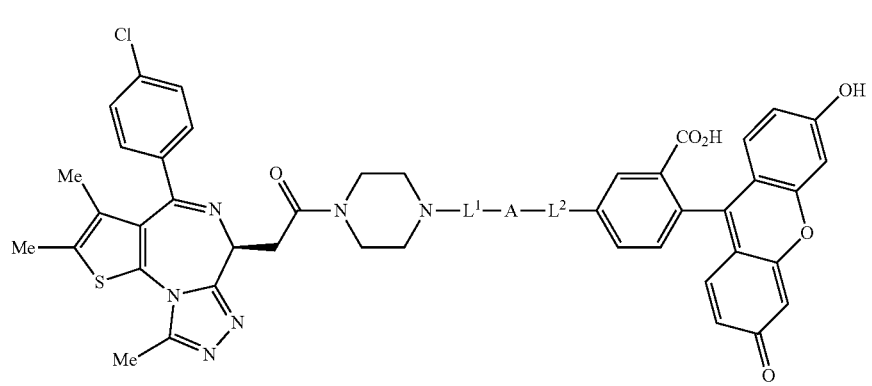
(I-FITC)
or a salt thereof.
* * * * *